US010584318B2

(12) United States Patent
Ciani et al.

(10) Patent No.: US 10,584,318 B2
(45) Date of Patent: *Mar. 10, 2020

(54) TATK-CDKL5 FUSION PROTEINS, COMPOSITIONS, FORMULATIONS, AND USE THEREOF

(71) Applicant: Alma Mater Studiorum—Universitá di Bologna, Bologna (IT)

(72) Inventors: Elisabetta Ciani, Bologna (IT); Franco Laccone, Stockerau (AT)

(73) Assignee: Alma Mater Studiorum—Università di Bologna, Bologna (IT)

( * ) Notice: Subject to any disclaimer, the term of this patent is extended or adjusted under 35 U.S.C. 154(b) by 15 days.

This patent is subject to a terminal disclaimer.

(21) Appl. No.: 15/954,021

(22) Filed: Apr. 16, 2018

(65) Prior Publication Data
US 2018/0327725 A1 Nov. 15, 2018

Related U.S. Application Data

(63) Continuation of application No. 15/075,457, filed on Mar. 21, 2016, now Pat. No. 9,944,910, which is a continuation of application No. 14/633,757, filed on Feb. 27, 2015, now Pat. No. 9,290,746.

(60) Provisional application No. 61/946,280, filed on Feb. 28, 2014.

(51) Int. Cl.
 *C07K 14/475* (2006.01)
 *C12N 9/12* (2006.01)
 *C07K 14/47* (2006.01)
 *A61K 38/00* (2006.01)

(52) U.S. Cl.
 CPC ............ *C12N 9/12* (2013.01); *C07K 14/4737* (2013.01); *C07K 14/4738* (2013.01); *C12N 9/1205* (2013.01); *A61K 38/00* (2013.01); *C07K 2319/01* (2013.01); *C07K 2319/10* (2013.01); *C07K 2319/21* (2013.01); *C07K 2319/41* (2013.01); *C07K 2319/60* (2013.01); *C12N 2501/405* (2013.01); *C12Y 207/11022* (2013.01)

(58) Field of Classification Search
None
See application file for complete search history.

(56) References Cited

U.S. PATENT DOCUMENTS

| 9,290,746 B2 * | 3/2016 | Ciani | C12N 9/12 |
| 9,944,910 B2 * | 4/2018 | Ciani | C12N 9/12 |
| 2015/0247134 A1 * | 9/2015 | Ciani | C12N 9/12 424/94.5 |
| 2016/0194617 A1 * | 7/2016 | Ciani | C12N 9/12 424/94.5 |

* cited by examiner

*Primary Examiner* — John D Ulm
(74) *Attorney, Agent, or Firm* — Servilla Whitney LLC

(57) ABSTRACT

Disclosed herein are compositions and formulations containing a TATk-CDKL5 fusion protein. Also disclosed are methods of producing a TATk-CDKL5 fusion protein from vectors containing a TATk-CDKL5 cDNA and methods of transducing cells with the vectors containing a TATk-CDKL5 cDNA and the TATk-CDKL5 fusion protein.

20 Claims, 27 Drawing Sheets

Specification includes a Sequence Listing.

Untreated 293T        TATk-GFP-CDKL5 treated 293T

TATk-GFP
treated SH-SY5Y
TATk-GFP-CDKL5
treated SH-SY5Y
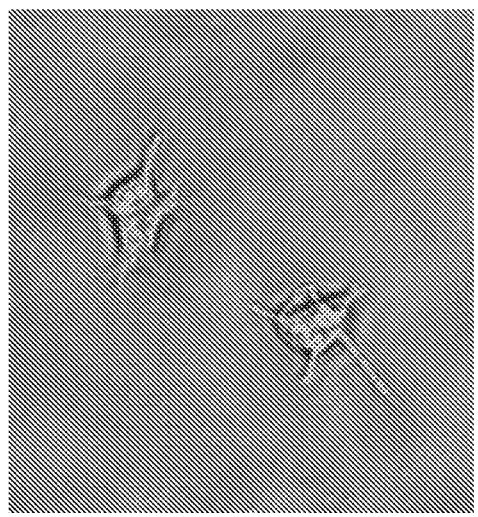
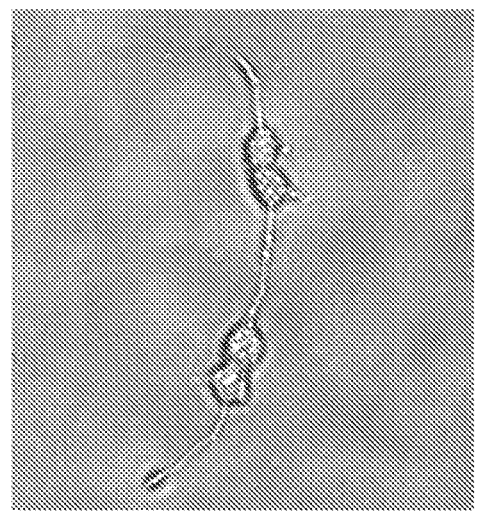
Fig. 11A
Fig. 11B
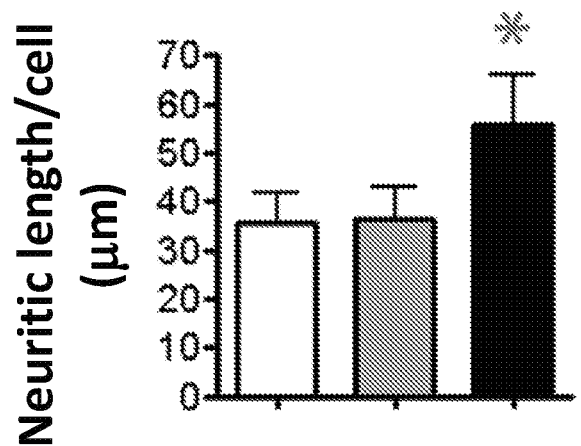
Fig. 12

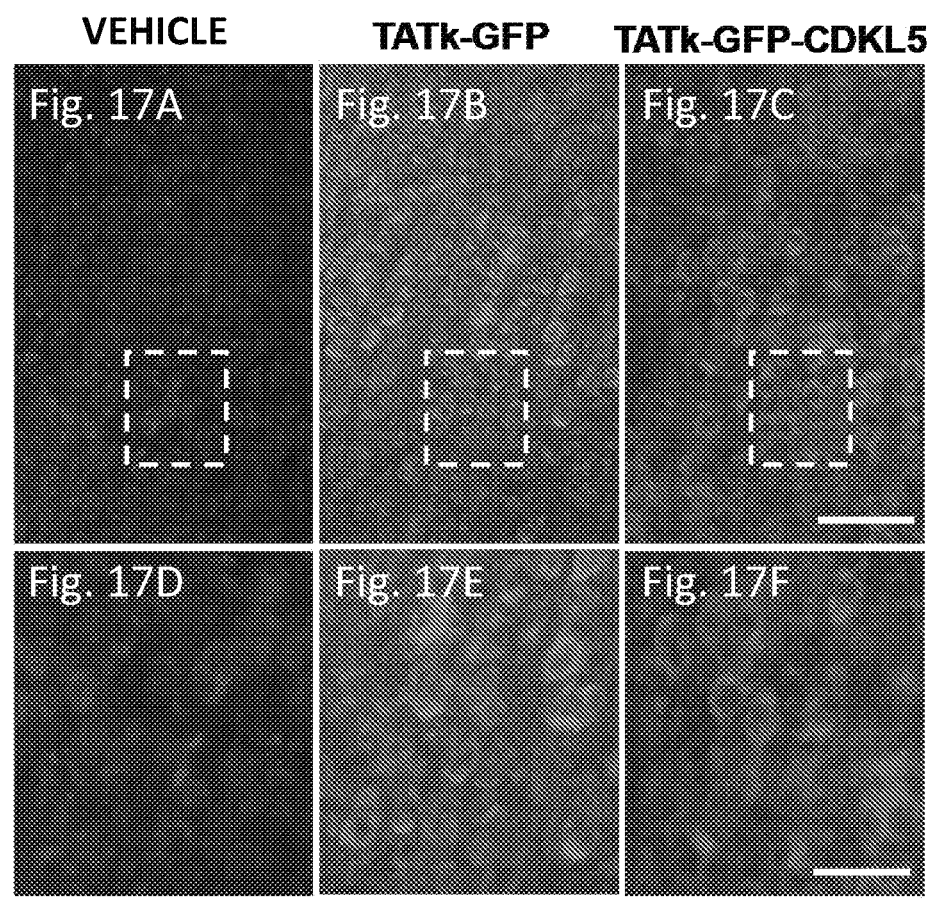
Fig. 17A-F

VEHICLE

PL

TATk-GFP-CDKL5

☐ +/Y ■ -/Y ▨ -/Y + TATk-GFP-CDKL5

Cleaved Caspase 3-positive cells

DCX-positive cells

☐ +/Y ■ -/Y ▨ -/Y + TATk-GFP-CDKL5

Hippocampus (molecular layer)

Cortex (layer III)

Hippocampus (molecular layer)

Cortex (layer V)

SEQUENCE LISTING

```
<160> NUMBER OF SEQ ID NOS: 16

<210> SEQ ID NO 1
<211> LENGTH: 727
<212> TYPE: DNA
<213> ORGANISM: Artificial Sequence
<220> FEATURE:
<223> OTHER INFORMATION: CDKL5

<400> SEQUENCE: 1
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccaccc tgacctacgg cgtgcagtgc ttcagccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
```

```
aaccgcatcg agctgaaggg catcgacttc aaggaggacg gcaacatcct ggggcacaag    420
ctggagtaca actacaacag ccacaacgtc tatatcatgg ccgacaagca gaagaacggc    480
atcaaggtga acttcaagat ccgccacaac atcgaggacg gcagcgtgca gctcgccgac    540
cactaccagc agaacacccc catcggcgac ggccccgtgc tgctgcccga caaccactac    600
ctgagcaccc agtccgccct gagcaaagac cccaacgaga gcgcgatca catggtcctg    660 ctggagttcg tgaccgccgc cgggatcact ctcggcatgg acgagctgta caagtccgga    720
ctcagat                                                              727
```

<210> SEQ ID NO 2
<211> LENGTH: 1029
<212> TYPE: PRT
<213> ORGANISM: Artificial Sequence
<220> FEATURE:
<223> OTHER INFORMATION: CDKL5

<400> SEQUENCE: 2

```
Lys Ile Pro Asn Ile Gly Asn Val Met Asn Lys Phe Glu Ile Leu Gly
1               5                   10                  15

Val Val Gly Glu Gly Ala Tyr Gly Val Val Leu Lys Cys Arg His Lys
            20                  25                  30

Glu Thr His Glu Ile Val Ala Ile Lys Lys Phe Lys Asp Ser Glu Glu
        35                  40                  45

Asn Glu Glu Val Lys Glu Thr Thr Leu Arg Glu Leu Lys Met Leu Arg
    50                  55                  60

Thr Leu Lys Gln Glu Asn Ile Val Glu Leu Lys Glu Ala Phe Arg Arg
65                  70                  75                  80

Arg Gly Lys Leu Tyr Leu Val Phe Glu Tyr Val Glu Lys Asn Met Leu
                85                  90                  95

Glu Leu Leu Glu Glu Met Pro Asn Gly Val Pro Pro Glu Lys Val Lys
            100                 105                 110

Ser Tyr Ile Tyr Gln Leu Ile Lys Ala Ile His Trp Cys His Lys Asn
        115                 120                 125

Asp Ile Val His Arg Asp Ile Lys Pro Glu Asn Leu Leu Ile Ser His
    130                 135                 140

Asn Asp Val Leu Lys Leu Cys Asp Phe Gly Phe Ala Arg Asn Leu Ser
145                 150                 155                 160

Glu Gly Asn Asn Ala Asn Tyr Thr Glu Tyr Val Ala Thr Arg Trp Tyr
                165                 170                 175

Arg Ser Pro Glu Leu Leu Leu Gly Ala Pro Tyr Gly Lys Ser Val Asp
            180                 185                 190

Met Trp Ser Val Gly Cys Ile Leu Gly Glu Leu Ser Asp Gly Gln Pro
        195                 200                 205

Leu Phe Pro Gly Glu Ser Glu Ile Asp Gln Leu Phe Thr Ile Gln Lys
    210                 215                 220

Val Leu Gly Pro Leu Pro Ser Glu Gln Met Lys Leu Phe Tyr Ser Asn
225                 230                 235                 240

Pro Arg Phe His Gly Leu Arg Phe Pro Ala Val Asn His Pro Gln Ser
                245                 250                 255

Leu Glu Arg Arg Tyr Leu Gly Ile Leu Asn Ser Val Leu Leu Asp Leu
            260                 265                 270

Met Lys Asn Leu Leu Lys Leu Asp Pro Ala Asp Arg Tyr Leu Thr Glu
        275                 280                 285
```

-continued

```
Gln Cys Leu Asn His Pro Thr Phe Gln Thr Gln Arg Leu Leu Asp Arg
290                 295                 300

Ser Pro Ser Arg Ser Ala Lys Arg Lys Pro Tyr His Val Glu Ser Ser
305                 310                 315                 320

Thr Leu Ser Asn Arg Asn Gln Ala Gly Lys Ser Thr Ala Leu Gln Ser
                325                 330                 335

His His Arg Ser Asn Ser Lys Asp Ile Gln Asn Leu Ser Val Gly Leu
            340                 345                 350

Pro Arg Ala Asp Glu Gly Leu Pro Ala Asn Glu Ser Phe Leu Asn Gly
        355                 360                 365

Asn Leu Ala Gly Ala Ser Leu Ser Pro Leu His Thr Lys Thr Tyr Gln
370                 375                 380

Ala Ser Ser Gln Pro Gly Ser Thr Ser Lys Asp Leu Thr Asn Asn Asn
385                 390                 395                 400

Ile Pro His Leu Leu Ser Pro Lys Glu Ala Lys Ser Lys Thr Glu Phe
                405                 410                 415

Asp Phe Asn Ile Asp Pro Lys Pro Ser Glu Gly Pro Gly Thr Lys Tyr
            420                 425                 430

Leu Lys Ser Asn Ser Arg Ser Gln Gln Asn Arg His Ser Phe Met Glu
        435                 440                 445

Ser Ser Gln Ser Lys Ala Gly Thr Leu Gln Pro Asn Glu Lys Gln Ser
450                 455                 460

Arg His Ser Tyr Ile Asp Thr Ile Pro Gln Ser Arg Ser Pro Ser
465                 470                 475                 480

Tyr Arg Thr Lys Ala Lys Ser His Gly Ala Leu Ser Asp Ser Lys Ser
            485                 490                 495

Val Ser Asn Leu Ser Glu Ala Arg Ala Gln Ile Ala Glu Pro Ser Thr
        500                 505                 510

Ser Arg Tyr Phe Pro Ser Ser Cys Leu Asp Leu Asn Ser Pro Thr Ser
        515                 520                 525

Pro Thr Pro Thr Arg His Ser Asp Thr Arg Thr Leu Leu Ser Pro Ser
530                 535                 540

Gly Arg Asn Asn Arg Asn Glu Gly Thr Leu Asp Ser Arg Arg Thr Thr
545                 550                 555                 560

Thr Arg His Ser Lys Thr Met Glu Glu Leu Lys Leu Pro Glu His Met
            565                 570                 575

Asp Ser Ser His Ser His Ser Leu Ser Ala Pro His Glu Ser Phe Ser
        580                 585                 590

Tyr Gly Leu Gly Tyr Thr Ser Pro Phe Ser Ser Gln Gln Arg Pro His
        595                 600                 605

Arg His Ser Met Tyr Val Thr Arg Asp Lys Val Arg Ala Lys Gly Leu
610                 615                 620

Asp Gly Ser Leu Ser Ile Gly Gln Gly Met Ala Ala Arg Ala Asn Ser
625                 630                 635                 640

Leu Gln Leu Leu Ser Pro Gln Pro Gly Glu Gln Leu Pro Pro Glu Met
                645                 650                 655

Thr Val Ala Arg Ser Ser Val Lys Glu Thr Ser Arg Glu Gly Thr Ser
            660                 665                 670

Ser Phe His Thr Arg Gln Lys Ser Glu Gly Gly Val Tyr His Asp Pro
        675                 680                 685

His Ser Asp Asp Gly Thr Ala Pro Lys Glu Asn Arg His Leu Tyr Asn
690                 695                 700

Asp Pro Val Pro Arg Arg Val Gly Ser Phe Tyr Arg Val Pro Ser Pro
```

-continued

```
            705                 710                 715                 720
        Arg Pro Asp Asn Ser Phe His Glu Asn Asn Val Ser Thr Arg Val Ser
                        725                 730                 735

Ser Leu Pro Ser Glu Ser Ser Gly Thr Asn His Ser Lys Arg Gln
                        740                 745                 750

Pro Ala Phe Asp Pro Trp Lys Ser Pro Glu Asn Ile Ser His Ser Glu
                        755                 760                 765

Gln Leu Lys Glu Lys Lys Gln Gly Phe Phe Arg Ser Met Lys Lys
                770                 775                 780

Lys Lys Lys Lys Ser Gln Thr Val Pro Asn Ser Asp Ser Pro Asp Leu
        785                 790                 795                 800

Leu Thr Leu Gln Lys Ser Ile His Ser Ala Ser Thr Pro Ser Ser Arg
                        805                 810                 815

Pro Lys Glu Trp Arg Pro Glu Lys Ile Ser Asp Leu Gln Thr Gln Ser
                        820                 825                 830

Gln Pro Leu Lys Ser Leu Arg Lys Leu Leu His Leu Ser Ser Ala Ser
                835                 840                 845

Asn His Pro Ala Ser Ser Asp Pro Arg Phe Gln Pro Leu Thr Ala Gln
                850                 855                 860

Gln Thr Lys Asn Ser Phe Ser Glu Ile Arg Ile His Pro Leu Ser Gln
        865                 870                 875                 880

Ala Ser Gly Gly Ser Ser Asn Ile Arg Gln Glu Pro Ala Pro Lys Gly
                        885                 890                 895

Arg Pro Ala Leu Gln Leu Pro Asp Gly Gly Cys Asp Gly Arg Arg Gln
                        900                 905                 910

Arg His His Ser Gly Pro Gln Asp Arg Arg Phe Met Leu Arg Thr Thr
                        915                 920                 925

Glu Gln Gln Gly Glu Tyr Phe Cys Cys Gly Asp Pro Lys Pro His
                930                 935                 940

Thr Pro Cys Val Pro Asn Arg Ala Leu His Arg Pro Ile Ser Ser Pro
        945                 950                 955                 960

Ala Pro Tyr Pro Val Leu Gln Val Arg Gly Thr Ser Met Cys Pro Thr
                        965                 970                 975

Leu Gln Val Arg Gly Thr Asp Ala Phe Ser Cys Pro Thr Gln Gln Ser
                        980                 985                 990

Gly Phe Ser Phe Phe Val Arg His Val Met Arg Glu Ala Leu Ile His
                995                 1000                1005

Arg Ala Gln Val Asn Gln Ala Ala Leu Leu Thr Tyr His Glu Asn
                1010                1015                1020

Ala Ala Leu Thr Gly Lys
                1025
```

<210> SEQ ID NO 3
<211> LENGTH: 33
<212> TYPE: DNA
<213> ORGANISM: Artificial Sequence
<220> FEATURE:
<223> OTHER INFORMATION: TATk

<400> SEQUENCE: 3
tacgccagaa aggccgccag gcaggccagg gca                33

<210> SEQ ID NO 4
<211> LENGTH: 11
<212> TYPE: PRT
<213> ORGANISM: Artificial Sequence

```
<220> FEATURE:
<223> OTHER INFORMATION: TATk

<400> SEQUENCE: 4

Tyr Ala Arg Lys Ala Ala Arg Gln Ala Arg Ala
1               5                   10

<210> SEQ ID NO 5
<211> LENGTH: 60
<212> TYPE: DNA
<213> ORGANISM: Artificial Sequence
<220> FEATURE:
<223> OTHER INFORMATION: Igk-chain leader sequence

<400> SEQUENCE: 5
atggagacag acacactcct gctatgggta ctgctgctct gggttccagg ttccactggt    60

<210> SEQ ID NO 6
<211> LENGTH: 20
<212> TYPE: PRT
<213> ORGANISM: Artificial Sequence
<220> FEATURE:
<223> OTHER INFORMATION: Igk-chain leder sequence

<400> SEQUENCE: 6

Met Glu Thr Asp Thr Leu Leu Leu Trp Val Leu Leu Leu Trp Val Pro
1               5                   10                  15

Gly Ser Thr Gly
            20

<210> SEQ ID NO 7
<211> LENGTH: 3318
<212> TYPE: DNA
<213> ORGANISM: Artificial Sequence
<220> FEATURE:
<223> OTHER INFORMATION: TATk-CDKL5 fusion protein cDNA

<400> SEQUENCE: 7
atggagacag acacactcct gctatgggta ctgctgctct gggttccagg ttccactggt      60
gacgcggccc agccggccag gcgcgcgcgc cgtacgaagc ttgcggccta cgccagaaag     120
gccgccaggc aggccagggc accggtgaag attcctaaca ttggtaatgt gatgaataaa     180
tttgagatcc ttgggggttgt aggtgaagga gcctatggag ttgtacttaa atgcagacac     240
aaggaaacac atgaaattgt ggcgatcaag aaattcaagg acagtgaaga aatgaagaa      300 gtcaaagaaa cgactttacg agagcttaaa atgcttcgga ctctcaagca ggaaaacatt     360
gtggagttga aggaagcatt tcgtcggagg ggaaagttgt acttggtgtt tgagtatgtt     420
gaaaaaaata tgctcgaatt gctggaagaa atgccaaatg gagttccacc tgagaaagta     480
aaaagctaca tctatcagct aatcaaggct attcactggt gccataagaa tgatattgtc     540
catcgagata taaaaccaga aaatctctta atcagccaca atgatgtcct aaaactgtgt     600
gactttggtt ttgctcgtaa tctgtcagaa ggcaataatg ctaattacac agagtacgtt     660
gccaccagat ggtatcggtc cccagaactc ttacttggcg ctccctatgg aaagtccgtg     720
gacatgtggt cggtgggctg tattcttggg gagcttagcg atggacagcc tttatttcct     780
ggagaaagtg aaattgacca actttttact attcagaagg tgctaggacc acttccatct     840
gagcagatga agcttttcta cagtaatcct cgcttccatg gctccggtt tccagctgtt     900 aaccatcctc agtccttgga agaagatac cttggaattt tgaatagtgt tctacttgac     960
ctaatgaaga atttactgaa gttggaccca gctgacagat acttgacaga acagtgtttg    1020
```

```
aatcaccota catttcaaac ccagagactt ctggatcgtt ctccttcaag gtcagcaaaa      1080
agaaaacctt accatgtgga aagcagcaca ttgtctaata gaaaccaagc cggcaaaagt      1140
actgctttgc agtctcacca cagatctaac agcaaggaca tccagaacct gagtgtaggc      1200
ctgccccggg ctgacgaagg tctccctgcc aatgaaagct tcctaaatgg aaaccttgct      1260
ggagctagtc ttagtccact gcacaccaaa acctaccaag caagcagcca gcctgggtct      1320
accagcaaag atctcaccaa caacaacata ccacaccttc ttagcccaaa agaagccaag      1380
tcaaaaacag agtttgattt taatattgac ccaaagcctt cagaaggccc agggacaaag      1440
tacctcaagt caaacagcag atctcagcag aaccgccact cattcatgga aagctctcaa      1500
agcaaagctg ggacactgca gcccaatgaa aagcagagtc ggcatagcta tattgacaca      1560
attccccagt cctctaggag tccctcctac aggaccaagg ccaaaagcca tggggcactg      1620
agtgactcca agtctgtgag caacctttct gaagccaggg cccaaattgc ggagcccagt      1680
accagtaggt acttcccatc tagctgctta gacttgaatt ctcccaccag cccaaccccc      1740
accagacaca gtgacacgag aactttgctc agcccttctg gaagaaataa ccgaaatgag      1800
ggaacgctgg actcacgtcg aaccacaacc agacattcta agacgatgga ggaattgaag      1860
ctgccggagc acatggacag tagccattcc cattcactgt ctgcacctca cgaatctttt      1920
tcttatggac tgggctacac cagccccttt tcttcccagc aacgtcctca taggcattct      1980
atgtatgtga cccgtgacaa agtgagagcc aagggcttgg atggaagctt gagcataggg      2040
caagggatgg cagctagagc caacagcctg caactcttgt caccccagcc tggagaacag      2100
ctccctccag agatgactgt ggcaagatct tcggtcaaag agacctccag agaaggcacc      2160
tcttccttcc atacacgcca gaagtctgag ggtggagtgt atcatgaccc acactctgat      2220
gatggcacag cccccaaaga aaatagacac ctatacaatg atcctgtgcc aaggagagtt      2280
ggtagctttt acagagtgcc atctccacgt ccagacaatt cttttccatga aaataatgtg      2340 tcaactagag tttcttctct accatcagag agcagttctg gaaccaacca ctcaaaaaga      2400
caaccagcat tcgatccatg gaaaagtcct gaaaatatta gtcattcaga gcaactcaag      2460 gaaaagaga agcaaggatt tttcaggtca atgaaaaga aaaagaagaa atctcaaaca      2520
gtacccaatt ccgacagccc tgatcttctg acgttgcaga aatccattca ttctgctagc      2580
actccaagca gcagaccaaa gggagtggcgc cccgagaaga tctcagatct gcagacccaa      2640
agccagccat taaaatcact gcgcaagttg ttacatctct cttcggcctc aaatcacccg      2700
gcttcctcag atccccgctt ccagccctta acagctcaac aaaccaaaaa ttccttctca      2760
gaaattcgga ttcacccct gagccaggcc tctggcggga gcagcaacat ccggcaggaa      2820
cccgcaccga agggcaggcc agccctccag ctgccagacg tggatgtgga tgcagaaga      2880 cagagacacc attctggacc ccaagataga cgcttcatgt taaggacgac agaacaacaa      2940
ggagaatact tctgctgtgg tgacccaaag aagcctcaca ctccgtgcgt cccaaaccga      3000
gcccttcatc gtccaatctc cagtcctgct ccctatccag tactccaggt ccgaggcact      3060
tccatgtgcc cgacactcca ggtccgaggc actgatgctt tcagctgccc aacccagcaa      3120
tccgggttct ctttcttcgt gagacacgtt atgagggaag ccctgattca cagggcccag      3180
gtaaaccaag ctgcgctcct gacataccat gagaatgcgg cactgacggg caagtccgct      3240
cgaggagggc ccgaacaaaa actcatctca gaagaggatc tgaatagcgc cgtcgaccat      3300
catcatcatc atcattga                                                  3318
```

```
<210> SEQ ID NO 8
<211> LENGTH: 1105
<212> TYPE: PRT
<213> ORGANISM: Artificial Sequence
<220> FEATURE:
<223> OTHER INFORMATION: TATk-CDKL5 fusion protein polypeptide

<400> SEQUENCE: 8

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Ala Ala Tyr Ala Arg Lys Ala Ala Arg Gln Ala Arg Ala Pro
        35                  40                  45

Val Lys Ile Pro Asn Ile Gly Asn Val Met Asn Lys Phe Glu Ile Leu
    50                  55                  60

Gly Val Val Gly Glu Gly Ala Tyr Gly Val Val Leu Lys Cys Arg His
65                  70                  75                  80

Lys Glu Thr His Glu Ile Val Ala Ile Lys Lys Phe Lys Asp Ser Glu
                85                  90                  95

Glu Asn Glu Glu Val Lys Glu Thr Thr Leu Arg Glu Leu Lys Met Leu
            100                 105                 110

Arg Thr Leu Lys Gln Glu Asn Ile Val Glu Leu Lys Glu Ala Phe Arg
        115                 120                 125

Arg Arg Gly Lys Leu Tyr Leu Val Phe Glu Tyr Val Glu Lys Asn Met
    130                 135                 140

Leu Glu Leu Leu Glu Glu Met Pro Asn Gly Val Pro Pro Glu Lys Val
145                 150                 155                 160

Lys Ser Tyr Ile Tyr Gln Leu Ile Lys Ala Ile His Trp Cys His Lys
                165                 170                 175

Asn Asp Ile Val His Arg Asp Ile Lys Pro Glu Asn Leu Leu Ile Ser
            180                 185                 190

His Asn Asp Val Leu Lys Leu Cys Asp Phe Gly Phe Ala Arg Asn Leu
        195                 200                 205

Ser Glu Gly Asn Asn Ala Asn Tyr Thr Glu Tyr Val Ala Thr Arg Trp
    210                 215                 220

Tyr Arg Ser Pro Glu Leu Leu Leu Gly Ala Pro Tyr Gly Lys Ser Val
225                 230                 235                 240

Asp Met Trp Ser Val Gly Cys Ile Leu Gly Glu Leu Ser Asp Gly Gln
                245                 250                 255

Pro Leu Phe Pro Gly Glu Ser Glu Ile Asp Gln Leu Phe Thr Ile Gln
            260                 265                 270

Lys Val Leu Gly Pro Leu Pro Ser Glu Gln Met Lys Leu Phe Tyr Ser
        275                 280                 285

Asn Pro Arg Phe His Gly Leu Arg Phe Pro Ala Val Asn His Pro Gln
    290                 295                 300

Ser Leu Glu Arg Arg Tyr Leu Gly Ile Leu Asn Ser Val Leu Leu Asp
305                 310                 315                 320

Leu Met Lys Asn Leu Leu Lys Leu Asp Pro Ala Asp Arg Tyr Leu Thr
                325                 330                 335

Glu Gln Cys Leu Asn His Pro Thr Phe Gln Thr Gln Arg Leu Leu Asp
            340                 345                 350

Arg Ser Pro Ser Arg Ser Ala Lys Arg Lys Pro Tyr His Val Glu Ser
        355                 360                 365
```

```
Ser Thr Leu Ser Asn Arg Asn Gln Ala Gly Lys Ser Thr Ala Leu Gln
    370                 375                 380

Ser His His Arg Ser Asn Ser Lys Asp Ile Gln Asn Leu Ser Val Gly
385                 390                 395                 400

Leu Pro Arg Ala Asp Glu Gly Leu Pro Ala Asn Glu Ser Phe Leu Asn
                405                 410                 415

Gly Asn Leu Ala Gly Ala Ser Leu Ser Pro Leu His Thr Lys Thr Tyr
                420                 425                 430

Gln Ala Ser Ser Gln Pro Gly Ser Thr Ser Lys Asp Leu Thr Asn Asn
            435                 440                 445

Asn Ile Pro His Leu Leu Ser Pro Lys Glu Ala Lys Ser Lys Thr Glu
    450                 455                 460

Phe Asp Phe Asn Ile Asp Pro Lys Pro Ser Glu Gly Pro Gly Thr Lys
465                 470                 475                 480

Tyr Leu Lys Ser Asn Ser Arg Ser Gln Gln Asn Arg His Ser Phe Met
                485                 490                 495

Glu Ser Ser Gln Ser Lys Ala Gly Thr Leu Gln Pro Asn Glu Lys Gln
            500                 505                 510

Ser Arg His Ser Tyr Ile Asp Thr Ile Pro Gln Ser Ser Arg Ser Pro
    515                 520                 525

Ser Tyr Arg Thr Lys Ala Lys Ser His Gly Ala Leu Ser Asp Ser Lys
    530                 535                 540

Ser Val Ser Asn Leu Ser Glu Ala Arg Ala Gln Ile Ala Glu Pro Ser
545                 550                 555                 560

Thr Ser Arg Tyr Phe Pro Ser Ser Cys Leu Asp Leu Asn Ser Pro Thr
                565                 570                 575

Ser Pro Thr Pro Thr Arg His Ser Asp Thr Arg Thr Leu Leu Ser Pro
            580                 585                 590

Ser Gly Arg Asn Asn Arg Asn Glu Gly Thr Leu Asp Ser Arg Arg Thr
    595                 600                 605

Thr Thr Arg His Ser Lys Thr Met Glu Glu Leu Lys Leu Pro Glu His
    610                 615                 620

Met Asp Ser Ser His Ser His Ser Leu Ser Ala Pro His Glu Ser Phe
625                 630                 635                 640

Ser Tyr Gly Leu Gly Tyr Thr Ser Pro Phe Ser Ser Gln Gln Arg Pro
                645                 650                 655

His Arg His Ser Met Tyr Val Thr Arg Asp Lys Val Arg Ala Lys Gly
            660                 665                 670

Leu Asp Gly Ser Leu Ser Ile Gly Gln Gly Met Ala Ala Arg Ala Asn
    675                 680                 685

Ser Leu Gln Leu Leu Ser Pro Gln Pro Gly Glu Gln Leu Pro Pro Glu
    690                 695                 700

Met Thr Val Ala Arg Ser Ser Val Lys Glu Thr Ser Arg Glu Gly Thr
705                 710                 715                 720

Ser Ser Phe His Thr Arg Gln Lys Ser Glu Gly Gly Val Tyr His Asp
                725                 730                 735

Pro His Ser Asp Asp Gly Thr Ala Pro Lys Glu Asn Arg His Leu Tyr
            740                 745                 750

Asn Asp Pro Val Pro Arg Arg Val Gly Ser Phe Tyr Arg Val Pro Ser
    755                 760                 765

Pro Arg Pro Asp Asn Ser Phe His Glu Asn Asn Val Ser Thr Arg Val
    770                 775                 780

Ser Ser Leu Pro Ser Glu Ser Ser Ser Gly Thr Asn His Ser Lys Arg
```

```
                785                 790                 795                 800
Gln Pro Ala Phe Asp Pro Trp Lys Ser Pro Glu Asn Ile Ser His Ser
                    805                 810                 815
Glu Gln Leu Lys Glu Lys Glu Lys Gln Gly Phe Phe Arg Ser Met Lys
                820                 825                 830
Lys Lys Lys Lys Lys Ser Gln Thr Val Pro Asn Ser Asp Ser Pro Asp
                835                 840                 845
Leu Leu Thr Leu Gln Lys Ser Ile His Ser Ala Ser Thr Pro Ser Ser
    850                 855                 860
Arg Pro Lys Glu Trp Arg Pro Glu Lys Ile Ser Asp Leu Gln Thr Gln
865                 870                 875                 880
Ser Gln Pro Leu Lys Ser Leu Arg Lys Leu Leu His Leu Ser Ala
                    885                 890                 895
Ser Asn His Pro Ala Ser Ser Asp Pro Arg Phe Gln Pro Leu Thr Ala
                900                 905                 910
Gln Gln Thr Lys Asn Ser Phe Ser Glu Ile Arg Ile His Pro Leu Ser
                915                 920                 925
Gln Ala Ser Gly Gly Ser Ser Asn Ile Arg Gln Glu Pro Ala Pro Lys
    930                 935                 940
Gly Arg Pro Ala Leu Gln Leu Pro Asp Gly Gly Cys Asp Gly Arg Arg
945                 950                 955                 960
Gln Arg His His Ser Gly Pro Gln Asp Arg Arg Phe Met Leu Arg Thr
                    965                 970                 975
Thr Glu Gln Gln Gly Glu Tyr Phe Cys Cys Gly Asp Pro Lys Lys Pro
                980                 985                 990
His Thr Pro Cys Val Pro Asn Arg  Ala Leu His Arg Pro  Ile Ser Ser
                995                 1000                1005
Pro Ala  Pro Tyr Pro Val Leu  Gln Val Arg Gly  Thr Ser Met Cys
    1010                1015                1020
Pro Thr  Leu Gln Val Arg Gly  Thr Asp Ala Phe  Ser Cys Pro Thr
    1025                1030                1035
Gln Gln  Ser Gly Phe Ser Phe  Phe Val Arg His Val  Met Arg Glu
    1040                1045                1050
Ala Leu  Ile His Arg Ala Gln  Val Asn Gln Ala  Leu Leu Thr
    1055                1060                1065
Tyr His  Glu Asn Ala Ala Leu  Thr Gly Lys Ser Ala  Arg Gly Gly
    1070                1075                1080
Pro Glu  Gln Lys Leu Ile Ser  Glu Glu Asp Leu  Asn Ser Ala Val
    1085                1090                1095
Asp His  His His His His
    1100                1105

<210> SEQ ID NO 9
<211> LENGTH: 4068
<212> TYPE: DNA
<213> ORGANISM: Artificial Sequence
<220> FEATURE:
<223> OTHER INFORMATION: TATK-CDKL5 fusion protein cDNA

<400> SEQUENCE: 9
gctagccacc atggagacag acacactcct gctatgggta ctgctgctct gggttccagg      60
ttccactggt gacgcggccc agccggccag gcgcgcgcgc cgtacgaagc ttgcggccta     120
cgccagaaag gccgccaggc aggccagggc acgtcgccca ccatggtgag caagggcgag     180
gagctgttca ccggggtggt gcccatcctg gtcgagctgg acggcgacgt aaacggccac     240
```

-continued

```
aagttcagcg tgtccggcga gggcgagggc gatgccacct acggcaagct gaccctgaag    300
ttcatctgca ccaccggcaa gctgcccgtg ccctggccca ccctcgtgac caccctgacc    360
tacggcgtgc agtgcttcag ccgctacccc gaccacatga agcagcacga cttcttcaag    420
tccgccatgc ccgaaggcta cgtccaggag cgcaccatct tcttcaagga cgacggcaac    480
tacaagaccc gcgccgaggt gaagttcgag ggcgacaccc tggtgaaccg catcgagctg    540
aagggcatcg acttcaagga ggacggcaac atcctgggc acaagctgga gtacaactac    600
aacagccaca acgtctatat catggccgac aagcagaaga cggcatcaa ggtgaacttc    660
aagatccgcc acaacatcga ggacggcagc gtgcagctcg ccgaccacta ccagcagaac    720
acccccatcg gcgacggccc cgtgctgctg cccgacaacc actacctgag cacccagtcc    780
gccctgagca agacccccaa cgagaagcgc gatcacatgg tcctgctgga gttcgtgacc    840
gccgccggga tcactctcgg catggacgag ctgtacaagt ccggactcag atctcgagcg    900
aagattccta acattggtaa tgtgatgaat aaatttgaga tccttggggt tgtaggtgaa    960
ggagcctatg gagttgtact taaatgcaga cacaaggaaa cacatgaaat tgtggcgatc    1020
aagaaattca aggacagtga agaaaatgaa gaagtcaaag aaacgacttt acgagagctt    1080
aaaatgcttc ggactctcaa gcaggaaaac attgtggagt tgaaggaagc atttcgtcgg    1140
aggggaaagt tgtacttggt gtttgagtat gttgaaaaaa atatgctcga attgctggaa    1200
gaaatgccaa atggagttcc acctgagaaa gtaaaaagct acatctatca gctaatcaag    1260
gctattcact ggtgcctaag aatgatattg tccatcgaga tataaaacca gaaaatctct    1320
taatcagcca caatgatgtc ctaaaactgt gtgactttgg ttttgctcgt aatctgtcag    1380
aaggcaataa tgctaattac acagagtacg ttgccaccag atggtatcgg tccccagaac    1440
tcttacttgg cgctccctat ggaaagtccg tggacatgtg gtcggtgggc tgtattcttg    1500
gggagcttag cgatggacag cctttatttc ctggagaaag tgaaattgac caactttta    1560
ctattcagaa ggtgctagga ccacttccat ctgagcagat gaagcttttc tacagtaatc    1620
ctcgcttcca tgggctccgg tttccagctg ttaaccatcc tcagtccttg gaaagaagat    1680
accttggaat tttgaatagt gttctacttg acctaatgaa gaatttactg aagttggacc    1740
cagctgacag atacttgaca gaacagtgtt tgaatcaccc tacatttcaa acccagagac    1800
ttctggatcg ttctccttca aggtcagcaa aaagaaaacc ttaccatgtg gaaagcagca    1860
cattgtctaa tagaaaccaa gccggcaaaa gtactgcttt gcagtctcac cacagatcta    1920
acagcaagga catccagaac ctgagtgtag gcctgccccg ggctgacgaa ggtctccctg    1980
ccaatgaaag cttcctaaat ggaaaccttg ctggagctag tcttagtcca ctgcacacca    2040
aaacctacca agcaagcagc cagcctgggt ctaccagcaa agatctcacc aacaacaaca    2100
taccacacct tcttagccca aaagaagcca agtcaaaaac agagtttgat tttaatattg    2160
acccaaagcc ttcagaaggc ccagggacaa agtacctcaa gtcaaacagc agatctcagc    2220
agaaccgcca ctcattcatg gaaagctctc aaagcaaagc tgggacactg cagcccaatg    2280
aaaagcagag tcggcatagc tatattgaca caattcccca gtcctctagg agtccctcct    2340
acaggaccaa ggccaaaagc catggggcac tgagtgactc caagtctgtg agcaaccttt    2400
ctgaagccag ggcccaaatt gcggagccca gtaccagtag gtacttccca tctagctgct    2460
tagacttgaa ttctcccacc agcccaaccc ccaccagaca cagtgacacg agaactttgc    2520
tcagcccttc tggaagaaat aaccgaaatg agggaacgct ggactcacgt cgaaccacaa    2580
```

```
ccagacattc taagacgatg gaggaattga agctgccgga gcacatggac agtagccatt    2640
cccattcact gtctgcacct cacgaatctt tttcttatgg actgggctac accagccccc    2700
tttcttccca gcaacgtcct cataggcatt ctatgtatgt gacccgtgac aaagtgagag    2760
ccaagggctt ggatggaagc ttgagcatag gcaagggat ggcagctaga gccaacagcc     2820
tgcaactctt gtcaccccag cctggagaac agctccctcc agagatgact gtggcaagat    2880
cttcggtcaa agagacctcc agagaaggca cctcttcctt ccatacacgc agaagtctg     2940
agggtggagt gtatcatgac ccacactctg atgatggcac agcccccaaa gaaaatagac    3000
acctatacaa tgatcctgtg ccaaggagag ttggtagctt ttacagagtg ccatctccac    3060
gtccagacaa ttcttttccat gaaaataatg tgtcaactag agtttcttct ctaccatcag   3120
agagcagttc tggaaccaac cactcaaaaa gacaaccagc attcgatcca tggaaaagtc    3180
ctgaaaatat tagtcattca gagcaactca aggaaaaaga gaagcaagga ttttcaggt    3240
caatgaaaaa gaaaagaag aaatctcaaa cagtacccaa ttccgacagc cctgatcttc     3300
tgacgttgca gaaatccatt cattctgcta gcactccaag cagcagacca aaggagtggc    3360
gccccggaag atctcagatc tgcagaccca agccagcca ttaaaatcac tgcgcaagtt     3420
gttacatctc tcttcggcct caaatcaccc ggcttcctca gtcccgcgtt ccagccctta    3480
acagctcaac aaaccaaaaa ttccttctca gaaattcgga ttcacccct gagccaggcc     3540
tctggcggga gcagcaacat ccggcaggaa cccgcaccga agggcaggcc agccctccag    3600
ctgccagacg tggatgtga tggcagaaga cagagacacc attctggacc caagataga    3660
cgcttcatgt taaggacgac agaacaacaa ggagaatact tctgctgtgg tgacccaaag    3720
aagcctcaca ctccgtgcgt cccaaaccga gcccttcatc gtccaatctc cagtcctgct    3780
ccctatccag tactccaggt ccgaggcact tccatgtgcc cgacactcca ggtccgaggc    3840
actgatgctt tcagctgccc aacccagcaa tccgggttct cttcttcgt gagacacgtt     3900
atgagggaag ccctgattca cagggcccag gtaaaccaag ctgcgctcct gacataccat    3960
gagaatgcgg cactgacggg caagtccgct cgaggagggc ccgaacaaaa actcatctca    4020
gaagaggatc tgaatagcgc cgtcgaccat catcatcatc atcattga                 4068
```

<210> SEQ ID NO 10
<211> LENGTH: 1353
<212> TYPE: PRT
<213> ORGANISM: Artificial Sequence
<220> FEATURE:
<223> OTHER INFORMATION: TATk-CDKL5 fusion protein polypeptide

<400> SEQUENCE: 10

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Ala Ala Tyr Ala Arg Lys Ala Ala Arg Gln Ala Arg Ala Pro
        35                  40                  45

Val Ala Thr Met Val Ser Lys Gly Glu Glu Leu Phe Thr Gly Val Val
    50                  55                  60

Pro Ile Leu Val Glu Leu Asp Gly Asp Val Asn Gly His Lys Phe Ser
65                  70                  75                  80

Val Ser Gly Glu Gly Glu Gly Asp Ala Thr Tyr Gly Lys Leu Thr Leu
                85                  90                  95

Lys Phe Ile Cys Thr Thr Gly Lys Leu Pro Val Pro Trp Pro Thr Leu
```

-continued

```
            100                 105                 110
Val Thr Thr Leu Thr Tyr Gly Val Gln Cys Phe Ser Arg Tyr Pro Asp
            115                 120                 125
His Met Lys Gln His Asp Phe Phe Lys Ser Ala Met Pro Glu Gly Tyr
            130                 135             140
Val Gln Glu Arg Thr Ile Phe Phe Lys Asp Asp Gly Asn Tyr Lys Thr
145                 150                 155                 160
Arg Ala Glu Val Lys Phe Glu Gly Asp Thr Leu Val Asn Arg Ile Glu
                165                 170                 175
Leu Lys Gly Ile Asp Phe Lys Glu Asp Gly Asn Ile Leu Gly His Lys
                180                 185                 190
Leu Glu Tyr Asn Tyr Asn Ser His Asn Val Tyr Ile Met Ala Asp Lys
                195                 200                 205
Gln Lys Asn Gly Ile Lys Val Asn Phe Lys Ile Arg His Asn Ile Glu
                210                 215                 220
Asp Gly Ser Val Gln Leu Ala Asp His Tyr Gln Gln Asn Thr Pro Ile
225                 230                 235                 240
Gly Asp Gly Pro Val Leu Leu Pro Asp Asn His Tyr Leu Ser Thr Gln
                245                 250                 255
Ser Ala Leu Ser Lys Asp Pro Asn Glu Lys Arg Asp His Met Val Leu
                260                 265                 270
Leu Glu Phe Val Thr Ala Ala Gly Ile Thr Leu Gly Met Asp Glu Leu
                275                 280                 285
Tyr Lys Ser Gly Leu Arg Ser Arg Ala Lys Ile Pro Asn Ile Gly Asn
                290                 295                 300
Val Met Asn Lys Phe Glu Ile Leu Gly Val Val Gly Glu Gly Ala Tyr
305                 310                 315                 320
Gly Val Val Leu Lys Cys Arg His Lys Glu Thr His Glu Ile Val Ala
                325                 330                 335
Ile Lys Lys Phe Lys Asp Ser Glu Glu Asn Glu Glu Val Lys Glu Thr
                340                 345                 350
Thr Leu Arg Glu Leu Lys Met Leu Arg Thr Leu Lys Gln Glu Asn Ile
                355                 360                 365
Val Glu Leu Lys Glu Ala Phe Arg Arg Arg Gly Lys Leu Tyr Leu Val
                370                 375             380
Phe Glu Tyr Val Glu Lys Asn Met Leu Glu Leu Leu Glu Glu Met Pro
385                 390                 395                 400
Asn Gly Val Pro Pro Glu Lys Val Lys Ser Tyr Ile Tyr Gln Leu Ile
                405                 410                 415
Lys Ala Ile His Trp Cys His Lys Asn Asp Ile Val His Arg Asp Ile
                420                 425                 430
Lys Pro Glu Asn Leu Leu Ile Ser His Asn Asp Val Leu Lys Leu Cys
                435                 440                 445
Asp Phe Gly Phe Ala Arg Asn Leu Ser Glu Gly Asn Asn Ala Asn Tyr
                450                 455             460
Thr Glu Tyr Val Ala Thr Arg Trp Tyr Arg Ser Pro Glu Leu Leu Leu
465                 470                 475                 480
Gly Ala Pro Tyr Gly Lys Ser Val Asp Met Trp Ser Val Gly Cys Ile
                485                 490                 495
Leu Gly Glu Leu Ser Asp Gly Gln Pro Leu Phe Pro Gly Glu Ser Glu
                500                 505                 510
Ile Asp Gln Leu Phe Thr Ile Gln Lys Val Leu Gly Pro Leu Pro Ser
                515                 520                 525
```

```
Glu Gln Met Lys Leu Phe Tyr Ser Asn Pro Arg Phe His Gly Leu Arg
    530                 535                 540

Phe Pro Ala Val Asn His Pro Gln Ser Leu Glu Arg Arg Tyr Leu Gly
545                 550                 555                 560

Ile Leu Asn Ser Val Leu Leu Asp Leu Met Lys Asn Leu Leu Lys Leu
                565                 570                 575

Asp Pro Ala Asp Arg Tyr Leu Thr Glu Gln Cys Leu Asn His Pro Thr
            580                 585                 590

Phe Gln Thr Gln Arg Leu Leu Asp Arg Ser Pro Ser Arg Ser Ala Lys
        595                 600                 605

Arg Lys Pro Tyr His Val Glu Ser Ser Thr Leu Ser Asn Arg Asn Gln
    610                 615                 620

Ala Gly Lys Ser Thr Ala Leu Gln Ser His His Arg Ser Asn Ser Lys
625                 630                 635                 640

Asp Ile Gln Asn Leu Ser Val Gly Leu Pro Arg Ala Asp Glu Gly Leu
                645                 650                 655

Pro Ala Asn Glu Ser Phe Leu Asn Gly Asn Leu Ala Gly Ala Ser Leu
            660                 665                 670

Ser Pro Leu His Thr Lys Thr Tyr Gln Ala Ser Ser Gln Pro Gly Ser
        675                 680                 685

Thr Ser Lys Asp Leu Thr Asn Asn Asn Ile Pro His Leu Leu Ser Pro
    690                 695                 700

Lys Glu Ala Lys Ser Lys Thr Glu Phe Asp Phe Asn Ile Asp Pro Lys
705                 710                 715                 720

Pro Ser Glu Gly Pro Gly Thr Lys Tyr Leu Lys Ser Asn Ser Arg Ser
                725                 730                 735

Gln Gln Asn Arg His Ser Phe Met Glu Ser Ser Gln Ser Lys Ala Gly
            740                 745                 750

Thr Leu Gln Pro Asn Glu Lys Gln Ser Arg His Ser Tyr Ile Asp Thr
        755                 760                 765

Ile Pro Gln Ser Ser Arg Ser Pro Ser Tyr Arg Thr Lys Ala Lys Ser
    770                 775                 780

His Gly Ala Leu Ser Asp Ser Lys Ser Val Ser Asn Leu Ser Glu Ala
785                 790                 795                 800

Arg Ala Gln Ile Ala Glu Pro Ser Thr Ser Arg Tyr Phe Pro Ser Ser
                805                 810                 815

Cys Leu Asp Leu Asn Ser Pro Thr Ser Pro Thr Pro Thr Arg His Ser
            820                 825                 830

Asp Thr Arg Thr Leu Leu Ser Pro Ser Gly Arg Asn Asn Arg Asn Glu
        835                 840                 845

Gly Thr Leu Asp Ser Arg Arg Thr Thr Thr Arg His Ser Lys Thr Met
    850                 855                 860

Glu Glu Leu Lys Leu Pro Glu His Met Asp Ser Ser His Ser His Ser
865                 870                 875                 880

Leu Ser Ala Pro His Glu Ser Phe Ser Tyr Gly Leu Gly Tyr Thr Ser
                885                 890                 895

Pro Phe Ser Ser Gln Gln Arg Pro His Arg His Ser Met Tyr Val Thr
            900                 905                 910

Arg Asp Lys Val Arg Ala Lys Gly Leu Asp Gly Ser Leu Ser Ile Gly
        915                 920                 925

Gln Gly Met Ala Ala Arg Ala Asn Ser Leu Gln Leu Leu Ser Pro Gln
    930                 935                 940
```

```
Pro Gly Glu Gln Leu Pro Pro Glu Met Thr Val Ala Arg Ser Ser Val
945                 950                 955                 960

Lys Glu Thr Ser Arg Glu Gly Thr Ser Ser Phe His Thr Arg Gln Lys
            965                 970                 975

Ser Glu Gly Gly Val Tyr His Asp Pro His Ser Asp Asp Gly Thr Ala
            980                 985                 990

Pro Lys Glu Asn Arg His Leu Tyr Asn Asp Pro Val Pro Arg Arg Val
        995                 1000                1005

Gly Ser Phe Tyr Arg Val Pro Ser Pro Arg Pro Asp Asn Ser Phe
    1010                1015                1020

His Glu Asn Asn Val Ser Thr Arg Val Ser Ser Leu Pro Ser Glu
    1025                1030                1035

Ser Ser Ser Gly Thr Asn His Ser Lys Arg Gln Pro Ala Phe Asp
    1040                1045                1050

Pro Trp Lys Ser Pro Glu Asn Ile Ser His Ser Glu Gln Leu Lys
    1055                1060                1065

Glu Lys Glu Lys Gln Gly Phe Phe Arg Ser Met Lys Lys Lys
    1070                1075                1080

Lys Lys Ser Gln Thr Val Pro Asn Ser Asp Ser Pro Asp Leu Leu
    1085                1090                1095

Thr Leu Gln Lys Ser Ile His Ser Ala Ser Thr Pro Ser Ser Arg
    1100                1105                1110

Pro Lys Glu Trp Arg Pro Glu Lys Ile Ser Asp Leu Gln Thr Gln
    1115                1120                1125

Ser Gln Pro Leu Lys Ser Leu Arg Lys Leu Leu His Leu Ser Ser
    1130                1135                1140

Ala Ser Asn His Pro Ala Ser Asp Pro Arg Phe Gln Pro Leu
    1145                1150                1155

Thr Ala Gln Gln Thr Lys Asn Ser Phe Ser Glu Ile Arg Ile His
    1160                1165                1170

Pro Leu Ser Gln Ala Ser Gly Gly Ser Ser Asn Ile Arg Gln Glu
    1175                1180                1185

Pro Ala Pro Lys Gly Arg Pro Ala Leu Gln Leu Pro Asp Gly Gly
    1190                1195                1200

Cys Asp Gly Arg Arg Gln Arg His His Ser Gly Pro Gln Asp Arg
    1205                1210                1215

Arg Phe Met Leu Arg Thr Thr Glu Gln Gln Gly Glu Tyr Phe Cys
    1220                1225                1230

Cys Gly Asp Pro Lys Lys Pro His Thr Pro Cys Val Pro Asn Arg
    1235                1240                1245

Ala Leu His Arg Pro Ile Ser Ser Pro Ala Pro Tyr Pro Val Leu
    1250                1255                1260

Gln Val Arg Gly Thr Ser Met Cys Pro Thr Leu Gln Val Arg Gly
    1265                1270                1275

Thr Asp Ala Phe Ser Cys Pro Thr Gln Gln Ser Gly Phe Ser Phe
    1280                1285                1290

Phe Val Arg His Val Met Arg Glu Ala Leu Ile His Arg Ala Gln
    1295                1300                1305

Val Asn Gln Ala Ala Leu Leu Thr Tyr His Glu Asn Ala Ala Leu
    1310                1315                1320

Thr Gly Lys Ser Ala Arg Gly Gly Pro Glu Gln Lys Leu Ile Ser
    1325                1330                1335

Glu Glu Asp Leu Asn Ser Ala Val Asp His His His His His His
```

<210> SEQ ID NO 11
<211> LENGTH: 3852
<212> TYPE: DNA
<213> ORGANISM: Artificial Sequence
<220> FEATURE:
<223> OTHER INFORMATION: TATk-CDKL5 Fusion protein cDNA

<400> SEQUENCE: 11

```
atggagacag acacactcct gctatgggta ctgctgctct gggttccagg ttccactggt      60
gacgcggccc agccggccag gcgcgcgcgc cgtacgaagc ttgcggccta cgccagaaag     120
gccgccaggc aggccagggc accggtcgcc accatggtga gcaagggcga ggagctgttc     180
accggggtgg tgcccatcct ggtcgagctg gacggcgacg taaacggcca caagttcagc     240
gtgtccggcg agggcgaggg cgatgccacc tacggcaagc tgaccctgaa gttcatctgc     300
accaccggca agctgcccgt gccctggccc accctcgtga ccaccctgac ctacggcgtg     360
cagtgcttca gccgctaccc cgaccacatg aagcagcacg acttcttcaa gtccgccatg     420
cccgaaggct acgtccagga gcgcaccatc ttcttcaagg acgacggcaa ctacaagacc     480
cgcgccgagg tgaagttcga gggcgacacc ctggtgaacc gcatcgagct gaagggcatc     540
gacttcaagg aggacggcaa catcctgggg cacaagctgg agtacaacta caacagccac     600
aacgtctata tcatggccga caagcagaag aacggcatca aggtgaactt caagatccgc     660
cacaacatcg aggacggcag cgtgcagctc gccgaccact accagcagaa cacccccatc     720
ggcgacggcc ccgtgctgct gcccgacaac cactacctga gcacccagtc cgccctgagc     780
aaagacccca acgagaagcg cgatcacatg gtcctgctgg agttcgtgac cgccgccggg     840
atcactctcg gcatggacga gctgtacaag tccggactca gatctcgagc gaagattcct     900
aacattggta atgtgatgaa taaatttgag atccttgggg ttgtaggtga aggagcctat     960
ggagttgtac ttaaatgcag acacaaggaa acacatgaaa ttgtggcgat caagaaattc    1020
aaggacagtg aagaaaatga agaagtcaaa gaaacgactt tacgagagct taaaatgctt    1080
cggactctca gcaggaaaaa cattgtggag ttgaaggaag catttcgtcg aggggggaag    1140
ttgtacttgg tgtttgagta tgttgaaaaa aatatgctcg aattgctgga gaaatgccca    1200
aatggagttc cacctgagaa agtaaaaagc tacatctatc agctaatcaa ggctattcac    1260
tggtgccata agaatgatat tgtccatcga gatataaaac agaaaatctc ttaatcagc    1320
cacaatgatg tcctaaaact gtgtgacttt ggttttgctc gtaatctgtc agaaggcaat    1380
aatgctaatt acacagagta cgttgccacc agatggtatc ggtccccaga actcttactt    1440
ggcgctccct atgaaagtc cgtggacatg tggtcggtgg ctgtattct ggggagctt      1500
agcgatggac agccttatat tcctggagaa agtgaaattg accaactttt tactattcag    1560
aaggtgctag gaccacttcc atctgagcag atgaagcttt tctacagtaa tcctcgcttc    1620
catgggctcc ggtttccagc tgttaaccat cctcagtcct tggaaagaag ataccttgga    1680
atttttgaata gtgttctact tgacctaatg aagaatttac tgaagttgga cccagctgac    1740
agatacttga cagaacagtg tttgaatcac cctacatttc aaacccagag acttctggat    1800
cgttctcctt caaggtcagc aaaaagaaaa ccttaccatg tggaaagcag cacattgtct    1860
aatagaaacc aagccggcaa agtactgctt tgcagtctc accacagatc taacagcaag    1920
gacatccaga acctgagtgt aggcctgccc cgggctgacg aaggtctccc tgccaatgaa    1980
agcttcctaa atgaaaacct tgctggagct agtcttagtc cactgcacac caaaacctac    2040
```

-continued

```
caagcaagca gccagcctgg gtctaccagc aaagatctca ccaacaacaa cataccacac    2100
cttcttagcc caaaagaagc caagtcaaaa acagagtttg attttaatat tgacccaaag    2160
ccttcagaag gcccagggac aaagtacctc aagtcaaaca gcagatctca gcagaaccgc    2220
cactcattca tggaaagctc tcaaagcaaa gctgggacac tgcagcccaa tgaaaagcag    2280
agtcggcata gctatattga cacaattccc cagtcctcta ggagtccctc ctacaggacc    2340
aaggccaaaa gccatggggc actgagtgac tccaagtctg tgagcaacct ttctgaagcc    2400
agggcccaaa ttgcggagcc cagtaccagt aggtacttcc catctagctg cttagacttg    2460
aattctccca ccagcccaac ccccaccaga cacagtgaca cgagaacttt gctcagccct    2520
tctggaagaa ataaccgaaa tgagggaacg ctggactcac gtcgaaccac aaccagacat    2580
tctaagacga tggaggaatt gaagctgccg gagcacatgg acagtagcca ttcccattca    2640
ctgtctgcac ctcacgaatc ttttcttat ggactgggct acaccagccc cttttcttcc     2700
cagcaacgtc ctcataggca ttctatgtat gtgacccgtg acaaagtgag agccaagggc    2760
ttggatggaa gcttgagcat agggcaaggg atggcagcta gagccaacag cctgcaactc    2820
ttgtcacccc agcctggaga acagctccct ccagagatga ctgtggcaag atcttcggtc    2880
aaagagacct ccagagaagg cacctcttcc ttccatacac gccagaagtc tgagggtgga    2940
gtgtatcatg acccacactc tgatgatggc acagccccca agaaaatag acacctatac     3000 aatgatcctg tgccaaggag agttggtagc ttttacagag tgccatctcc acgtccagac    3060
aattctttcc atgaaaataa tgtgtcaact agagtttctt ctctaccatc agagagcagt    3120
tctggaacca accactcaaa aagacaacca gcattcgatc catggaaaag tcctgaaaat    3180
attagtcatt cagagcaact caaggaaaaa gagaagcaag attttttcag gtcaatgaaa    3240
aagaaaaaga agaaatctca aacagtaccc aattccgaca gccctgatct tctgacgttg    3300
cagaaatcca ttcattctgc tagcactcca agcagcagac caaggagtg gcgccccgag    3360 aagatctcag atctgcagac ccaaagccag ccattaaaat cactgcgcaa gttgttacat    3420
ctctcttcgg cctcaaatca cccggcttcc tcagatcccc gcttccagcc cttaacagct    3480
caacaaacca aaaattcctt ctcagaaatt cggattcacc ccctgagcca ggcctctggc    3540
gggagcagca acatccggca ggaacccgca ccgaagggca ggccagccct ccagctgcca    3600
ggtcagatgg atcctggttg gcatgtgtcc tctgtgacca ggagtgccac agagggccct    3660
tcctactctg aacagctggg tgccaaaagt gggccaaatg gcacccctaa tacagaaca    3720 aatcgctcac gaatgccaaa tctgaatgat ttaaaagaga cagccttgtc cgctcgagga    3780
gggcccgaac aaaaactcat ctcagaagag gatctgaata gcgccgtcga ccatcatcat    3840
catcatcatt ga                                                        3852
```

<210> SEQ ID NO 12
<211> LENGTH: 1283
<212> TYPE: PRT
<213> ORGANISM: Artificial Sequence
<220> FEATURE:
<223> OTHER INFORMATION: TATk-CDKL5 Fusion protein polypeptide

<400> SEQUENCE: 12

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30
```

```
Lys Leu Ala Ala Tyr Ala Arg Lys Ala Ala Arg Gln Ala Arg Ala Pro
         35                  40                  45

Val Ala Thr Met Val Ser Lys Gly Glu Glu Leu Phe Thr Gly Val Val
 50                  55                  60

Pro Ile Leu Val Glu Leu Asp Gly Asp Val Asn Gly His Lys Phe Ser
 65                  70                  75                  80

Val Ser Gly Glu Gly Glu Gly Asp Ala Thr Tyr Gly Lys Leu Thr Leu
                 85                  90                  95

Lys Phe Ile Cys Thr Thr Gly Lys Leu Pro Val Pro Trp Pro Thr Leu
                100                 105                 110

Val Thr Thr Leu Thr Tyr Gly Val Gln Cys Phe Ser Arg Tyr Pro Asp
                115                 120                 125

His Met Lys Gln His Asp Phe Phe Lys Ser Ala Met Pro Glu Gly Tyr
        130                 135                 140

Val Gln Glu Arg Thr Ile Phe Phe Lys Asp Asp Gly Asn Tyr Lys Thr
145                 150                 155                 160

Arg Ala Glu Val Lys Phe Glu Gly Asp Thr Leu Val Asn Arg Ile Glu
                165                 170                 175

Leu Lys Gly Ile Asp Phe Lys Glu Asp Gly Asn Ile Leu Gly His Lys
                180                 185                 190

Leu Glu Tyr Asn Tyr Asn Ser His Asn Val Tyr Ile Met Ala Asp Lys
        195                 200                 205

Gln Lys Asn Gly Ile Lys Val Asn Phe Lys Ile Arg His Asn Ile Glu
        210                 215                 220

Asp Gly Ser Val Gln Leu Ala Asp His Tyr Gln Gln Asn Thr Pro Ile
225                 230                 235                 240

Gly Asp Gly Pro Val Leu Leu Pro Asp Asn His Tyr Leu Ser Thr Gln
                245                 250                 255

Ser Ala Leu Ser Lys Asp Pro Asn Glu Lys Arg Asp His Met Val Leu
                260                 265                 270

Leu Glu Phe Val Thr Ala Ala Gly Ile Thr Leu Gly Met Asp Glu Leu
        275                 280                 285

Tyr Lys Ser Gly Leu Arg Ser Arg Ala Lys Ile Pro Asn Ile Gly Asn
        290                 295                 300

Val Met Asn Lys Phe Glu Ile Leu Gly Val Val Gly Glu Gly Ala Tyr
305                 310                 315                 320

Gly Val Val Leu Lys Cys Arg His Lys Glu Thr His Glu Ile Val Ala
                325                 330                 335

Ile Lys Lys Phe Lys Asp Ser Glu Glu Asn Glu Glu Val Lys Glu Thr
                340                 345                 350

Thr Leu Arg Glu Leu Lys Met Leu Arg Thr Leu Lys Gln Glu Asn Ile
        355                 360                 365

Val Glu Leu Lys Glu Ala Phe Arg Arg Gly Lys Leu Tyr Leu Val
        370                 375                 380

Phe Glu Tyr Val Glu Lys Asn Met Leu Glu Leu Leu Glu Glu Met Pro
385                 390                 395                 400

Asn Gly Val Pro Pro Glu Lys Val Lys Ser Tyr Ile Tyr Gln Leu Ile
                405                 410                 415

Lys Ala Ile His Trp Cys His Lys Asn Asp Ile Val His Arg Asp Ile
                420                 425                 430

Lys Pro Glu Asn Leu Leu Ile Ser His Asn Asp Val Leu Lys Leu Cys
        435                 440                 445

Asp Phe Gly Phe Ala Arg Asn Leu Ser Glu Gly Asn Asn Ala Asn Tyr
```

```
                450             455             460
Thr Glu Tyr Val Ala Thr Arg Trp Tyr Arg Ser Pro Glu Leu Leu Leu
465                 470             475                 480

Gly Ala Pro Tyr Gly Lys Ser Val Asp Met Trp Ser Val Gly Cys Ile
                    485             490                 495

Leu Gly Glu Leu Ser Asp Gly Gln Pro Leu Phe Pro Gly Glu Ser Glu
                500             505             510

Ile Asp Gln Leu Phe Thr Ile Gln Lys Val Leu Gly Pro Leu Pro Ser
            515             520             525

Glu Gln Met Lys Leu Phe Tyr Ser Asn Pro Arg Phe His Gly Leu Arg
        530             535             540

Phe Pro Ala Val Asn His Pro Gln Ser Leu Glu Arg Arg Tyr Leu Gly
545             550             555             560

Ile Leu Asn Ser Val Leu Leu Asp Leu Met Lys Asn Leu Leu Lys Leu
                565             570             575

Asp Pro Ala Asp Arg Tyr Leu Thr Glu Gln Cys Leu Asn His Pro Thr
            580             585             590

Phe Gln Thr Gln Arg Leu Leu Asp Arg Ser Pro Ser Arg Ser Ala Lys
        595             600             605

Arg Lys Pro Tyr His Val Glu Ser Ser Thr Leu Ser Asn Arg Asn Gln
610             615             620

Ala Gly Lys Ser Thr Ala Leu Gln Ser His His Arg Ser Asn Ser Lys
625             630             635             640

Asp Ile Gln Asn Leu Ser Val Gly Leu Pro Arg Ala Asp Glu Gly Leu
                645             650             655

Pro Ala Asn Glu Ser Phe Leu Asn Gly Asn Leu Ala Gly Ala Ser Leu
            660             665             670

Ser Pro Leu His Thr Lys Thr Tyr Gln Ala Ser Ser Gln Pro Gly Ser
        675             680             685

Thr Ser Lys Asp Leu Thr Asn Asn Asn Ile Pro His Leu Leu Ser Pro
690             695             700

Lys Glu Ala Lys Ser Lys Thr Glu Phe Asp Phe Asn Ile Asp Pro Lys
705             710             715             720

Pro Ser Glu Gly Pro Gly Thr Lys Tyr Leu Lys Ser Asn Ser Arg Ser
                725             730             735

Gln Gln Asn Arg His Ser Phe Met Glu Ser Ser Gln Ser Lys Ala Gly
            740             745             750

Thr Leu Gln Pro Asn Glu Lys Gln Ser Arg His Ser Tyr Ile Asp Thr
        755             760             765

Ile Pro Gln Ser Ser Arg Ser Pro Ser Tyr Arg Thr Lys Ala Lys Ser
770             775             780

His Gly Ala Leu Ser Asp Ser Lys Ser Val Asn Leu Ser Glu Ala
785             790             795             800

Arg Ala Gln Ile Ala Glu Pro Ser Thr Ser Arg Tyr Phe Pro Ser Ser
                805             810             815

Cys Leu Asp Leu Asn Ser Pro Thr Ser Pro Thr Pro Thr Arg His Ser
            820             825             830

Asp Thr Arg Thr Leu Leu Ser Pro Ser Gly Arg Asn Asn Arg Asn Glu
        835             840             845

Gly Thr Leu Asp Ser Arg Arg Thr Thr Thr Arg His Ser Lys Thr Met
850             855             860

Glu Glu Leu Lys Leu Pro Glu His Met Asp Ser Ser His Ser His Ser
865             870             875             880
```

-continued

Leu Ser Ala Pro His Glu Ser Phe Ser Tyr Gly Leu Gly Tyr Thr Ser
            885                 890                 895

Pro Phe Ser Ser Gln Gln Arg Pro His Arg His Ser Met Tyr Val Thr
            900                 905                 910

Arg Asp Lys Val Arg Ala Lys Gly Leu Asp Gly Ser Leu Ser Ile Gly
            915                 920                 925

Gln Gly Met Ala Ala Arg Ala Asn Ser Leu Gln Leu Leu Ser Pro Gln
        930                 935                 940

Pro Gly Glu Gln Leu Pro Pro Glu Met Thr Val Ala Arg Ser Ser Val
945                 950                 955                 960

Lys Glu Thr Ser Arg Gly Thr Ser Ser Phe His Thr Arg Gln Lys
            965                 970                 975

Ser Glu Gly Gly Val Tyr His Asp Pro His Ser Asp Asp Gly Thr Ala
            980                 985                 990

Pro Lys Glu Asn Arg His Leu Tyr Asn Asp Pro Val Pro Arg Arg Val
            995                 1000                1005

Gly Ser Phe Tyr Arg Val Pro Ser Pro Arg Pro Asp Asn Ser Phe
        1010                1015                1020

His Glu Asn Asn Val Ser Thr Arg Val Ser Ser Leu Pro Ser Glu
        1025                1030                1035

Ser Ser Ser Gly Thr Asn His Ser Lys Arg Gln Pro Ala Phe Asp
        1040                1045                1050

Pro Trp Lys Ser Pro Glu Asn Ile Ser His Ser Glu Gln Leu Lys
        1055                1060                1065

Glu Lys Glu Lys Gln Gly Phe Phe Arg Ser Met Lys Lys Lys Lys
        1070                1075                1080

Lys Lys Ser Gln Thr Val Pro Asn Ser Asp Ser Pro Asp Leu Leu
        1085                1090                1095

Thr Leu Gln Lys Ser Ile His Ser Ala Ser Thr Pro Ser Ser Arg
        1100                1105                1110

Pro Lys Glu Trp Arg Pro Glu Lys Ile Ser Asp Leu Gln Thr Gln
        1115                1120                1125

Ser Gln Pro Leu Lys Ser Leu Arg Lys Leu Leu His Leu Ser Ser
        1130                1135                1140

Ala Ser Asn His Pro Ala Ser Ser Asp Pro Arg Phe Gln Pro Leu
        1145                1150                1155

Thr Ala Gln Gln Thr Lys Asn Ser Phe Ser Glu Ile Arg Ile His
        1160                1165                1170

Pro Leu Ser Gln Ala Ser Gly Gly Ser Ser Asn Ile Arg Gln Glu
        1175                1180                1185

Pro Ala Pro Lys Gly Arg Pro Ala Leu Gln Leu Pro Gly Gln Met
        1190                1195                1200

Asp Pro Gly Trp His Val Ser Val Thr Arg Ser Ala Thr Glu
        1205                1210                1215

Gly Pro Ser Tyr Ser Glu Gln Leu Gly Ala Lys Ser Gly Pro Asn
        1220                1225                1230

Gly His Pro Tyr Asn Arg Thr Asn Arg Ser Arg Met Pro Asn Leu
        1235                1240                1245

Asn Asp Leu Lys Glu Thr Ala Leu Ser Ala Arg Gly Gly Pro Glu
        1250                1255                1260

Gln Lys Leu Ile Ser Glu Glu Asp Leu Asn Ser Ala Val Asp His
        1265                1270                1275

His His  His His His
    1280

<210> SEQ ID NO 13
<211> LENGTH: 3124
<212> TYPE: DNA
<213> ORGANISM: Artificial Sequence
<220> FEATURE:
<223> OTHER INFORMATION: TATk-CDKL5 fusion protein cDNA

<400> SEQUENCE: 13

| | | | | | | |
|---|---|---|---|---|---|---|
| gctagccacc | atggagacag | acacactcct | gctatgggta | ctgctgctct | gggttccagg | 60 |
| ttccactggt | gacgcggccc | agccggccag | gcgcgcgcgc | cgtacgaagc | ttgcggccta | 120 |
| cgccagaaag | gccgccaggc | aggccagggc | accggtgaag | attcctaaca | ttggtaatgt | 180 |
| gatgaataaa | tttgagatcc | ttggggttgt | aggtgaagga | gcctatggag | ttgtacttaa | 240 |
| atgcagacac | aaggaaacac | atgaaattgt | ggcgatcaag | aaattcaagg | acagtgaaga | 300 |
| aaatgaagaa | gtcaaagaaa | cgactttacg | agagcttaaa | atgcttcgga | ctctcaagca | 360 |
| ggaaaacatt | gtggagttga | aggaagcatt | tcgtcggagg | ggaaagttgt | acttggtgtt | 420 |
| tgagtatgtt | gaaaaaaata | tgctcgaatt | gctggaagaa | atgccaaatg | gagttccacc | 480 |
| tgagaaagta | aaaagctaca | tctatcagct | aatcaaggct | attcactggt | gccataagaa | 540 |
| tgatattgtc | catcgagata | taaaaccaga | aaatctctta | atcagccaca | atgatgtcct | 600 |
| aaaactgtgt | gactttggtt | tgctcgtaa | tctgtcagaa | ggcaataatg | ctaattacac | 660 |
| agagtacgtt | gccaccagat | ggtatcggtc | cccagaactc | ttacttggcg | ctccctatgg | 720 |
| aaagtccgtg | gacatgtggt | cggtgggctg | tattcttggg | gagcttagcg | atggacagcc | 780 |
| tttatttcct | ggagaaagtg | aaattgacca | acttttttact | attcagaagg | tgctaggacc | 840 |
| acttccatct | gagcagatga | agcttttcta | cagtaatcct | cgcttccatg | ggctccggtt | 900 |
| tccagctgtt | aaccatcctc | agtccttgga | aagaagatac | cttggaattt | tgaatagtgt | 960 |
| tctacttgac | ctaatgaaga | atttactgaa | gttggaccca | gctgacagat | acttgacaga | 1020 |
| acagtgtttg | aatcacccta | catttcaaac | ccagagactt | ctggatcgtt | ctccttcaag | 1080 |
| gtcagcaaaa | agaaaacctt | accatgtgga | aagcagcaca | ttgtctaata | gaaaccaagc | 1140 |
| cggcaaaagt | actgctttgc | agtctcacca | cagatctaac | agcaaggaca | tccagaacct | 1200 |
| gagtgtaggc | ctgccccggg | ctgacgaagg | tctccctgcc | aatgaaagct | tcctaaatgg | 1260 |
| aaaccttgct | ggagctagtc | ttagtccact | gcacaccaaa | acctaccaag | caagcagcca | 1320 |
| gcctgggtct | accagcaaag | atctcaccaa | caacaacata | ccacaccttc | ttagcccaaa | 1380 |
| agaagccaag | tcaaaaacag | agtttgattt | taatattgac | ccaaagcctt | cagaaggccc | 1440 |
| agggacaaag | tacctcaagt | caaacagcag | atctcagcag | aaccgccact | cattcatgga | 1500 |
| aagctctcaa | agcaaagctg | ggacactgca | gcccaatgaa | aagcagagtc | ggcatagcta | 1560 |
| tattgacaca | attccccagt | cctctaggag | tccctcctac | aggaccaagg | ccaaaagcca | 1620 |
| tgggcactg | agtgactcca | agtctgtgag | caaccttttct | gaagccaggg | cccaaattgc | 1680 |
| ggagcccagt | accagtaggt | acttcccatc | tagctgctta | gacttgaatt | ctccccaccag | 1740 |
| cccaaccccc | accagacaca | gtgacacgag | aactttgctc | agcccttctg | gaagaaataa | 1800 |
| ccgaaatgag | ggaacgctgg | actcacgtcg | aaccacaacc | agacattcta | gacgatgga | 1860 |
| ggaattgaag | ctgccggagc | acatggacag | tagccattcc | cattcactgt | ctgcacctca | 1920 |
| cgaatctttt | tcttatggac | tgggctacac | cagcccccttt | tcttcccagc | aacgtcctca | 1980 |

-continued

```
taggcattct atgtatgtga cccgtgacaa agtgagagcc aagggcttgg atggaagctt    2040
gagcataggg caaggatgg cagctagagc aacagcctg caactcttgt caccccagcc      2100
tggagaacag ctccctccag agatgactgt ggcaagatct tcggtcaaag agacctccag    2160
agaaggcacc tcttccttcc atacacgcca gaagtctgag ggtggagtgt atcatgaccc    2220
acactctgat gatggcacag cccccaaaga aaatagacac ctatacaatg atcctgtgcc    2280
aaggagagtt ggtagctttt acagagtgcc atctccacgt ccagacaatt ctttccatga    2340
aaataatgtg tcaactagag tttcttctct accatcagag agcagttctg gaaccaacca    2400
ctcaaaaaga caaccagcat tcgatccatg gaaaagtcct gaaaatatta gtcattcaga    2460
gcaactcaag gaaaagagaa agcaaggatt tttcaggtca atgaaaaaga aaagaagaa     2520 atctcaaaca gtacccaatt ccgacagccc tgatcttctg acgttgcaga atccattca    2580 ttctgctagc actccaagca gcagaccaaa ggagtggcgc cccgagaaga tctcagatct    2640
gcagacccaa agccagccat taaaatcact gcgcaagttg ttacatctct cttcggcctc    2700
aaatcacccg gcttcctcag atcccgctt ccagcccta acagctcaac aaaccaaaaa     2760
ttccttctca gaaattcgga ttcacccct gagccaggcc tctggcggga gcagcaacat    2820
ccggcaggaa cccgcaccga agggcaggcc agccctccag ctgccaggtc agatggatcc    2880
tggttggcat gtgtcctctg tgaccaggag tgccacagag ggcccttcct actctgaaca    2940
gctgggtgcc aaaagtgggc caaatgggca cccctataac agaacaaatc gctcacgaat    3000
gccaaatctg aatgatttaa agagacagc cttgtctaga ggatcccggg ctgactacaa     3060
agaccatgac ggtgattata agatcatga catcgactac aaggatgacg atgacaagta    3120
gtga                                                                 3124
```

<210> SEQ ID NO 14
<211> LENGTH: 1036
<212> TYPE: PRT
<213> ORGANISM: Artificial Sequence
<220> FEATURE:
<223> OTHER INFORMATION: TATk-CDKL5 fusion protein polypeptide

<400> SEQUENCE: 14

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Ala Ala Tyr Ala Arg Lys Ala Ala Arg Gln Ala Arg Ala Pro
        35                  40                  45

Val Lys Ile Pro Asn Ile Gly Asn Val Met Asn Lys Phe Glu Ile Leu
    50                  55                  60

Gly Val Val Gly Glu Gly Ala Tyr Gly Val Val Leu Lys Cys Arg His
65                  70                  75                  80

Lys Glu Thr His Glu Ile Val Ala Ile Lys Lys Phe Lys Asp Ser Glu
                85                  90                  95

Glu Asn Glu Glu Val Lys Glu Thr Thr Leu Arg Glu Leu Lys Met Leu
            100                 105                 110

Arg Thr Leu Lys Gln Glu Asn Ile Val Glu Leu Lys Glu Ala Phe Arg
        115                 120                 125

Arg Arg Gly Lys Leu Tyr Leu Val Phe Glu Tyr Val Glu Lys Asn Met
    130                 135                 140

Leu Glu Leu Leu Glu Glu Met Pro Asn Gly Val Pro Pro Glu Lys Val
145                 150                 155                 160
```

```
Lys Ser Tyr Ile Tyr Gln Leu Ile Lys Ala Ile His Trp Cys His Lys
                165                 170                 175

Asn Asp Ile Val His Arg Asp Ile Lys Pro Glu Asn Leu Leu Ile Ser
            180                 185                 190

His Asn Asp Val Leu Lys Leu Cys Asp Phe Gly Phe Ala Arg Asn Leu
        195                 200                 205

Ser Glu Gly Asn Asn Ala Asn Tyr Thr Glu Tyr Val Ala Thr Arg Trp
    210                 215                 220

Tyr Arg Ser Pro Glu Leu Leu Gly Ala Pro Tyr Gly Lys Ser Val
225                 230                 235                 240

Asp Met Trp Ser Val Gly Cys Ile Leu Gly Glu Leu Ser Asp Gly Gln
                245                 250                 255

Pro Leu Phe Pro Gly Glu Ser Glu Ile Asp Gln Leu Phe Thr Ile Gln
            260                 265                 270

Lys Val Leu Gly Pro Leu Pro Ser Glu Gln Met Lys Leu Phe Tyr Ser
        275                 280                 285

Asn Pro Arg Phe His Gly Leu Arg Phe Pro Ala Val Asn His Pro Gln
    290                 295                 300

Ser Leu Glu Arg Arg Tyr Leu Gly Ile Leu Asn Ser Val Leu Leu Asp
305                 310                 315                 320

Leu Met Lys Asn Leu Leu Lys Leu Asp Pro Ala Asp Arg Tyr Leu Thr
                325                 330                 335

Glu Gln Cys Leu Asn His Pro Thr Phe Gln Thr Gln Arg Leu Leu Asp
            340                 345                 350

Arg Ser Pro Ser Arg Ser Ala Lys Arg Lys Pro Tyr His Val Glu Ser
        355                 360                 365

Ser Thr Leu Ser Asn Arg Asn Gln Ala Gly Lys Ser Thr Ala Leu Gln
    370                 375                 380

Ser His His Arg Ser Asn Ser Lys Asp Ile Gln Asn Leu Ser Val Gly
385                 390                 395                 400

Leu Pro Arg Ala Asp Glu Gly Leu Pro Ala Asn Glu Ser Phe Leu Asn
                405                 410                 415

Gly Asn Leu Ala Gly Ala Ser Leu Ser Pro Leu His Thr Lys Thr Tyr
            420                 425                 430

Gln Ala Ser Ser Gln Pro Gly Ser Thr Ser Lys Asp Leu Thr Asn Asn
        435                 440                 445

Asn Ile Pro His Leu Leu Ser Pro Lys Glu Ala Lys Ser Lys Thr Glu
    450                 455                 460

Phe Asp Phe Asn Ile Asp Pro Lys Pro Ser Glu Gly Pro Gly Thr Lys
465                 470                 475                 480

Tyr Leu Lys Ser Asn Ser Arg Ser Gln Gln Asn Arg His Ser Phe Met
                485                 490                 495

Glu Ser Ser Gln Ser Lys Ala Gly Thr Leu Gln Pro Asn Glu Lys Gln
            500                 505                 510

Ser Arg His Ser Tyr Ile Asp Thr Ile Pro Gln Ser Ser Arg Ser Pro
        515                 520                 525

Ser Tyr Arg Thr Lys Ala Lys Ser His Gly Ala Leu Ser Asp Ser Lys
    530                 535                 540

Ser Val Ser Asn Leu Ser Glu Ala Arg Ala Gln Ile Ala Glu Pro Ser
545                 550                 555                 560

Thr Ser Arg Tyr Phe Pro Ser Ser Cys Leu Asp Leu Asn Ser Pro Thr
                565                 570                 575
```

```
Ser Pro Thr Pro Thr Arg His Ser Asp Thr Arg Thr Leu Leu Ser Pro
            580                 585                 590

Ser Gly Arg Asn Asn Arg Asn Glu Gly Thr Leu Asp Ser Arg Arg Thr
        595                 600                 605

Thr Thr Arg His Ser Lys Thr Met Glu Glu Leu Lys Leu Pro Glu His
    610                 615                 620

Met Asp Ser Ser His Ser His Ser Leu Ser Ala Pro His Glu Ser Phe
625                 630                 635                 640

Ser Tyr Gly Leu Gly Tyr Thr Ser Pro Phe Ser Gln Gln Arg Pro
                645                 650                 655

His Arg His Ser Met Tyr Val Thr Arg Asp Lys Val Arg Ala Lys Gly
            660                 665                 670

Leu Asp Gly Ser Leu Ser Ile Gly Gln Gly Met Ala Ala Arg Ala Asn
                675                 680                 685

Ser Leu Gln Leu Leu Ser Pro Gln Pro Gly Glu Gln Leu Pro Pro Glu
        690                 695                 700

Met Thr Val Ala Arg Ser Ser Val Lys Glu Thr Ser Arg Glu Gly Thr
705                 710                 715                 720

Ser Ser Phe His Thr Arg Gln Lys Ser Glu Gly Gly Val Tyr His Asp
                725                 730                 735

Pro His Ser Asp Asp Gly Thr Ala Pro Lys Glu Asn Arg His Leu Tyr
                740                 745                 750

Asn Asp Pro Val Pro Arg Arg Val Gly Ser Phe Tyr Arg Val Pro Ser
            755                 760                 765

Pro Arg Pro Asp Asn Ser Phe His Glu Asn Asn Val Ser Thr Arg Val
770                 775                 780

Ser Ser Leu Pro Ser Glu Ser Ser Ser Gly Thr Asn His Ser Lys Arg
785                 790                 795                 800

Gln Pro Ala Phe Asp Pro Trp Lys Ser Pro Glu Asn Ile Ser His Ser
            805                 810                 815

Glu Gln Leu Lys Glu Lys Glu Lys Gln Gly Phe Phe Arg Ser Met Lys
                820                 825                 830

Lys Lys Lys Lys Lys Ser Gln Thr Val Pro Asn Ser Asp Ser Pro Asp
                835                 840                 845

Leu Leu Thr Leu Gln Lys Ser Ile His Ser Ala Ser Thr Pro Ser Ser
850                 855                 860

Arg Pro Lys Glu Trp Arg Pro Glu Lys Ile Ser Asp Leu Gln Thr Gln
865                 870                 875                 880

Ser Gln Pro Leu Lys Ser Leu Arg Lys Leu Leu His Leu Ser Ser Ala
                885                 890                 895

Ser Asn His Pro Ala Ser Ser Asp Pro Arg Phe Gln Pro Leu Thr Ala
                900                 905                 910

Gln Gln Thr Lys Asn Ser Phe Ser Glu Ile Arg Ile His Pro Leu Ser
            915                 920                 925

Gln Ala Ser Gly Gly Ser Ser Asn Ile Arg Gln Glu Pro Ala Pro Lys
        930                 935                 940

Gly Arg Pro Ala Leu Gln Leu Pro Gly Gln Met Asp Pro Gly Trp His
945                 950                 955                 960

Val Ser Ser Val Thr Arg Ser Ala Thr Glu Gly Pro Ser Tyr Ser Glu
                965                 970                 975

Gln Leu Gly Ala Lys Ser Gly Pro Asn Gly His Pro Tyr Asn Arg Thr
            980                 985                 990

Asn Arg Ser Arg Met Pro Asn Leu  Asn Asp Leu Lys Glu  Thr Ala Leu
```

| | | | |
|---|---|---|---|
| 995 | | 1000 | 1005 |

Ser Arg Gly Ser Arg Ala Asp Tyr Lys Asp His Asp Gly Asp Tyr
    1010            1015            1020

Lys Asp His Asp Ile Asp Tyr Lys Asp Asp Asp Lys
1025            1030            1035

<210> SEQ ID NO 15
<211> LENGTH: 2877
<212> TYPE: DNA
<213> ORGANISM: Artificial Sequence
<220> FEATURE:
<223> OTHER INFORMATION: CDKL5 (107) cDNA

<400> SEQUENCE: 15

| | |
|---|---|
| aagattccta acattggtaa tgtgatgaat aaatttgaga tccttggggt tgtaggtgaa | 60 |
| ggagcctatg gagttgtact aaatgcaga cacaaggaaa cacatgaaat tgtggcgatc | 120 |
| aagaaattca ggacagtga agaaaatgaa gaagtcaaag aaacgacttt acgagagctt | 180 |
| aaaatgcttc ggactctcaa gcaggaaaac attgtggagt tgaaggaagc atttcgtcgg | 240 |
| agggaaagt tgtacttggt gtttgagtat gttgaaaaaa atatgctcga attgctggaa | 300 |
| gaaatgccaa atggagttcc acctgagaaa gtaaaaagct acatctatca gctaatcaag | 360 |
| gctattcact ggtgccataa gaatgatatt gtccatcgag atataaaacc agaaaatctc | 420 |
| ttaatcagcc acaatgatgt cctaaaactg tgtgactttg gttttgctcg taatctgtca | 480 |
| gaaggcaata atgctaatta cacagagtac gttgccacca gatggtatcg gtccccagaa | 540 |
| ctcttacttg gcgctcccta tggaaagtcc gtggacatgt ggtcggtggg ctgtattctt | 600 |
| ggggagctta gcgatggaca gcctttattt cctggagaaa gtgaaattga ccaacttttt | 660 |
| actattcaga aggtgctagg accacttcca tctgagcaga tgaagctttt ctacagtaat | 720 |
| cctcgcttcc atgggctccg gtttccagct gttaaccatc ctcagtcctt ggaaagaaga | 780 |
| taccttggaa ttttgaatag tgttctactt gacctaatga agaatttact gaagttggac | 840 |
| ccagctgaca gatacttgac agaacagtgt ttgaatcacc ctacatttca aacccagaga | 900 |
| cttctggatc gttctccttc aaggtcagca aaaagaaaac cttaccatgt ggaaagcagc | 960 |
| acattgtcta atagaaacca agccggcaaa agtactgctt tgcagtctca ccacagatct | 1020 |
| aacagcaagg acatccagaa cctgagtgta ggcctgcccc gggctgacga aggtctccct | 1080 |
| gccaatgaaa gcttcctaaa tggaaacctt gctggagcta gtcttagtcc actgcacacc | 1140 |
| aaaacctacc aagcaagcag ccagcctggg tctaccagca agatctcac caacaacaac | 1200 |
| ataccacacc ttcttagccc aaaagaagcc aagtcaaaaa cagagtttga ttttaatatt | 1260 |
| gacccaaagc cttcagaagg cccagggaca agtacctca agtcaaacag cagatctcag | 1320 |
| cagaaccgcc actcattcat ggaaagctct caaagcaaag ctgggacact gcagcccaat | 1380 |
| gaaaagcaga gtcggcatag ctatattgac acaattcccc agtcctctag gagtccctcc | 1440 |
| tacaggacca aggccaaaag ccatgggca ctgagtgact ccaagtctgt gagcaacctt | 1500 |
| tctgaagcca gggcccaaat tgcggagccc agtaccagta ggtacttccc atctagctgc | 1560 |
| ttagacttga attctcccac cagcccaacc cccaccagac acagtgacac gagaactttg | 1620 |
| ctcagcccctt ctggaagaaa taccgaaat gagggaacgc tggactcacg tcgaaccaca | 1680 |
| accagacatt ctaagacgat ggaggaattg aagctgccgg agcacatgga cagtagccat | 1740 |
| tcccattcac tgtctgcacc tcacgaatct tttttcttatg gactgggcta caccagcccc | 1800 |
| ttttcttccc agcaacgtcc tcataggcat tctatgtatg tgacccgtga caaagtgaga | 1860 |

```
gccaagggct tggatggaag cttgagcata gggcaaggga tggcagctag agccaacagc   1920
ctgcaactct tgtcacccca gcctggagaa cagctccctc cagagatgac tgtggcaaga   1980
tcttcggtca aagagacctc cagagaaggc acctcttcct tccatacacg ccagaagtct   2040
gagggtggag tgtatcatga cccacactct gatgatggca cagcccccaa agaaaataga   2100
cacctataca atgatcctgt gccaaggaga gttggtagct tttacagagt gccatctcca   2160
cgtccagaca attctttcca tgaaaataat gtgtcaacta gagtttcttc tctaccatca   2220
gagagcagtt ctggaaccaa ccactcaaaa agacaaccag cattcgatcc atggaaaagt   2280
cctgaaaata ttagtcattc agcaactc aaggaaaaag agaagcaagg atttttcagg    2340
tcaatgaaaa agaaaaagaa gaaatctcaa acagtaccca attccgacag ccctgatctt   2400
ctgacgttgc agaaatccat tcattctgct agcactccaa gcagcagacc aaaggagtgg   2460
cgccccgaga agatctcaga tctgcagacc caaagccagc cattaaaatc actgcgcaag   2520
ttgttacatc tctcttcggc ctcaaatcac ccggcttcct cagatccccg cttccagccc   2580
ttaacagctc aacaaaccaa aaattccttc tcagaaattc ggattcaccc cctgagccag   2640
gcctctggcg ggagcagcaa catccggcag gaacccgcac cgaagggcag gccagccctc   2700
cagctgccag gtcagatgga tcctggttgg catgtgtcct ctgtgaccag gagtgccaca   2760
gagggccctt cctactctga acagctgggt gccaaaagtg ggccaaatgg caccccctat   2820
aacagaacaa atcgctcacg aatgccaaat ctgaatgatt taaaagagac agccttg     2877
```

<210> SEQ ID NO 16
<211> LENGTH: 959
<212> TYPE: PRT
<213> ORGANISM: Artificial Sequence
<220> FEATURE:
<223> OTHER INFORMATION: CDKL5 (107) polypeptide

<400> SEQUENCE: 16

```
Lys Ile Pro Asn Ile Gly Asn Val Met Asn Lys Phe Glu Ile Leu Gly
1               5                   10                  15

Val Val Gly Glu Gly Ala Tyr Gly Val Val Leu Lys Cys Arg His Lys
            20                  25                  30

Glu Thr His Glu Ile Val Ala Ile Lys Lys Phe Lys Asp Ser Glu Glu
        35                  40                  45

Asn Glu Glu Val Lys Glu Thr Thr Leu Arg Glu Leu Lys Met Leu Arg
    50                  55                  60

Thr Leu Lys Gln Glu Asn Ile Val Glu Leu Lys Glu Ala Phe Arg Arg
65                  70                  75                  80

Arg Gly Lys Leu Tyr Leu Val Phe Glu Tyr Val Glu Lys Asn Met Leu
                85                  90                  95

Glu Leu Leu Glu Glu Met Pro Asn Gly Val Pro Pro Glu Lys Val Lys
            100                 105                 110

Ser Tyr Ile Tyr Gln Leu Ile Lys Ala Ile His Trp Cys His Lys Asn
        115                 120                 125

Asp Ile Val His Arg Asp Ile Lys Pro Glu Asn Leu Leu Ile Ser His
    130                 135                 140

Asn Asp Val Leu Lys Leu Cys Asp Phe Gly Phe Ala Arg Asn Leu Ser
145                 150                 155                 160

Glu Gly Asn Asn Ala Asn Tyr Thr Glu Tyr Val Ala Thr Arg Trp Tyr
                165                 170                 175

Arg Ser Pro Glu Leu Leu Leu Gly Ala Pro Tyr Gly Lys Ser Val Asp
```

```
                180             185             190
Met Trp Ser Val Gly Cys Ile Leu Gly Glu Leu Ser Asp Gly Gln Pro
            195             200             205
Leu Phe Pro Gly Glu Ser Glu Ile Asp Gln Leu Phe Thr Ile Gln Lys
            210             215             220
Val Leu Gly Pro Leu Pro Ser Glu Gln Met Lys Leu Phe Tyr Ser Asn
225             230             235             240
Pro Arg Phe His Gly Leu Arg Phe Pro Ala Val Asn His Pro Gln Ser
            245             250             255
Leu Glu Arg Arg Tyr Leu Gly Ile Leu Asn Ser Val Leu Leu Asp Leu
            260             265             270
Met Lys Asn Leu Leu Lys Leu Asp Pro Ala Asp Arg Tyr Leu Thr Glu
            275             280             285
Gln Cys Leu Asn His Pro Thr Phe Gln Thr Gln Arg Leu Leu Asp Arg
            290             295             300
Ser Pro Ser Arg Ser Ala Lys Arg Lys Pro Tyr His Val Glu Ser Ser
305             310             315             320
Thr Leu Ser Asn Arg Asn Gln Ala Gly Lys Ser Thr Ala Leu Gln Ser
            325             330             335
His His Arg Ser Asn Ser Lys Asp Ile Gln Asn Leu Ser Val Gly Leu
            340             345             350
Pro Arg Ala Asp Glu Gly Leu Pro Ala Asn Glu Ser Phe Leu Asn Gly
            355             360             365
Asn Leu Ala Gly Ala Ser Leu Ser Pro Leu His Thr Lys Thr Tyr Gln
            370             375             380
Ala Ser Ser Gln Pro Gly Ser Thr Ser Lys Asp Leu Thr Asn Asn Asn
385             390             395             400
Ile Pro His Leu Leu Ser Pro Lys Glu Ala Lys Ser Lys Thr Glu Phe
            405             410             415
Asp Phe Asn Ile Asp Pro Lys Pro Ser Glu Gly Pro Gly Thr Lys Tyr
            420             425             430
Leu Lys Ser Asn Ser Arg Ser Gln Gln Asn Arg His Ser Phe Met Glu
            435             440             445
Ser Ser Gln Ser Lys Ala Gly Thr Leu Gln Pro Asn Glu Lys Gln Ser
            450             455             460
Arg His Ser Tyr Ile Asp Thr Ile Pro Gln Ser Ser Arg Ser Pro Ser
465             470             475             480
Tyr Arg Thr Lys Ala Lys Ser His Gly Ala Leu Ser Asp Ser Lys Ser
            485             490             495
Val Ser Asn Leu Ser Glu Ala Arg Ala Gln Ile Ala Glu Pro Ser Thr
            500             505             510
Ser Arg Tyr Phe Pro Ser Ser Cys Leu Asp Leu Asn Ser Pro Thr Ser
            515             520             525
Pro Thr Pro Thr Arg His Ser Asp Thr Arg Thr Leu Leu Ser Pro Ser
            530             535             540
Gly Arg Asn Asn Arg Asn Glu Gly Thr Leu Asp Ser Arg Arg Thr Thr
545             550             555             560
Thr Arg His Ser Lys Thr Met Glu Glu Leu Lys Leu Pro Glu His Met
            565             570             575
Asp Ser Ser His Ser His Ser Leu Ser Ala Pro His Glu Ser Phe Ser
            580             585             590
Tyr Gly Leu Gly Tyr Thr Ser Pro Phe Ser Ser Gln Gln Arg Pro His
            595             600             605
```

```
Arg His Ser Met Tyr Val Thr Arg Asp Lys Val Arg Ala Lys Gly Leu
    610                 615                 620

Asp Gly Ser Leu Ser Ile Gly Gln Gly Met Ala Ala Arg Ala Asn Ser
625                 630                 635                 640

Leu Gln Leu Leu Ser Pro Gln Pro Gly Glu Gln Leu Pro Pro Glu Met
                645                 650                 655

Thr Val Ala Arg Ser Ser Val Lys Glu Thr Ser Arg Glu Gly Thr Ser
            660                 665                 670

Ser Phe His Thr Arg Gln Lys Ser Glu Gly Gly Val Tyr His Asp Pro
        675                 680                 685

His Ser Asp Asp Gly Thr Ala Pro Lys Glu Asn Arg His Leu Tyr Asn
        690                 695                 700

Asp Pro Val Pro Arg Arg Val Gly Ser Phe Tyr Arg Val Pro Ser Pro
705                 710                 715                 720

Arg Pro Asp Asn Ser Phe His Glu Asn Asn Val Ser Thr Arg Val Ser
                725                 730                 735

Ser Leu Pro Ser Glu Ser Ser Ser Gly Thr Asn His Ser Lys Arg Gln
                740                 745                 750

Pro Ala Phe Asp Pro Trp Lys Ser Pro Glu Asn Ile Ser His Ser Glu
            755                 760                 765

Gln Leu Lys Glu Lys Glu Lys Gln Gly Phe Phe Arg Ser Met Lys Lys
        770                 775                 780

Lys Lys Lys Lys Ser Gln Thr Val Pro Asn Ser Asp Ser Pro Asp Leu
785                 790                 795                 800

Leu Thr Leu Gln Lys Ser Ile His Ser Ala Ser Thr Pro Ser Ser Arg
                805                 810                 815

Pro Lys Glu Trp Arg Pro Glu Lys Ile Ser Asp Leu Gln Thr Gln Ser
            820                 825                 830

Gln Pro Leu Lys Ser Leu Arg Lys Leu Leu His Leu Ser Ser Ala Ser
        835                 840                 845

Asn His Pro Ala Ser Ser Asp Pro Arg Phe Gln Pro Leu Thr Ala Gln
        850                 855                 860

Gln Thr Lys Asn Ser Phe Ser Glu Ile Arg Ile His Pro Leu Ser Gln
865                 870                 875                 880

Ala Ser Gly Gly Ser Ser Asn Ile Arg Gln Glu Pro Ala Pro Lys Gly
                885                 890                 895

Arg Pro Ala Leu Gln Leu Pro Gly Gln Met Asp Pro Gly Trp His Val
            900                 905                 910

Ser Ser Val Thr Arg Ser Ala Thr Glu Gly Pro Ser Tyr Ser Glu Gln
        915                 920                 925

Leu Gly Ala Lys Ser Gly Pro Asn Gly His Pro Tyr Asn Arg Thr Asn
        930                 935                 940

Arg Ser Arg Met Pro Asn Leu Asn Asp Leu Lys Glu Thr Ala Leu
945                 950                 955
```

TATK-CDKL5 FUSION PROTEINS, COMPOSITIONS, FORMULATIONS, AND USE THEREOF

CROSS-REFERENCE TO RELATED APPLICATIONS

This application is a continuation of U.S. nonprovisional application Ser. No. 15/075,457, filed on Mar. 21, 2016, having the title "TATk-CDKL5 FUSION PROTEINS, COMPOSITIONS, FORMULATIONS, AND USE THEREOF," which is a continuation of U.S. nonprovisional application Ser. No. 14/633,757, filed on Feb. 27, 2015, having the title "TATk-CDKL5 FUSION PROTEINS, COMPOSITIONS, FORMULATIONS, AND THEIR METHODS OF MAKING AND METHODS OF USING," now U.S. Pat. No. 9,290,746, which claims the benefit of U.S. provisional patent application Ser. No. 61/946,280 filed on Feb. 28, 2014, having the title "TATk-CDKL5 FUSION PROTEINS, COMPOSITIONS, FORMULATIONS, AND THEIR METHODS OF MAKING AND METHODS OF USING," the disclosures of which is incorporated herein in their entirety.

SEQUENCE LISTING(S)

This application contains a sequence listing filed in electronic form as an ASCII.txt file entitled 02190796.txt, created on Apr. 24, 2015 and having a size of 84,096 bytes. The content of the sequence listing is incorporated herein in its entirety.

BACKGROUND

Cyclin-dependent kinase-like 5 (CDKL5) mutation/deficiency, also known as atypical Rett syndrome, is a debilitating postnatal neurological disorder that occurs worldwide in 1 of every 17000 to 38000 female births. Males are also affected at a lower incidence. This disorder is not limited to ethnic or racial origin. Symptoms of CDKL5 mutation/deficiency range from mild to severe and present as early onset seizure, cognitive disability, hypotonia as well as autonomic, sleep and gastrointestinal disturbances. Symptoms of disease result from the deficiency of a functional CDKL5 protein.

Mutations in the X-linked CDKL5 gene or deficiencies in the CDKL5 protein in individuals are implicated in the development of atypical or congenital Rett syndrome. See Bertani et al., J. biol. Chem. 2006, 281:32048-320 56, Scala et al., J. Med. Gen., 2005. 42:103-107, and Kalscheuer et al., Am. J. Hum. Genet. 2003. 72:1401-1411. The CDKL5 gene is located on the X-chromosome and encodes a protein that is essential for normal brain development and function. CDKL5 protein is a multifunctional protein that has multiple effects in a neuronal cell. For example, CDKL5 can act as a kinase and phosphorylate MeCP2. Girls affected by the CDKL5 mutations or deficiencies typically have a normal prenatal history, irritability and drowsiness in the perinatal period; early-onset epilepsy with onset before 5 months of age, Rett-like features, including deceleration of head growth, stereotypies, poor to absent voluntary hand use, and sleep disturbances, and severe mental retardation with poor eye contact and virtually no language. See Bahi-Buisson and Bienvenu. 2012. Mol. Syndromol. 2:137-152.

Current treatments for CDKL5 mutations/deficiencies are primarily focused on managing symptoms. However, there are currently no treatments that improve the neurological outcome of subjects with CDKL5 mutations or deficiencies. As such, there exists a need for development of therapies for treating the CDKL5 mutations and deficiencies.

SUMMARY

Described herein are fusion proteins having a CDKL5 polypeptide sequence, wherein the CDKL5 polypeptide sequence has about 50% to 100% sequence identity to SEQ ID NO: 2 or SEQ ID NO: 16, and a TATk polypeptide sequence, wherein the TATk polypeptide sequence has about 90% to about 100° % sequence identity to SEQ ID NO: 4, wherein the TATk polypeptide is operatively coupled to the CDKL5 polypeptide. In some aspects, the fusion protein can contain an Igk-chain leader sequence polypeptide, wherein the Igk-chain leader sequence is operatively coupled to the CDKL5 polypeptide. In further aspects, the fusion protein can contain a reporter protein polypeptide, wherein the reporter protein polypeptide is operatively coupled to the CDKL5 polypeptide. In other aspects, the fusion protein can contain a protein tag polypeptide, wherein the protein tag polypeptide is operatively coupled to the CDKL5 polypeptide. In some aspects, the fusion proteins can increase neurite growth, elongation, branch number, or branch density in a brain of a subject as compared to a control. In other aspects, the fusion proteins can reduce neuron apoptosis in the brain of a subject as compared to a control. In some aspects the fusion protein can have a polypeptide sequence according to SEQ ID NO: 8, SEQ ID NO: 10, SEQ ID NO: 12, or SEQ ID NO: 14.

Also provided herein are pharmaceutical formulations containing a therapeutically effective amount of a fusion protein having a CDKL5 polypeptide sequence, wherein the CDKL5 polypeptide sequence has about 50% to 100% sequence identity to SEQ ID NO:2 or SEQ ID NO: 16, and a TATk polypeptide sequence, wherein the TATk polypeptide sequence has about 90% to about 100% sequence identity to SEQ ID NO: 4, wherein the TATk polypeptide is operatively coupled to the CDKL5 polypeptide and a pharmaceutically acceptable carrier. In some aspects the fusion protein contained in the pharmaceutical formulations can contain an Igk-chain leader sequence polypeptide, wherein the Igk-chain leader sequence is operatively coupled to the CDKL5 polypeptide. In some aspects, the fusion protein contained in the pharmaceutical formulations can contain a reporter protein polypeptide, wherein the reporter protein polypeptide is operatively coupled to the CDKL5 polypeptide. In further aspects, the fusion protein contained in the pharmaceutical formulations can have a polypeptide sequence according to SEQ ID NO: 8, SEQ ID NO: 10, SEQ ID NO: 12, or SEQ ID NO: 14. In further aspects, the therapeutically effective amount of the fusion protein can treat one or more symptoms of a CDKL5 deficiency, Rett syndrome, or Rett syndrome variant in a subject as compared to a control. In additional aspects, the therapeutically effective amount of the fusion protein can increase neurite growth, elongation, branch number, or branch density in a brain of a subject as compared to a control. In other aspects, the therapeutically effective amount of the fusion protein can reduce neuron apoptosis in the brain of a subject as compared to a control. In additional aspects, the therapeutically effective amount of the fusion protein can improve motor function in a subject as compared to a control. In some aspects, the therapeutically effective amount of the fusion protein can improve cognitive function in a subject as compared to a control.

Provided herein are methods of administering to a subject in need thereof a therapeutically effective amount of a pharmaceutical formulation containing an amount of a fusion protein, where the fusion protein contains a CDKL5 polypeptide sequence, wherein the CDKL5 polypeptide sequence has about 50% to 100%, sequence identity to SEQ ID NO:2 or SEQ ID NO: 16 and a TATk polypeptide sequence, wherein the TATk polypeptide sequence has about 90% to about 100% sequence identity to SEQ ID NO: 4, wherein the TATk polypeptide is operatively coupled to the CDKL5 polypeptide, and a pharmaceutically acceptable carrier. In some aspects the subject in need thereof has or is suspected of having a CDKL5 deficiency, Rett syndrome, or a Rett syndrome variant. In other aspects of the method of administering a therapeutically effective amount of the pharmaceutical formulation, the therapeutically effective amount of the fusion protein can treat one or more symptoms of a CDKL5 deficiency, Rett syndrome, or Rett syndrome variant in a subject as compared to a control.

BRIEF DESCRIPTION OF THE DRAWINGS

FIG. 4A demonstrates TATk-GFP-CDKL5 fusion protein expression in cell extract from transfected HEK293T cells.

FIG. 4B demonstrates TATk-GFP-CDKL5 fusion protein purification from 20× concentrated cell culture medium from TATk-GFP-CDKL5-transfected HEK293T cells.

FIGS. 7A and 7B demonstrate the efficiency of transduction of HEK 293T cells with a TATk-GFP-CDKL5 fusion protein as compared to the control (FIG. 7A) (panel on the left). Immunodetection was conducted using an anti-GFP antibody and cells were counterstained with DAPI. The white arrows indicate transduced HEK 293T cells.

FIG. 8 demonstrates the efficiency of transduction of SH-SY5Y cells with a TATk-GFP-CDKL5 fusion protein.

FIG. 11A-11B are images demonstrating a representative phase contrast image of TATk-GFP treated (control) SH-SY5Y cells (FIG. 11A) and TATk-GFP-CDKL5 treated SH-SY5Y cells (FIG. 11B). Neurite growth was observed to be greater in TATk-GFP-CDKL5 treated SH-SY5Y cells as compared to control cells.

FIG. 12 shows a graph demonstrating the quantification of neurite outgrowth of SH-SY5Y cells treated with, TATk-GFP fusion protein (control), or TATk-GFP-CDKL5. Data is shown as mean±S.E. * $P<0.05$ (t-test). The y-axis shows neuritic length/cell in microns.

FIGS. 17A-17F show images demonstrating immunodetection of CDKL5 in the brains of mice (postnatal day 7) systemically treated (one single injection) with the concentrated culture medium (vehicle) (FIGS. 17A and 17D), TATk-GFP (FIGS. 17B and 17E), and TATk-GFP-CDKL5 (FIGS. 17C and 17F). FIGS. 17D-17F illustrate magnifications of the dotted boxes in FIG. 17A-17C, respectively. Localization of TATk-GFP-CDKL5 and TATk-GFP in the brain was evaluated by immunohistochemistry using an anti-GFP antibody (red). Images were taken at the level of the sensory-motor cortex. Scale bar=60 µm (lower magnification) and 20 µm (higher magnification).

18B, 18C). Abbreviations: EGL, external granular layer; IGL, internal granular layer; ML, molecular layer; PL, Purkinje layer. Scale bar=60 μm.

Figure 19:
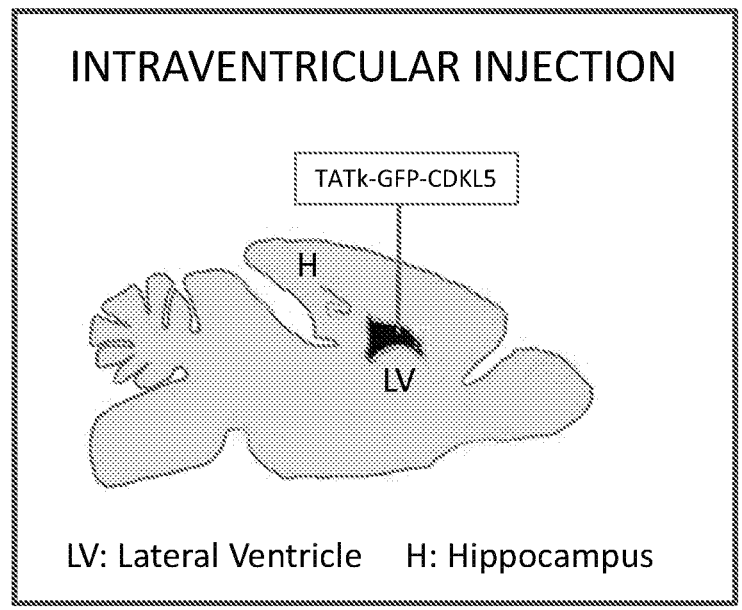

FIG. 19 demonstrates the placement of the cannula for the intraventricular administration of the TATk-GFP-CDKL5 fusion protein to mice.

Figure 20:
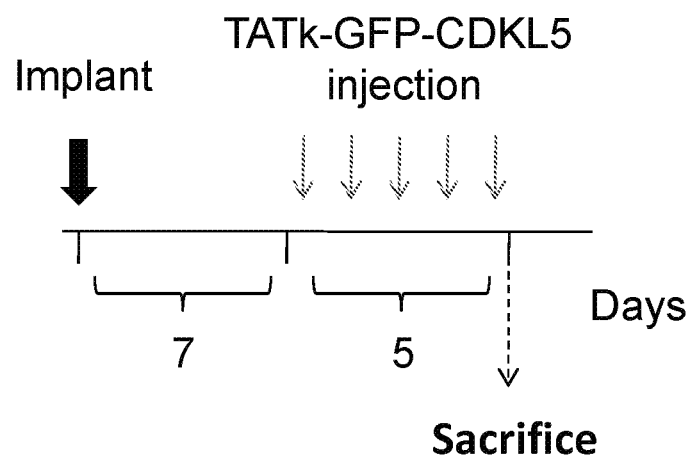

FIG. 20 shows a cartoon depicting the implant and the fusion protein injection schedule for the study demonstrated in FIGS. 21-33.

Figures 21A, 21B, 21C:
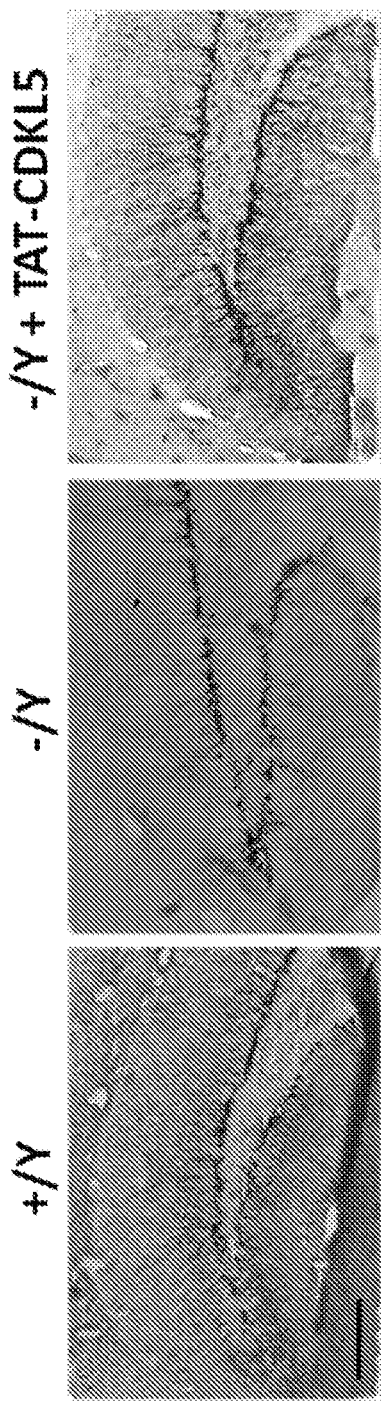

FIGS. 21A-21C show images of hippocampal dentate gyrus sections immunostained for DCX demonstrating reduced neurite length and number of newborn granule cells in CDKL5 knockout mice as compared to wild-type mice (FIGS. 21B and 21A, respectively). TATk-GFP-CDKL5 fusion protein administered intraventricularly on five consecutive days was observed to increase neurite length and number of newborn granule cells in CDKL5 knockout mice (FIG. 21C) to levels similar to wild-type (FIG. 21A). Scale bar=70 μm.

Figures 22A, 22B, 22C:
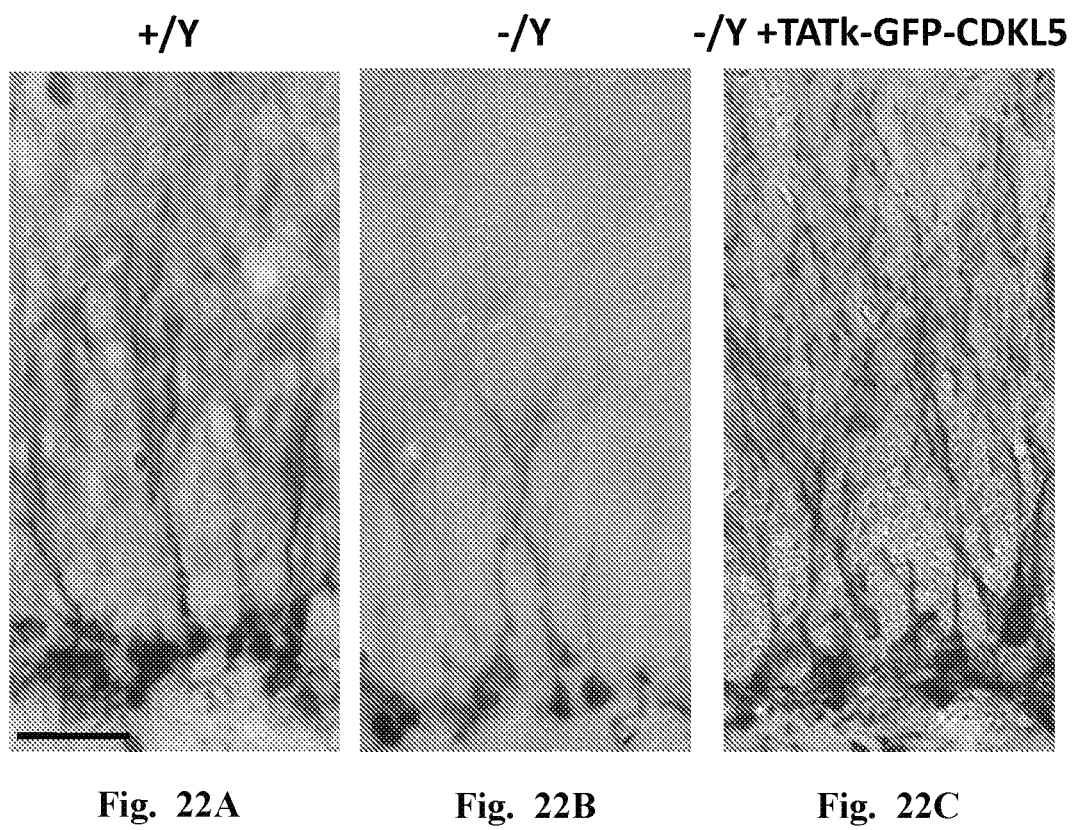

FIGS. 22A-22C illustrate magnifications of the images in FIG. 21 at the level of the granule layer of the dentate gyrus. Scale bar=25 μm.

Figures 23A, 23B, 23C:
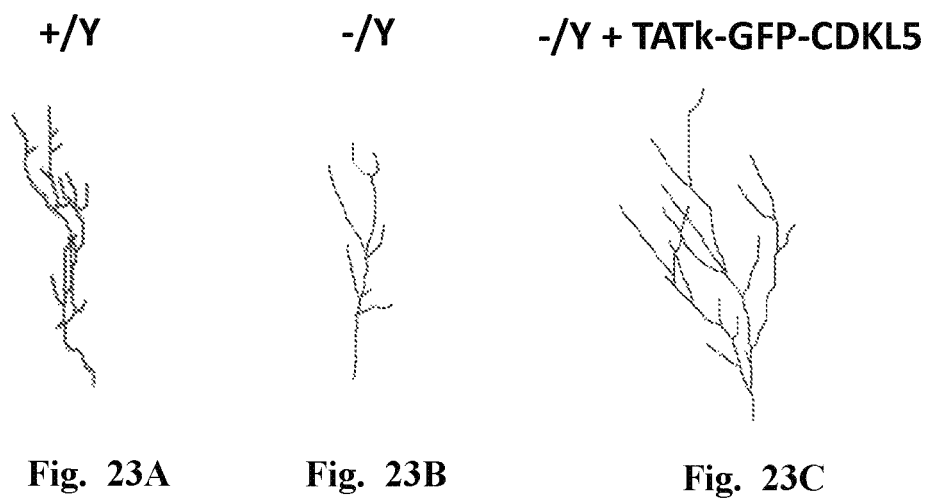

FIGS. 23A-23B show examples of the reconstructed dendritic tree of newborn granule cells of wild-type (+/Y) (FIG. 23A), CDKL5 knockout mice (−/Y) (FIG. 23B), and CDKL5 knockout male mice treated with a TATk-GFP-CDKL5 fusion protein via intraventricular injections given once a day for 5 consecutive days (−/Y+TATk-GFP-CDKL5) (FIG. 23C).

Figures 24A, 24B:
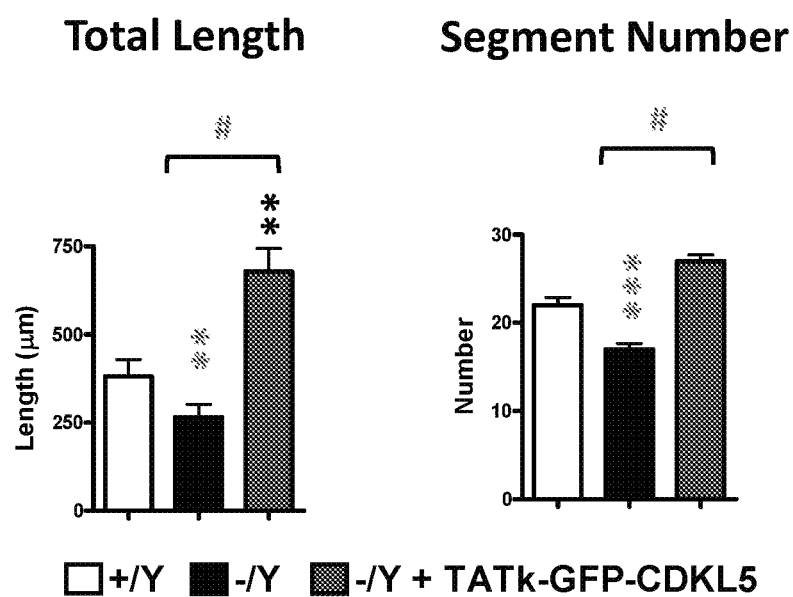

FIGS. 24A-24B show graphs demonstrating quantification of the mean total dendritic length (FIG. 24A), and mean number of dendritic segments (FIG. 24B) of newborn granule cells (DCX-positive cells) of the dentate gyrus of wild-type male mice (+/Y), CDKL5 knockout male mice (−/Y), and CDKL5 knockout male mice treated with TATk-GFP-CDKL5 fusion protein via intraventricular injections given once a day for 5 consecutive days (−/Y+TATk-GFP-CDKL5). Values represent mean±SE.  $p<0.01$; * $p<0.001$ as compared to +/Y; # $p<0.05$ as compared to the −/Y samples (Bonferroni's test after ANOVA).

Figure 25A:
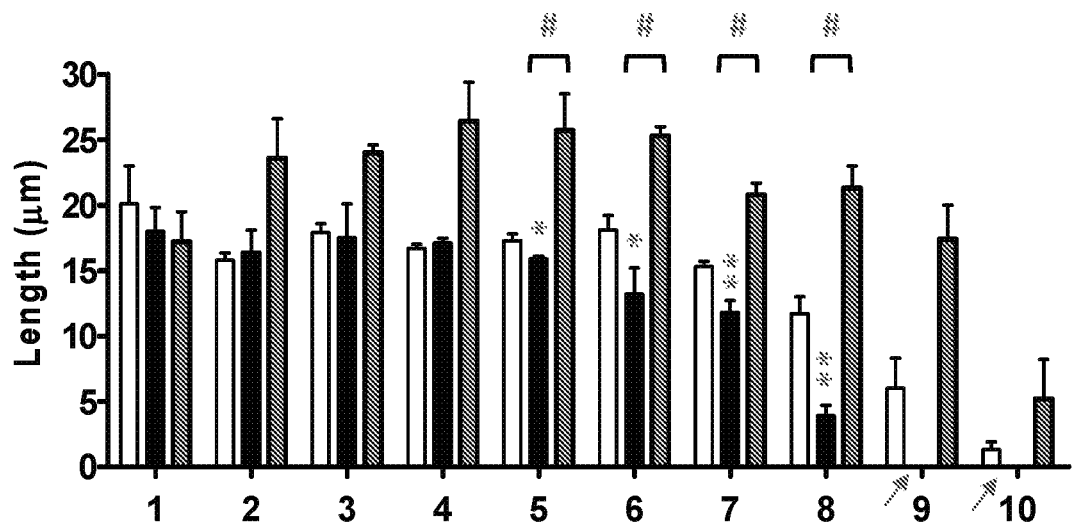
Figure 25B:
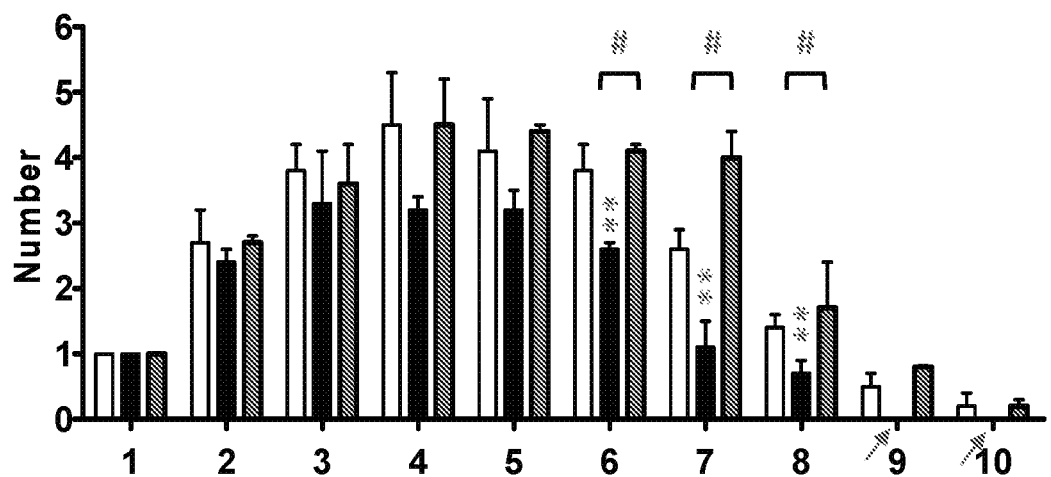

FIGS. 25A-25B show graphs demonstrating quantification of the mean length (FIG. 25A) and mean number (FIG. 25B) of branches of the different orders of newborn granule cells of the dentate gyrus of wild-type male mice (+/Y), CDKL5 knockout male mice (−/Y), and CDKL5 knockout male mice treated with TATk-GFP-CDKL5 fusion protein via intraventricular injections given once a day for 5 consecutive days (−/Y+TATk-GFP-CDKL5). Values represent mean±SE. * $p<0.05$; ** $p<0.01$ as compared to +/Y; # $p<0.05$ as compared to the −/Y samples (Bonferroni's test after ANOVA).

Figure 26:
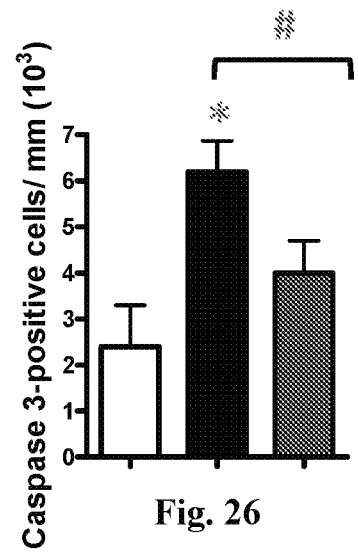

FIG. 26 shows a graph demonstrating quantification of apoptotic cells (caspase-3 positive cells) in wild-type male mice (+/Y), CDKL5 knockout male mice (−/Y), and CDKL5 knockout male mice treated with TATk-GFP-CDKL5 fusion protein via intraventricular injections given once a day for 5 consecutive days (−/Y+TATk-GFP-CDKL5). Values represent mean±SE. * $P<0.05$ as compared to +/Y; # $p<0.05$ as compared to the −/Y samples (Bonferroni's test after ANOVA).

Figure 27:
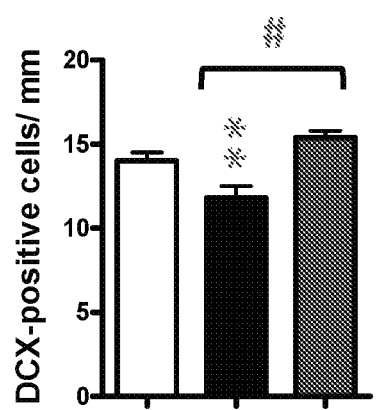

FIG. 27 shows a graph demonstrating quantification of the number of DCX positive cells in the DG of wild-type male mice (+/Y), CDKL5 knockout male mice (−/Y), and CDKL5 knockout male mice treated with TATk-GFP-CDKL5 fusion protein via intraventricular injections given once a day for 5 consecutive days (−/Y+TATk-GFP-CDKL5). Data are expressed as number of cells/mm2* $p<0.05$ as compared to +/Y; # $p<0.05$ as compared to the −/Y samples (Bonferroni's test after ANOVA).

Figures 28A, 28B, 28C:
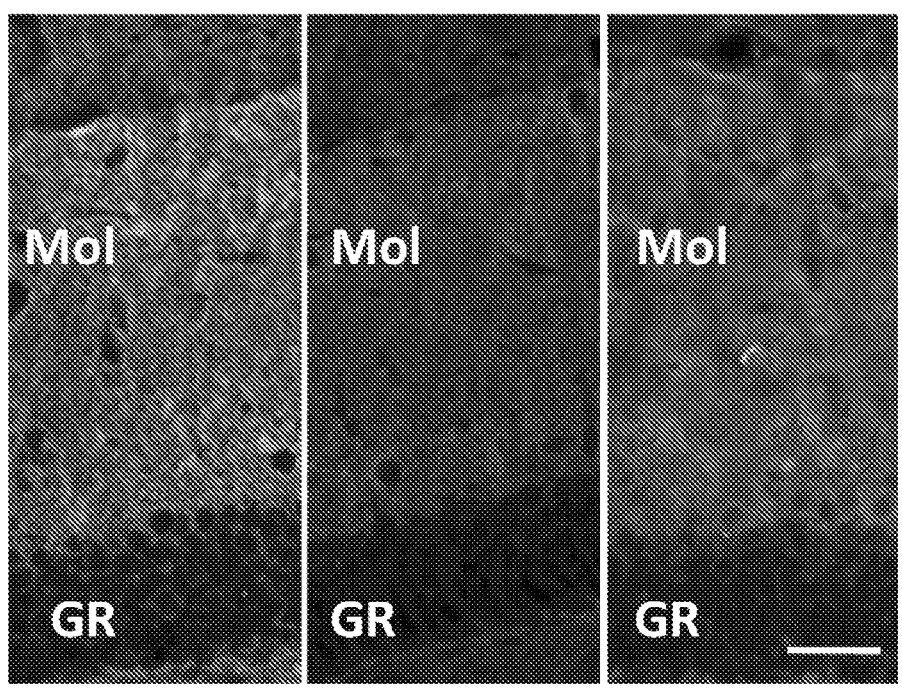

FIGS. 28A-28C show representative images demonstrating brain sections processed for synaptophysin (SYN) immunofluorescence from the molecular layer of the dentate gryrus (DG) from a wild-type male mouse (+/Y) (FIG. 28A), a CDKL5 knockout male mouse (−/Y) (FIG. 28B), and a CDKL5 knockout male mouse treated with TATk-GFP-CDKL5 fusion protein via intraventricular injections given once a day for 5 consecutive days (−/Y+TATk-GFP-CDKL5) (FIG. 28C). Scale bare=80 μm. Abbreviation: GR, granular layer; Mol, molecular layer.

Figures 29A, 29B, 29C:
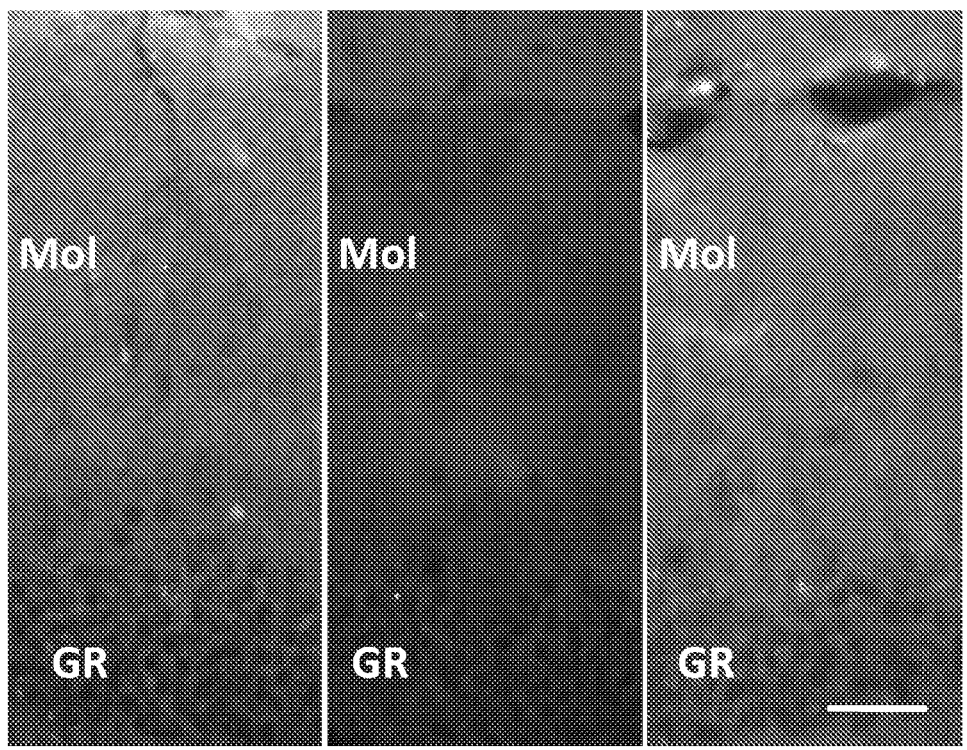

FIGS. 29A-29C show representative images demonstrating brain sections processed for phospho-AKT (P-AKT) immunofluorescence from the molecular layer of the dentate gryrus (DG) from a wild-type male mouse (+/Y) (FIG. 29A), a CDKL5 knockout male mouse (−/Y) (FIG. 29B), and a CDKL5 knockout male mouse treated with TATk-GFP-CDKL5 fusion protein via intraventricular injections given once a day for 5 consecutive days (−/Y+TATk-GFP-CDKL5) (FIG. 29C). Scale bare=80 μm. Abbreviation: GR, granular layer; Mol, molecular layer.

Figure 30A:
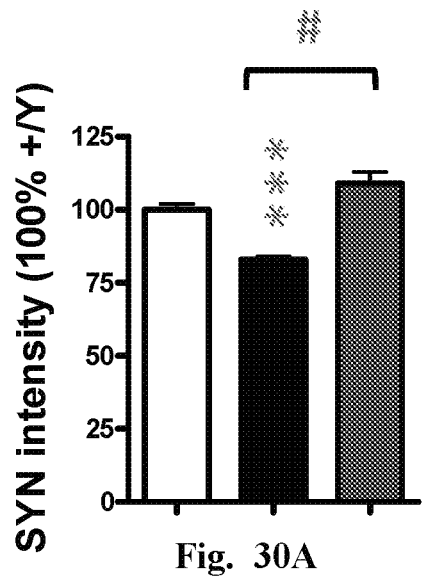
Figure 30B:
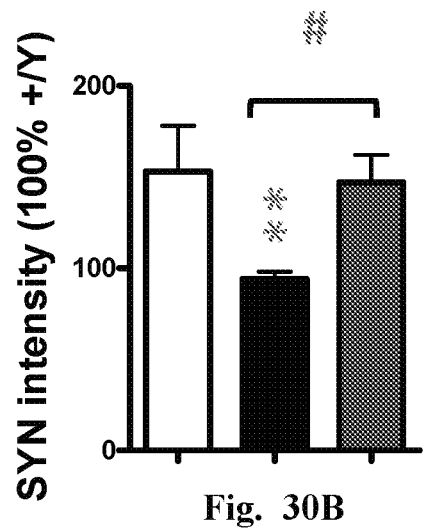

FIGS. 30A-30B show graphs demonstrating the quantification of synaptophysin (SYN) optical density in the molecular layer of the hippocampus (FIG. 30A) and layer III of the cortex (FIG. 30B) in wild-type male mice (+/Y), CDKL5 knockout male mice (−/Y), and CDKL5 knockout male mice treated with TATk-GFP-CDKL5 fusion protein via intraventricular injections given once a day for 5 consecutive days (−/Y+TAT-GFP-CDKL5). Data are given as fold difference vs. the corresponding zone of the molecular layer or cortex of wild type mice. Values represent mean±SD.  $p<0.01$; * $p<0.001$ as compared to +/Y; # $p<0.05$ as compared to the −/Y samples (Bonferroni's test after ANOVA).

Figure 31A:
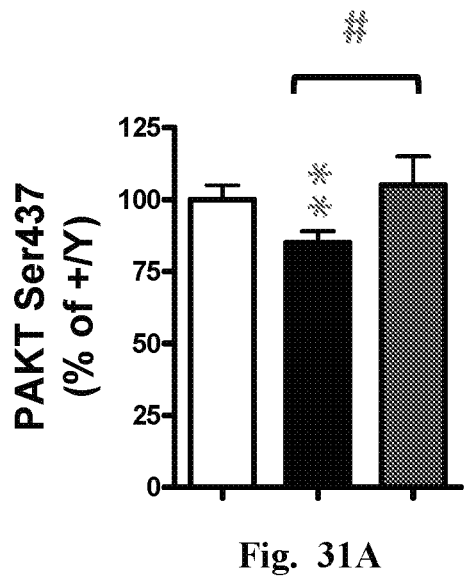
Figure 31B:
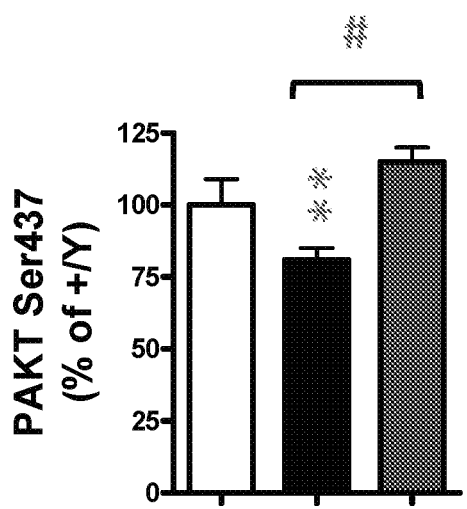

FIGS. 31A-31B show graphs demonstrating the quantification of the optical density of Ser437 phosphorylated-AKT (PAKT) in the molecular layer of the hippocampus (FIG. 31A) and layer V of the cortex (FIG. 31B) in wild-type male mice (+/Y), CDKL5 knockout male mice (−/Y), and CDKL5 knockout male mice treated with TATk-GFP-CDKL5 fusion protein via intraventricular injections given once a day for 5 consecutive days (−/Y+TATk-GFP-CDKL5). Data are given as fold difference vs. the corresponding zone of the molecular layer or cortex of wild type mice. Values represent mean±SD. ** $p<0.01$ as compared to +/Y; # $p<0.01$ as compared to the −/Y samples (Bonferroni's test after ANOVA).

Figure 32:
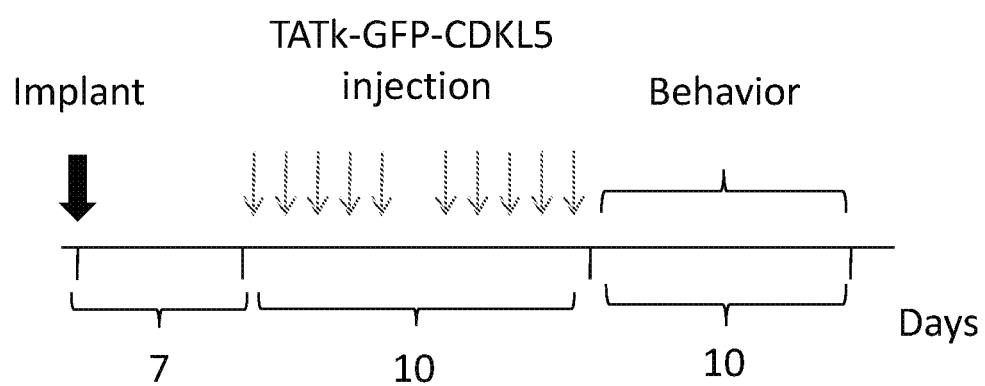
Figure 33:
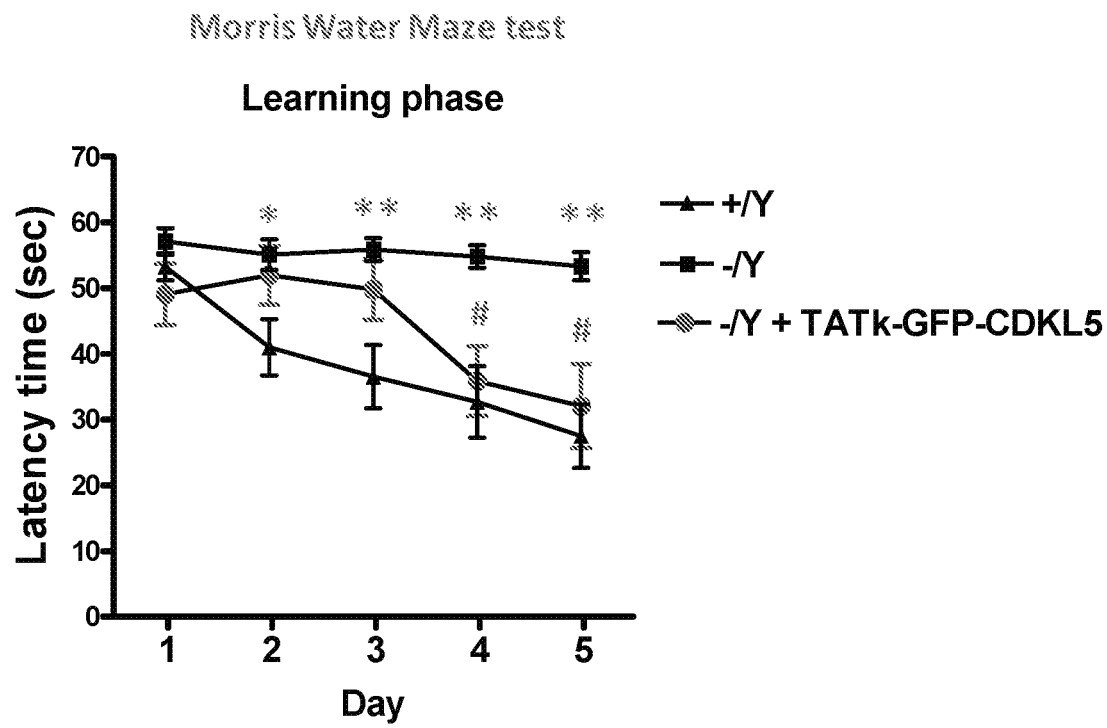

FIG. 32 shows a cartoon depicting the implant and the fusion protein injection schedule for the behavioral study demonstrated in FIGS. 33-34.

FIG. 33 shows a graph demonstrating the quantification of the learning phase as determined via the Morris Water Maze test in wild-type male mice (+/Y; n=8), CDKL5 knockout male mice (−/Y; n=8), and CDKL5 knockout male mice treated with a TATk-GFP-CDKL5 fusion protein (−/Y+TATk-GFP-CDKL5; n=6). Values represent mean±SE. * $P<0.05$, ** $P<0.01$ as compared to the untreated wild-type condition and # $P<0.01$ as compared to the untreated CDKL5 knockout condition as tested with Fisher LSD after ANOVA.

Figures 34A, 34B:
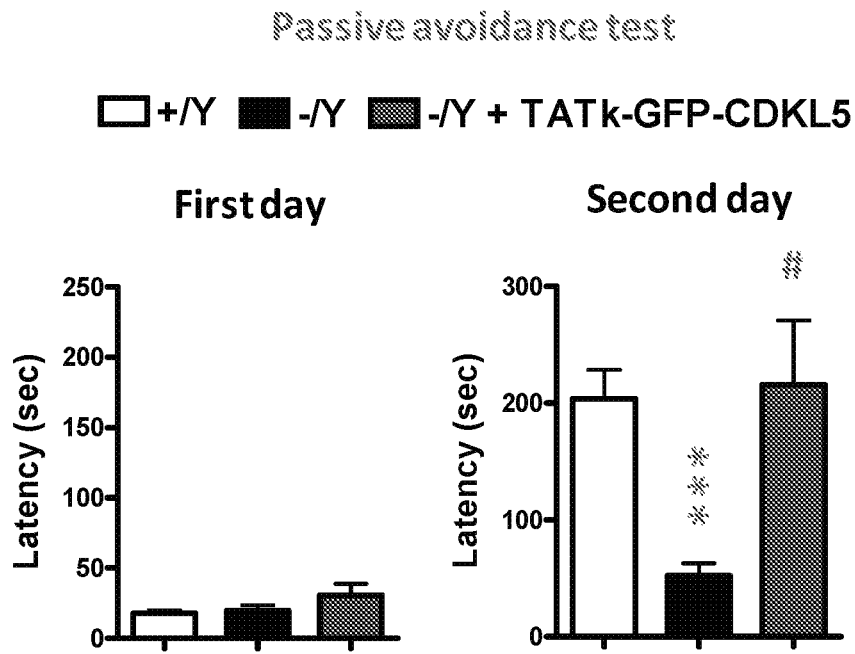

FIGS. 34A-34B show graphs demonstrating memory ability as determined by a passive avoidance test in wild-type male mice (+/Y; n=8), CDKL5 knockout male mice (−/Y; n=8), and CDKL5 knockout male mice treated with a TATk-GFP-CDKL5 fusion protein (−/Y+TATk-GFP- CDKL5; n=6). Graphs show the latency time for entering the dark compartment on the first day (FIG. 34A) and on the second day (FIG. 34B) of the behavioral procedure. Values represent mean±SE. *** $P<0.001$ as compared to the untreated wild-type condition and # $P<0.01$ as compared to the untreated CDKL5 knockout condition as tested with Fisher LSD after ANOVA.

Figure 35A:
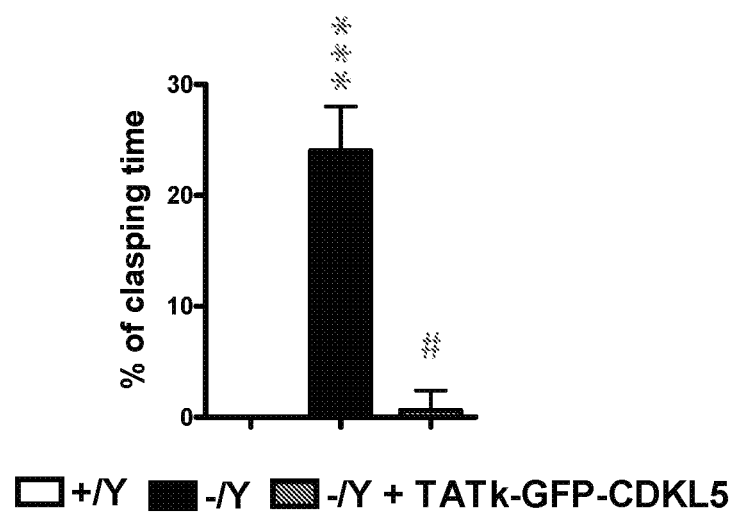
Figure 35B:
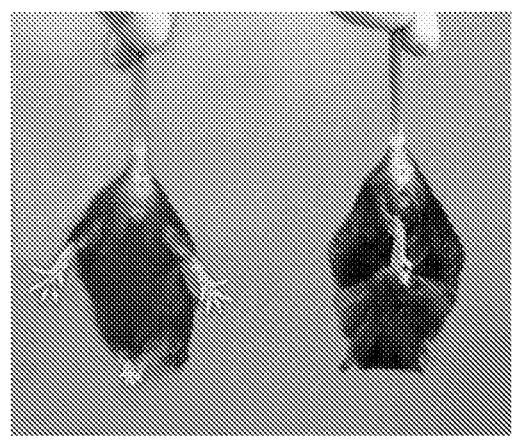

FIGS. 35A-35B show a graph demonstrating quantification of motor ability as determined by a clasping test in which total amount of time spent limb clasping during a 2 minute interval was measured in in wild-type male mice (+/Y; n=8), CDKL5 knockout male mice (−/Y; n=8), and CDKL5 knockout male mice treated with a TATk-GFP-CDKL5 fusion protein (−/Y+TATk-CDKL5; n=8) according to the injection schedule in FIG. 32. Values represent mean±SD. ***$p<0.001$ as compared to +/Y; # $p<0.001$ as compared to the −/Y samples (Bonferroni's test after ANOVA).

Figure 36:
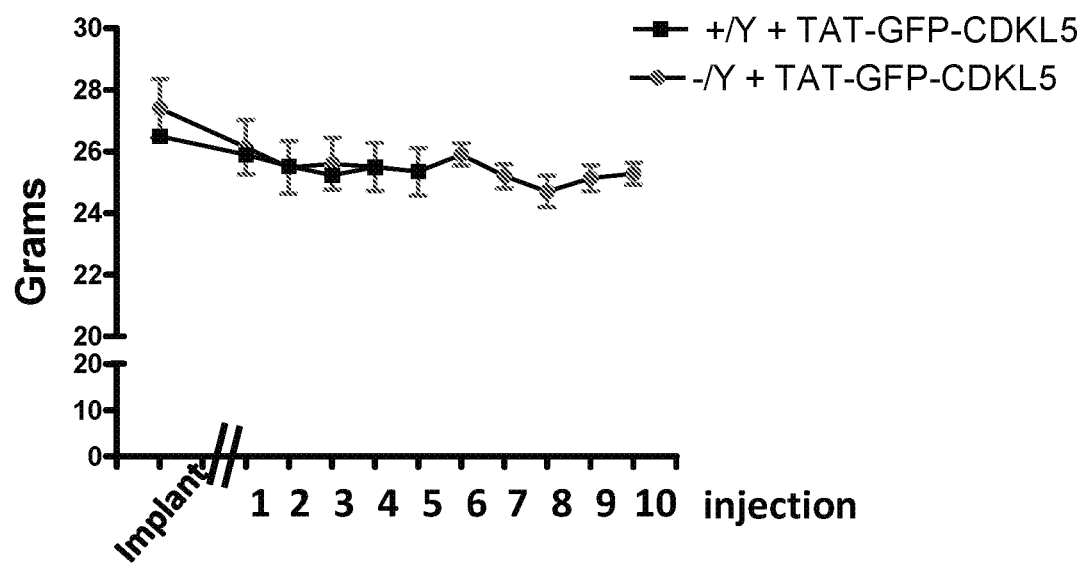

FIG. 36 demonstrates body weight (in grams) of wild-type (+/Y) and knockout (−/Y) mice treated with a TATk-GFP-CDKL5 fusion protein according to the treatment schedule of FIG. 20 (+/Y; n=8) or FIG. 32 (−/Y; n=6). Mice were left to recover for 7 days after cannula implantation.

DETAILED DESCRIPTION

Provided herein are TATk-CDKL5 fusion protein compositions and formulations and methods for their use in the treatment of CDKL5-mediated disease and disorders, particularly disorders and diseases due to CDKL5 mutations and/or deficiencies. Also provided herein are methods for producing TATk-CDKL5 fusion protein compositions and formulations. These methods provide for improved experimental tools for the research of CDKL5-mediated neurological disorders as well as improved treatment options for patients suffering disorders related to CDKL5 dysfunction.

Definitions

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein "biodegradable" generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "hydrophilic", as used herein, refers to substances that have strongly polar groups that readily interact with water.

The term "hydrophobic", as used herein, refers to substances that lack an affinity for water; tending to repel and not absorb water as well as not dissolve in or mix with water.

The term "lipophilic", as used herein, refers to compounds having an affinity for lipids.

The term "amphiphilic", as used herein, refers to a molecule combining hydrophilic and lipophilic (hydrophobic) properties.

As used herein, "about," "approximately," and the like, when used in connection with a numerical variable, generally refers to the value of the variable and to all values of the variable that are within the experimental error (e.g., within the 95% confidence interval for the mean) or within +/−10% of the indicated value, whichever is greater.

As used herein, "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included.

As used herein, "composition" refers to a combination of active agent and at least one other compound or molecule, inert (for example, a detectable agent or label) or active, such as an adjuvant.

As used herein, "control" is an alternative subject or sample used in an experiment for comparison purpose and included to minimize or distinguish the effect of variables other than an independent variable.

As used herein, "positive control" refers to a "control" that is designed to produce the desired result, provided that all reagents are functioning properly and that the experiment is properly conducted.

As used herein, "negative control" refers to a "control" that is designed to produce no effect or result, provided that all reagents are functioning properly and that the experiment is properly conducted. Other terms that are interchangeable with "negative control" include "sham," "placebo," and "mock."

As used herein, "culturing" refers to maintaining cells under conditions in which they can proliferate and avoid senescence as a group of cells. "Culturing" can also include conditions in which the cells also or alternatively differentiate.

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "overexpressed" or "overexpression" refers to an increased expression level of an RNA or protein product encoded by a gene as compared to the level of expression of the RNA or protein product in a normal or control cell.

As used herein, "underexpressed" or "underexpression" refers to decreased expression level of an RNA or protein product encoded by a gene as compared to the level of expression of the RNA or protein product in a normal or control cell.

As used herein, "effective amount" is an amount sufficient to effect beneficial or desired biological, emotional, medical, or clinical response of a cell, tissue, system, animal, or human. An effective amount can be administered in one or more administrations, applications, or dosages. The term also includes within its scope amounts effective to enhance normal physiological function.

The terms "sufficient" and "effective", as used interchangeably herein, refer to an amount (e.g. mass, volume, dosage, concentration, and/or time period) needed to achieve one or more desired result(s). For example, a therapeutically effective amount refers to an amount needed to achieve one or more therapeutic effects.

As used herein, "expansion" or "expanded" in the context of cell refers to an increase in the number of a characteristic cell type, or cell types, from an initial population of cells, which may or may not be identical. The initial cells used for expansion need not be the same as the cells generated from expansion. For instance, the expanded cells may be produced by ex vivo or in vitro growth and differentiation of the initial population of cells.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

As used herein, "concentrated" refers to a molecule, including but not limited to a polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "diluted" refers to a molecule, including but not limited to a polynucleotide, peptide, polypeptide, protein, antibody, or fragments thereof, that is distinguishable from its naturally occurring counterpart in that the concentration or number of molecules per volume is less than that of its naturally occurring counterpart.

As used herein, "separated" refers to the state of being physically divided from the original source or population such that the separated compound, agent, particle, or molecule can no longer be considered part of the original source or population.

As used herein, "mammal," for the purposes of treatments, refers to any animal classified as a mammal, including human, domestic and farm animals, nonhuman primates, and zoo, sports, or pet animals, such as, but not limited to, dogs, horses, cats, and cows.

As used interchangeably herein, "subject," "individual," or "patient" refers to a vertebrate organism.

As used herein, "substantially pure cell population" refers to a population of cells having a specified cell marker characteristic and differentiation potential that is about 50%, preferably about 75-80%, more preferably about 85-90%, and most preferably about 95% of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that do not display a specified marker characteristic and differentiation potential under designated assay conditions.

As used herein, "therapeutic" refers to treating, healing, and/or ameliorating a disease, disorder, condition, or side effect, or to decreasing in the rate of advancement of a disease, disorder, condition, or side effect. The term also includes within its scope enhancing normal physiological function, palliative treatment, and partial remediation of a disease, disorder, condition, side effect, or symptom thereof. The disease or disorder can be a CDKL5 deficiency and/or Rett Syndrome.

The terms "treating" and "treatment" as used herein refer generally to obtaining a desired pharmacological and/or physiological effect. The effect may be prophylactic in terms of preventing or partially preventing a disease, symptom or condition thereof, such as disease or disorders resulting from CDKL5 mutations and/or deficiencies, the CDKL5 variant of Rett syndrome, or other CDKL5-mediated neurological disorder, and/or may be therapeutic in terms of a partial or complete cure of a disease, condition, symptom or adverse effect attributed to the disease, disorder, or condition. The term "treatment" as used herein covers any treatment of CDKL5-mediated neurological disorder in a mammal, particularly a human, and includes: (a) preventing the disease from occurring in a subject which may be predisposed to the disease but has not yet been diagnosed as having it, (b) inhibiting the disease, i.e., arresting its development; or (c) relieving the disease, i.e., mitigating or ameliorating the disease and/or its symptoms or conditions. The term "treatment" as used herein refers to both therapeutic treatment and prophylactic or preventative measures. Those in need of treatment include those already with the disorder as well as those in which the disorder is to be prevented.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "preventative" and "prevent" refers to hindering or stopping a disease or condition before it occurs, even if undiagnosed, or while the disease or condition is still in the sub-clinical phase.

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "tangible medium of expression" refers to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "chemotherapeutic agent" or "chemotherapeutic" refer to a therapeutic agent utilized to prevent or treat cancer.

As used herein, "matrix" refers to a material, in which one or more specialized structures, molecules, or compositions, are embedded.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

As used herein, "immunomodulator," refers to an agent, such as a therapeutic agent, which is capable of modulating or regulating one or more immune function or response.

As used herein, "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, and FR4. The variable regions of the heavy and light chains contain a binding domain that interacts with an antigen.

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans). "Subject" may also be a cell, a population of cells, a tissue, an organ, or an organism, preferably to human and constituents thereof.

As used herein, "patient" refers to an organism, host, or subject in need of treatment.

As used herein, "protein" as used herein refers to a large molecule composed of one or more chains of amino acids in a specific order. The term protein is used interchangeable with "polypeptide." The order is determined by the base sequence of nucleotides in the gene coding for the protein. Proteins are required for the structure, function, and regulation of the body's cells, tissues, and organs. Each protein has a unique function.

As used herein, "substantially pure" means an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein.

As used herein, "deoxyribonucleic acid (DNA)" and "ribonucleic acid (RNA)" generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "nucleic acid sequence" and "oligonucleotide" also encompasses a nucleic acid and polynucleotide as defined above.

As used herein, "DNA molecule" includes nucleic acids/polynucleotides that are made of DNA.

As used herein, "gene" refers to a hereditary unit corresponding to a sequence of DNA that occupies a specific location on a chromosome and that contains the genetic instruction for a characteristic(s) or trait(s) in an organism.

As used herein, the term "recombinant" generally refers to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc.). Recombinant also refers to the polypeptide encoded by the recombinant nucleic acid. Non-naturally occurring nucleic acids or polypeptides include nucleic acids and polypeptides modified by man.

As used herein, "fusion protein" refers to a protein formed from the combination of at least two different proteins or protein fragments. A fusion protein is encoded by a recombinant DNA molecule. As such, a "CDKL5 fusion protein" refers to a recombinant protein having a human CDKL5 polypeptide or variant thereof operatively linked to other polypeptide sequences.

As used herein, "CDKL5 deficiency" refers to any deficiency in the biological function of the protein. The deficiency can result from any DNA mutation in the DNA coding for the protein or a DNA related regulatory region or any change in the function of the protein due to any changes in epigenetic DNA modification, including but not limited to DNA methylation or histone modification, any change in the secondary, tertiary, or quaternary structure of the CDKL5 protein, or any change in the ability of the CDKL5 protein to carry out its biological function as compared to a wild-type or normal subject.

As used herein, "Rett syndrome variant," "variant of Rett syndrome," and the like refers to an atypical form of Rett syndrome with similar clinical signs to Rett syndrome but an unknown etiology.

As used herein, "CDKL5 mutation" refers to any change in the nucleotide sequence of the coding region of the CDKL5 protein.

As used herein, the term "transfection" refers to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome.

As used herein, "transformation" or "transformed" refers to the introduction of a nucleic acid (e.g., DNA or RNA) into cells in such a way as to allow expression of the coding portions of the introduced nucleic acid.

As used herein, "transduced" refers to the direct introduction of a protein into a cell.

As used herein "peptide" refers to chains of at least 2 amino acids that are short, relative to a protein or polypeptide.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. "Variant" includes functional and structural variants.

As used herein, "identity," is a relationship between two or more polypeptide sequences, as determined by comparing the sequences. In the art, "identity" also refers to the degree of sequence relatedness between polypeptide as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, A M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453) algorithm (e.g., NBLAST, and XBLAST). The default parameters are used to determine the identity for the polypeptides of the present disclosure.

As used herein, "plasmid" as used herein refers to a non-chromosomal double-stranded DNA sequence including an intact "replicon" such that the plasmid is replicated in a host cell.

As used herein, the term "vector" or is used in reference to a vehicle used to introduce an exogenous nucleic acid sequence into a cell. A vector may include a DNA molecule, linear or circular (e.g. plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

As used herein, "operatively linked" indicates that the regulatory sequences useful for expression of the coding sequences of a nucleic acid are placed in the nucleic acid molecule in the appropriate positions relative to the coding sequence so as to effect expression of the coding sequence. This same definition is sometimes applied to the arrangement of coding sequences and transcription control elements (e.g. promoters, enhancers, and termination elements), and/or selectable markers in an expression vector.

As used herein, "wild-type" is the typical form of an organism, variety, strain, gene, protein, or characteristic as it occurs in nature, as distinguished from mutant forms that may result from selective breeding or transformation with a transgene.

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein, "purified" or "purify" is used in reference to a nucleic acid sequence, peptide, or polypeptide that has increased purity relative to the natural environment.

As used herein, "differentiate" or "differentiation," refers to the process by which precursor or progenitor cells (e.g., neuronal progenitor cells) differentiate into specific cell types (e.g., neurons).

As used herein, "dose," "unit dose," or "dosage" refers to physically discrete units suitable for use in a subject, each unit containing a predetermined quantity of the CDKL5 fusion protein, a composition containing the CDKL5 fusion protein, and/or a pharmaceutical formulation thereof calculated to produce the desired response or responses in association with its administration.

As used herein, "specific binding partner" or "binding partner" is a compound or molecule to which a second compound or molecule binds with a higher affinity than all other molecules or compounds.

As used herein, "specifically binds" or "specific binding" refers to binding that occurs between such paired species such as enzyme/substrate, receptor/agonist or antagonist, antibody/antigen, lectin/carbohydrate, oligo DNA primers/DNA, enzyme or protein/DNA, and/or RNA molecule to other nucleic acid (DNA or RNA) or amino acid, which may be mediated by covalent or non-covalent interactions or a combination of covalent and non-covalent interactions. When the interaction of the two species produces a non-covalently bound complex, the binding that occurs is typically electrostatic, hydrogen-bonding, or the result of lipophilic interactions. Accordingly, "specific binding" occurs between a paired species where there is interaction between the two which produces a bound complex having the characteristics of an antibody/antigen, enzyme/substrate, DNA/DNA, DNA/RNA, DNA/protein, RNA/protein, RNA/amino acid, receptor/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein, "anti-infective" refers to compounds or molecules that can either kill an infectious agent or inhibit it from spreading. Anti-infectives include, but are not limited to, antibiotics, antibacterials, antifungals, antivirals, and antiprotozoans.

As used herein, "wild-type" is the typical form of an organism, variety, strain, gene, protein, or characteristic as it occurs in nature, as distinguished from mutant forms that may result from selective breeding or transformation with a transgene.

As used herein "induces," "inducing," or "induced" refers to activating or stimulating a process or pathway within a cell, such as endocytosis, secretion, and exocytosis.

As used herein, "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups.

As used herein, "therapeutically effective amount" refers to the amount of a CDKL5-fusion protein, a composition containing a CDKL5 fusion protein, a pharmaceutical formulation thereof, auxiliary agent, or secondary agent described herein that will elicit the biological or medical response of a tissue, system, animal, or human that is being sought by the researcher, veterinarian, medical doctor or other clinician. "Therapeutically effective amount" includes that amount of a CDKL5-fusion protein, a composition containing a CDKL5 fusion protein, a pharmaceutical formulation thereof that, when administered alone or co-administered with a secondary agent, is sufficient to prevent development of, reduce or alleviate to some extent, one or more of the symptoms of CDKL5 deficiency and/or Rett syndrome. "Therapeutically effect amount" includes that amount of CDKL5-fusion protein, a composition containing a CDKL5 fusion protein, a pharmaceutical formulation thereof that, when administered alone or co-administered with a secondary agent, is sufficient to increase neuron survival, neuron number, neurite growth, elongation, and/or branch density in a region of the brain of a subject as compared to a control. "Therapeutically effect amount" includes that amount of CDKL5-fusion protein, a composition containing a CDKL5 fusion protein, a pharmaceutical formulation thereof that, when administered alone or co-administered with a secondary agent, is sufficient to increase learning ability in a subject as compared to a control. "Therapeutically effect amount" includes that amount of CDKL5-fusion protein, a composition containing a CDKL5 fusion protein, a pharmaceutical formulation thereof that, when administered alone or co-administered with a secondary agent, is sufficient to increase memory ability in a subject as compared to a control. "Therapeutically effect amount" includes that amount of CDKL5-fusion protein, a composition containing a CDKL5 fusion protein, a pharmaceutical formulation thereof that, when administered alone or co-administered with a secondary agent, is sufficient to improve motor function in a subject as compared to a control. "Therapeutically effect amount" includes that amount of CDKL5-fusion protein, a composition containing a CDKL5 fusion protein, a pharmaceutical formulation thereof that, when administered alone or co-administered with a secondary agent, is sufficient to restore learning ability, memory ability, and/or motor function to levels that are substantially similar to wild-type or normal levels. "Therapeutically effect amount" includes that amount of CDKL5-fusion protein, a composition containing a CDKL5 fusion protein, a pharmaceutical formulation thereof that, when administered alone or co-administered with a secondary agent, is sufficient to restore neuron number, neuron survival, neurite growth, neurite elongation, neurite branch number, and/or neurite branch density in a region of the brain to levels that are substantially similar to wild-type or normal levels. The therapeutically effective amount will vary depending on the exact chemical structure of the CDKL5-fusion protein, a composition containing a CDKL5 fusion protein, a pharmaceutical formulation thereof, the CDKL5 deficiency, Rett syndrome or symptom thereof being treated, the route of administration, the time of administration, the rate of excretion, the drug combination, the judgment of the treating physician, the dosage form, and the age, weight, general health, sex and/or diet of the subject to be treated.

As used herein, "synergistic effect," "synergism," or "synergy" refers to an effect arising between two or more molecules, compounds, substances, factors, or compositions that is greater than or different from the sum of their individual effects.

As used herein, "additive effect" refers to an effect arising between two or more molecules, compounds, substances, factors, or compositions that is equal to or the same as the sum of their individual effects.

Unless otherwise defined herein, all technical and scientific terms used herein have the same meaning as commonly understood by one of ordinary skill in the art.

Discussion

TATk-CDKL5 Fusion Genes and Proteins

Fusion Genes and Proteins

Disclosed herein are recombinant cDNA sequences, which code for various CDKL5 fusion proteins containing a modified TAT (TATk) sequence. In one embodiment the fusion protein contains a human CDKL5 polypeptide operatively coupled to a TATk polypeptide. The cDNA sequence, which codes for the CDKL5 fusion protein, can have a sequence according to any one of SEQ ID NOs: 2, 7, 9, 11, 13, or a variant thereof described herein. The CDKL5 fusion protein can have a polypeptide sequence according to any one of SEQ ID NOs: 8, 10, 12, 14, or a variant thereof describe herein.

In some embodiments, the human CDKL5 cDNA sequence can be according to SEQ ID NOs: 1 or 15. In further embodiments, the human CDKL5 cDNA can be about 90% to about 100%, 80% to about 900%, or about 500 to about 80%, identical to SEQ ID NOs: 1 or 15. In some embodiments, the human CDKL5 cDNA sequence can code for an amino acid sequence according to SEQ ID NO: 2 or 16. In further embodiments, the human CDKL5 cDNA sequence can code for an amino acid sequence that is about 90% to about 100%, 80% to about 90%, or about 50%, to about 80% identical to SEQ ID NO: 2 or 16.

In some embodiments, the human CDKL5 cDNA sequence can be a fragment of at least 12 consecutive nucleotides that are about 90% to 100% identical to 12 consecutive nucleotides in SEQ ID NO: 1. In some embodiments, the human CDKL5 cDNA sequence can be a fragment of at least 12 consecutive nucleotides that are about 80% to 90% identical to 12 consecutive nucleotides in SEQ ID NO: 1. In some embodiments, the cDNA sequence can be a fragment of at least 12 consecutive nucleotides that are about 50% to 80% identical to 12 consecutive nucleotides in SEQ ID NO: 1.

The CDKL5 fusion protein contains a modified transacting activation of transcription (TAT) protein transduction domain (PTD) (hereinafter TATk) operatively coupled to the human CDKL5 polypeptide. The TATk can have a cDNA sequence according to SEQ ID NO: 3 and an amino acid sequence according to SEQ ID NO: 4. TATk is a modified TAT-PTD. Unmodified TAT-PTD mediates the transductions of peptides and proteins into cells. However, unmodified TAT-PTD does not allow TAT-PTD fusion proteins to be secreted by the cell. Unmodified TAT-PTD is cleaved from the fusion protein by furin endoprotease at furin recognition sequences located within unmodified TAT-PTD. In contrast, TATk is modified such that it does not contain the furin recognition sequences. As such, the CDKL5 fusion proteins described herein containing TATk can be secreted in its full form by eukaryotic cells.

In some embodiments, the TATk cDNA sequence can be about 90% to 100% or about 80% to about 90% identical to SEQ ID NO: 3. In some embodiments, the TATk cDNA can code for a polypeptide sequence that is about 900% to 100% or about 80% to about 900% identical to SEQ ID NO: 4.

The CDKL5 fusion protein can optionally contain an Igκ-chain leader sequence to direct the polypeptide down the secretory pathway during production by a cell. In some embodiments, the Igκ-chain leader sequence can be operatively coupled at the N-terminus of the human CDKL5 polypeptide. The Igκ-chain leader sequence can have a cDNA sequence according to SEQ ID NO: 5 or a variant thereof described herein and can have an amino acid sequence according to SEQ ID NO: 6 or variant thereof described herein.

In other embodiments, the Igκ-chain leader sequence cDNA can be about 90% to 100%, about 80% to about 90%, or about 80% to 90% identical to SEQ ID NO: 5. In some embodiments, the Igκ-chain leader sequence can have an amino acid sequence that is about 90% to about 100%, about 80% to about 90%, or about 50% to about 80%° identical to SEQ ID NO: 6.

The CDKL5 fusion protein can optionally contain one or more protein tags operatively coupled to the CDKL5 fusion protein. These types of tags are amino acid sequences that allow for affinity purification, solubilization, chromatographical separation, and/or immunodetection of the fusion protein. Suitable protein tags include, but are not limited to, chitin binding protein (CBP), maltose binding protein (MBP), glutathione-S-transferase (GST), poly(His), thioredoxin (TRX), poly(NANP), FLAG-tag (including any FLAG-tag variant, e.g. 3×FLAG), VS-tag, Myc-tag, HA-tag, S-tag, SBP-Tag, Sftag 1, Softag 3, Tc tag, Xpress tag, Strep-tag, Isopeptag, Spy Tag, Ty tag, Biotin Carboxyl Carrier Protein (BCCP), and Nus tag. A CDKL5 fusion protein cDNA according SEQ ID NO: 7, 9, or 11 having an amino acid sequence according to SEQ ID NO: 8, 10, or 12, respectively, demonstrate non-limiting embodiments of a CDKL5 fusion protein containing a TATk, and Myc-tag and a poly(HIS) tag. A CDKL5 fusion protein cDNA according SEQ ID NO: 13, having an amino acid sequence according to SEQ ID NO: 14 demonstrate a non-limiting embodiment of a CDKL5 fusion protein having a FLAG-tag.

The CDKL5 fusion protein can optionally contain one or more reporter proteins operatively coupled to the CDKL5 polypeptide. Suitable reporter genes include, but are not limited to, fluorescent proteins (e.g. green fluorescent protein (GFP), red fluorescent protein (RFP), yellow fluorescent protein (YFP), blue fluorescent protein (BFP), and cyan fluorescent protein (CFP)), beta-galactosidase, luciferase (bacterial, firefly, and renilla luciferase), antibiotic-resistance genes (e.g. chloramphenicol acetyltransferase, neomycin phosphotransferase, and NPT-II), p-glucuronidase, and alkaline phosphatase. Inclusion of a reporter protein allows, inter alia, for direct and/or indirect characterization of the fusion protein and function of the fusion protein, as well as affinity purification of the protein. The reporter protein can be operatively linked to the N-terminus and/or the C-terminus of the human CDKL5 polypeptide. In other embodiments the reporter protein can be operatively linked to -terminus and/or the C-terminus of the CDKL5 fusion protein. A CDKL5 fusion protein cDNA according SEQ ID NO: 9 or 11 and having an amino acid sequence according to SEQ ID NO: 8 or 10, respectively, demonstrate non-limiting embodiments of a CDKL5 fusion protein containing a fluorescent reporter protein.

Recombinant Vectors

The CDKL5 fusion cDNA sequence can be incorporated into a suitable expression vector. The expression vector can contain one or more regulatory sequences or one or more other sequences used to facilitate the expression of the CDKL5 fusion cDNA. The expression vector can contain one or more regulatory sequences or one or more other sequences used to facilitate the replication of the CDKL5 fusion expression vector. The expression vector can be suitable for expressing the CDKL5 fusion protein in a bacterial cell. In other embodiments, the expression vector can be suitable for expressing the CDKL5 fusion protein in a yeast cell. In further embodiments, the expression vector can be suitable for expressing the CDKL5 fusion protein in a plant cell. In other embodiments, the expression vector can be suitable for expressing the CDKL5 fusion protein in a mammalian cell. In another embodiment, the vector can be suitable for expressing the CDKL5 fusion protein in a fungal cell. Suitable expression vectors are generally known in the heart.

TATk-CDKL5 Protein Production

In some embodiments, the CDKL5 fusion protein is produced in vitro in a cell culture system. The cell culture system can contain one or more bacterial, yeast, fungal, plant, or mammalian cells. In some embodiments, the CDKL5 fusion protein is secreted by the cultured cell(s) into the cell culture media. In other embodiments, the CDKL5 fusion protein is contained within the cytoplasm or a membrane of the cultured cell(s).

Figure 1:
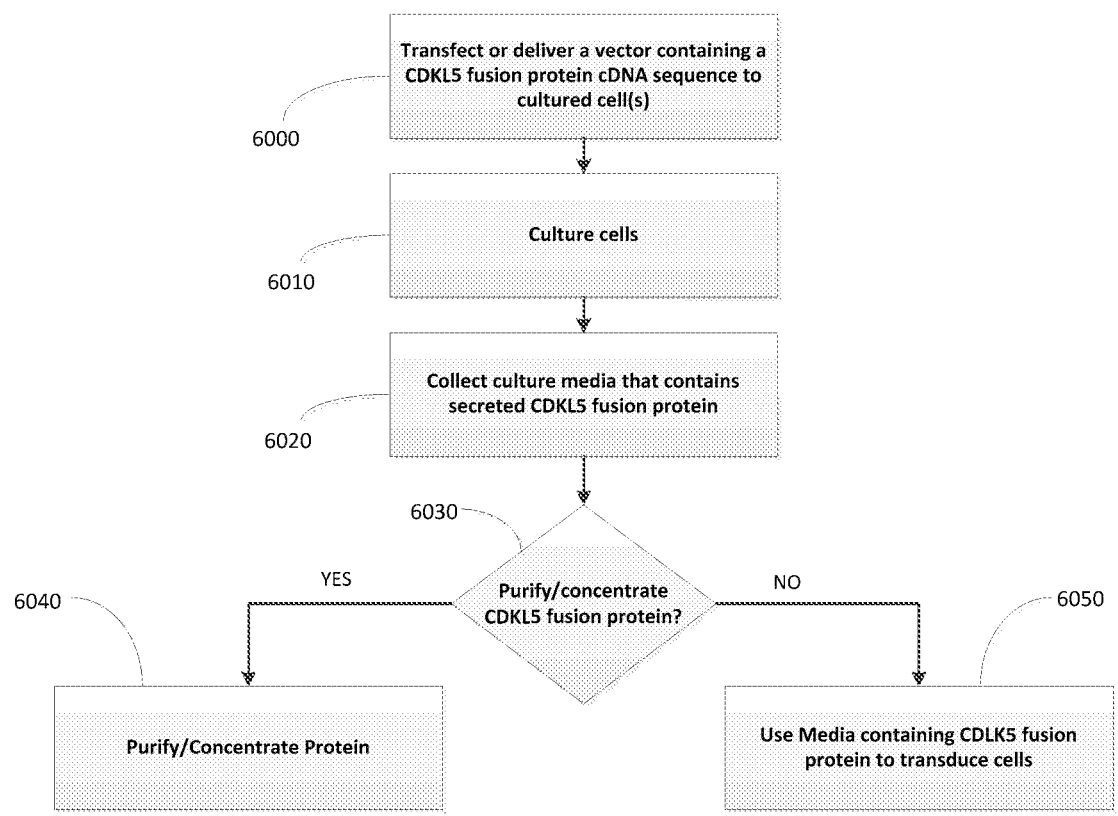
FIG. 1 shows one embodiment of a method to produce a CDKL5 fusion protein, wherein the CDKL5 fusion protein is produced by the cultured cell and secreted into the surrounding culture media.

With that said, attention is directed to FIG. 1, which shows one embodiment of a method to produce a CDKL5 fusion protein, wherein the CDKL5 fusion protein is produced by the cultured cell and secreted into the surrounding culture media. The method begins by transfecting or otherwise delivering a suitable vector containing a CDKL5 fusion protein cDNA sequence to a cell or cells in culture (6000). The cells are then cultured (6010) using generally known methods to allow the transfected cells to produce the CDKL5 fusion protein from the vector and secrete the CDKL5 fusion protein into the surrounding cell culture media. After a suitable amount of time, the culture media that contains the secreted CDKL5 fusion protein is collected (6020). In some embodiments the cells are cultured from about 12 h to about 96 h. At this point, it is determined whether or not the CDKL5 fusion protein needs to be further purified from the culture media (6030). In some embodiments, the media containing the CDKL5 fusion protein is not further purified and is used directly to transduce one or more cells (6050). In other embodiments, the CDKL5 fusion protein is further purified from and/or concentrated in the culture media. In some embodiments, the CDKL5 fusion protein is purified and/or concentrated using a suitable method. Suitable methods include, but are not limited to, affinity purification, size exclusion separation, and chromatographical separation methods.

Figure 2:
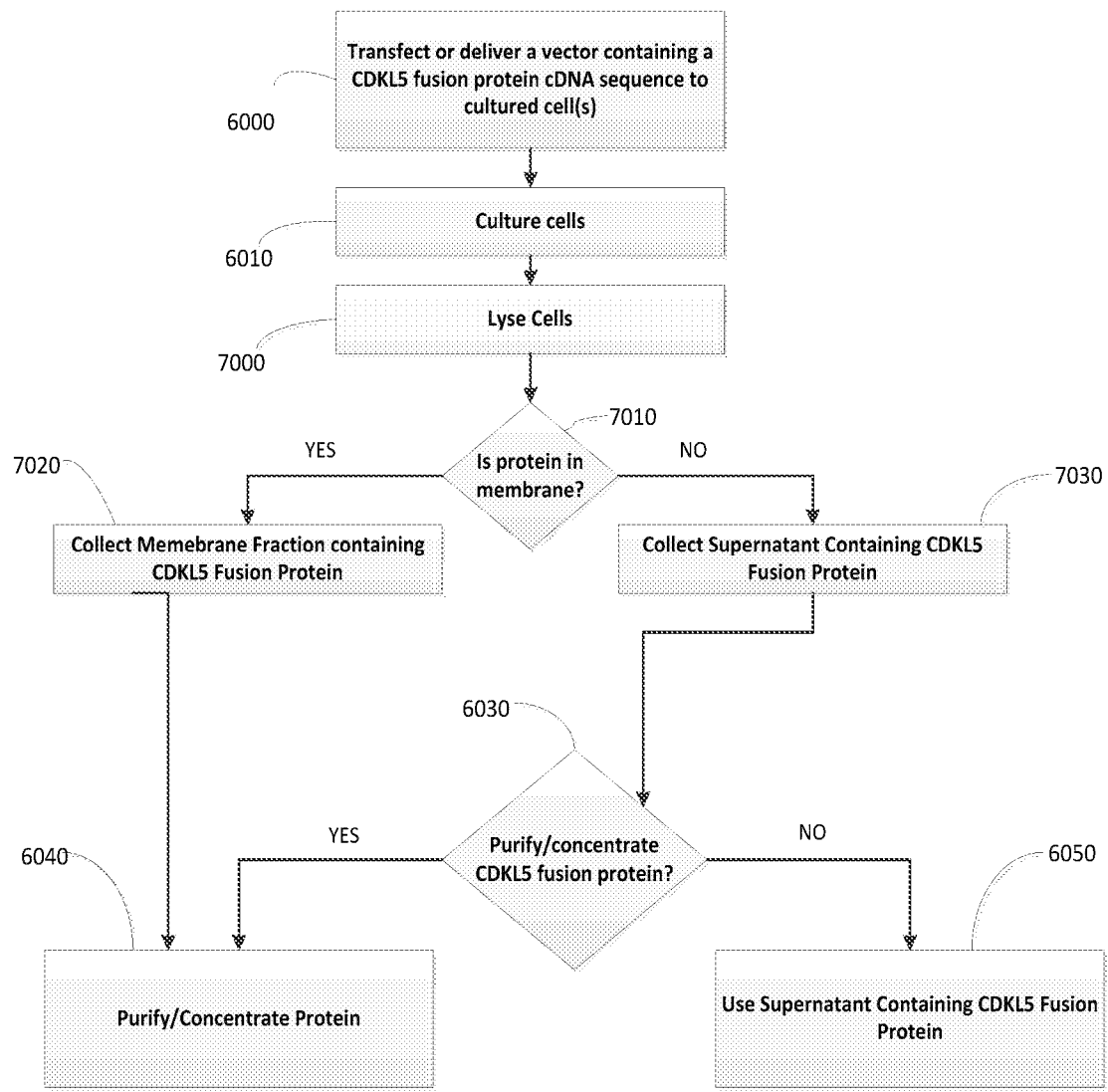
FIG. 2 shows one embodiment of a method of producing a CDKL5 fusion protein wherein the CDKL5 fusion protein is not secreted into the surrounding cell culture media.

With an understanding of a secretory method of production in mind, attention is directed to FIG. 2, which shows one embodiment of a method of producing a CDKL5 fusion protein wherein the CDKL5 fusion protein is not secreted into the surrounding cell culture media. The method begins by transfecting or otherwise delivering a suitable vector containing a CDKL5 fusion protein cDNA sequence to a cell or cells in culture (6000). The cells are then cultured (6010) using generally known methods to allow the transfected cells to produce the CDKL5 fusion protein from the vector. After a suitable amount of time, the cells are lysed using standard methods (7000). In some embodiments, the cells are cultured from 12 h to 96 h before being lysed.

Next it is determined if the CDKL5 fusion protein is integrated within the cell membrane or the cytoplasm (7010). If the CDKL5 fusion protein is in the membrane fraction, then the membrane fraction is collected (7020). After the membrane fraction is collected (7020), the CDKL5 fusion protein is separated from the membrane fraction using suitable method (6040) for purifying and/or concentrating the CDKL5 fusion protein.

In embodiments where the CDKL5 fusion protein is present in the cytoplasm, the supernatant containing the CDKL5 fusion protein is collected (7030). After the supernatant is collected (7030), it is determined if the CDKL5 fusion protein should be further purified and/or concentrated. If it is determined that that the CDKL5 fusion protein should be further purified and/or concentrated, then the CDKL5 fusion protein is purified and/or concentrated using a suitable method (6040). Suitable methods include, but are not limited to, affinity purification, size exclusion separation, and chromatographical separation methods. In other embodiments where it is determined that the CDKL5 should not be further purified and/or concentrated from the supernatant, the supernatant containing the CDKL5 fusion protein is used directly to transduce cells (6050).

Compositions and Formulations containing TATk-CDKL5 Fusion Protein

Also within the scope of this disclosure are compositions and formulations containing a CDKL5 fusion protein as described herein. The composition can be the media or supernatant containing the CDKL5 fusion protein that can be produced according to a method described herein.

The CDKL5 fusion proteins described herein can be provided to a subject in need thereof alone or as such as an active ingredient, in a pharmaceutical formulation. As such, also described herein are pharmaceutical formulations containing an amount of a CDKL5 fusion protein. In some embodiments, the pharmaceutical formulations contain a therapeutically effective amount of a CDKL5 fusion protein. The pharmaceutical formulations described herein can be administered to a subject in need thereof. The subject in need thereof can have a CDKL5 deficiency, Rett syndrome, and/or a symptom thereof. In other embodiments, the CDKL5 fusion protein can be used in the manufacture of a medicament for the treatment or prevention of a CDKL5 deficiency, Rett syndrome, and/or a symptom thereof.

Pharmaceutically Acceptable Carriers and Auxiliary Ingredients and Agents

The pharmaceutical formulations containing a therapeutically effective amount of a CDKL5 fusion protein described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the therapeutically effective amount of a of a CDKL5 fusion protein described herein, the pharmaceutical formulation can also include an effective amount of an auxiliary active agent, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbiturates, hydroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and 12-adrenergic agonists.

Suitable anti-infectives include, but are not limited to, amebicides (e.g. nitazoxanide, paromomycin, metronidazole, tinidazole, chloroquine, miltefosine, amphotericin b, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary antiinfectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, asparginase Erwinia chrysanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid Effective Amounts of the CDKL5 Fusion Protein and Auxiliary Agents The pharmaceutical formulations can contain a therapeutically effective amount of a CDKL5 fusion protein, and optionally, a therapeutically effective amount of an auxiliary agent. In some embodiments, the therapeutically effective amount of the CDKL5 fusion protein can range from about 1 pig/kg to about 10 mg/kg. In further embodiments, the therapeutically effective amount of the CDKL5 fusion protein can range from 1 ng/g bodyweight to about 0.1 mg/g bodyweight. The therapeutically effective amount of the CDKL5 fusion protein can range from about 1 pg to about 10 g. In some embodiments, the therapeutically effective mount of the CDKL5 fusion protein or pharmaceutical composition containing the CDKL5 fusion protein can range from about 10 nL to about 10 mL.

For some embodiments, the therapeutically effective amount can be from about 20 to about 50 ng per injection, such as for an intraventricular injection. In other embodiments, the therapeutically effective amount can be about 10 microliters per injection, such as for intraventricular injection. In further embodiments, the therapeutically effective amount can be about 5 ng/μL, such as for intraventricular injection. In yet further embodiments, the therapeutically effective amount can be about 1.9 μg/kg of bodyweight for intraventricular injection.

In other embodiments, the therapeutically effective amount can be from about 1 to about 2 micrograms per injection, such as for a systemically administered injection. In additional embodiments, the therapeutically effective amount can be about 200 to about 300 μL per injection, such as for a systemically administered injection. In some embodiments, the therapeutically effective amount can be about 5 ng/μL, such as for systemic injections. For some embodiments, the therapeutically effective amount can be about 1 to about 1.5 μg per 5 g of bodyweight. In some embodiments, the therapeutically effective amount can be from about 200 μg to about 300 μg per kg of bodyweight.

In embodiments where there is an auxiliary active agent contained in the pharmaceutical formulation in addition to the CDKL5 fusion protein, the therapeutically effective amount of the auxiliary active agent will vary depending on the auxiliary active agent. In some embodiments, the effective amount of the auxiliary active agent ranges from 0.001 micrograms to about 1 milligram. In other embodiments, the effective amount of the auxiliary active agent ranges from about 0.01 IU to about 1000 IU. In further embodiments, the effective amount of the auxiliary active agent ranges from 0.001 mL to about 1 mL. In yet other embodiments, the effective amount of the auxiliary active agent ranges from about 1% w/w to about 50% w/w of the total pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total pharmaceutical formulation.

Dosage Forms

In some embodiments, the pharmaceutical formulations described herein may be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravireal, intracerebral, and intracerebroventricular and intradermal. Such formulations may be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 1 ng to 1000 g of a pharmaceutical formulation containing a therapeutically effective amount or an appropriate fraction thereof of the CDKL5 fusion protein or composition containing the CDKL5 fusion protein The oral dosage form can be administered to a subject in need thereof.

Where appropriate, the dosage forms described herein can be microencapsulated. The dosage form can also be prepared to prolong or sustain the release of any ingredient. In some embodiments, the CDKL5 fusion protein is the ingredient whose release is delayed. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman. et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the CDKL5 fusion protein, auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the CDKL5 fusion protein, the composition containing a CDKL5 fusion protein, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

In some embodiments, the dosage forms are aerosol formulations suitable for administration by inhalation. In some of these embodiments, the aerosol formulation contains a solution or fine suspension of the CDKL5 fusion protein, the composition containing a CDKL5 fusion protein, and/or pharmaceutically acceptable salt thereof, and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a CDKL5 fusion protein, composition containing a CDKL5 fusion protein, or a pharmaceutical formulation thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time.

For some dosage forms suitable and/or adapted for inhaled administration, the pharmaceutical formulation is a dry powder inhalable formulation. In addition to the CDKL5 fusion protein, the composition containing a CDKL5 fusion protein, an auxiliary active ingredient, and/or pharmaceutically acceptable salt thereof, such a dosage form can contain a powder base such as lactose, glucose, trehalose, manitol, and/or starch. In some of these embodiments, the CDKL5 fusion protein, the composition containing a CDKL5 fusion protein, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the CDKL5 fusion proteins or compositions containing the CDKL5 fusion protein described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraperitoneal, subcutaneous, intramuscular, intradermal, intraosseous, epidural, intracardiac, intraarticular, intracavernous, intrathecal, intravireal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some embodiments, the dosage form contains a predetermined amount of the CDKL5 fusion protein or composition containing a CDKL5 fusion protein per unit dose. In an embodiment, the predetermined amount of the CDKL5 fusion protein or composition containing a CDKL5 fusion protein is a therapeutically effective amount of the CDKL5 fusion protein or composition containing a CDKL5 fusion protein to treat or prevent a CDKL5 deficiency, Rett syndrome, and/or a symptom thereof. In other embodiments, the predetermined amount of the CDKL5 fusion protein or composition containing a CDKL5 fusion protein can be an appropriate fraction of the therapeutically effective amount of the active ingredient. Such unit doses may therefore be administered once or more than once a day. Such pharmaceutical formulations may be prepared by any of the methods well known in the art.

Treatment of Neurological Disorders with TATk-CDKL5 Compositions and Formulations The CDKL5 fusion protein and pharmaceutical formulations thereof described herein can be used for the treatment and/or prevention of a disease, disorder, syndrome, or a symptom thereof in a subject. In some embodiments, the CDKL5 fusion protein and pharmaceutical formulations thereof can be used to treat and/or prevent a CDKL5 deficiency, Rett syndrome, variants of Rett syndrome, and/or a symptom thereof. In some embodiments, the subject has a CDKL5 deficiency, Rett syndrome, variants of Rett syndrome, and/or a symptom thereof.

An amount of the CDKL5 fusion protein, compositions, and pharmaceutical formulations thereof described herein can be administered to a subject in need thereof one or more times per day, week, month, or year. In some embodiments, the amount administered can be the therapeutically effective amount of the CDKL5 fusion protein, compositions, and pharmaceutical formulations thereof. For example, the CDKL5 fusion protein, compositions, and pharmaceutical formulations thereof can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further embodiments, the compounds, formulations, or salts thereof are administered one or more times per week, such as 1, 2, 3, 4, 5, or 6 times per week. In other embodiments, the CDKL5 fusion protein, compositions, and pharmaceutical formulations thereof can be administered one or more times per month, such as 1 to 5 times per month. In still further embodiments, the CDKL5 fusion protein, compositions, and pharmaceutical formulations thereof can be administered one or more times per year, such as 1 to 11 times per year.

The CDKL5 fusion proteins, compositions, and pharmaceutical formulations thereof can be co-administered with a secondary agent by any convenient route. The secondary agent is a separate compound and/or formulation from the CDKL5 fusion proteins, compositions, and pharmaceutical formulations thereof. The secondary agent can be administered simultaneously with the CDKL5 fusion proteins, compositions, and pharmaceutical formulations thereof. The secondary agent can be administered sequentially with the CDKL5 fusion proteins, compositions, and pharmaceutical formulations thereof. The secondary agent can have an additive or synergistic effect to the CDKL5 fusion proteins, compositions, and pharmaceutical formulations thereof. Suitable secondary agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics. In some embodiments the secondary agent is DCA.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbiturates, hydroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veraliptide, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbrompheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and 132-adrenergic agonists.

Suitable anti-infectives include, but are not limited to, amebicides (e.g. nitazoxanide, paromomycin, metronidazole, tinidazole, chloroquine, miltefosine, amphotericin b, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary antiinfectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspariginase *Erwinia chrysanthemi*, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

In embodiments where the CDKL5 fusion proteins, compositions, and pharmaceutical formulations thereof are simultaneously co-administered with a secondary agent, the CDKL5 fusion proteins, compositions, and pharmaceutical formulations thereof can be administered to the subject at substantially the same time as the secondary agent. As used in this context "substantially the same time" refers to administration of the CDKL5 fusion proteins, compositions, and pharmaceutical formulations thereof and a secondary agent where the period of time between administration of the CDKL5 fusion protein, composition, or pharmaceutical formulation thereof and the secondary agent is between 0 and 10 minutes.

In embodiments where the CDKL5 fusion protein, composition, or pharmaceutical formulations thereof is sequentially co-administered with a secondary agent, the CDKL5 fusion protein, composition, or pharmaceutical formulations thereof can be administered first, and followed by administration of the secondary agent after a period of time. In other embodiments where the CDKL5 fusion protein, composition, or pharmaceutical formulations thereof is sequentially co-administered with a secondary agent, the secondary agent can be administered first, and followed by administration of the CDKL5 fusion protein, composition, or pharmaceutical formulations thereof after a period of time. In any embodiment, the period of time between administration of the CDKL5 fusion protein, composition, or pharmaceutical formulations thereof and the secondary agent can range from 10 minutes to about 96 hours. In some embodiments the period of time can be about 10 minutes, about 30 minutes, about 1 hour, about 2 hours, about 4 hours, about 6 hours, about 8 hours, about 10 hours, or about 12 hours. The sequential administration can be repeated as necessary over the course of the period of treatment.

The amount of the CDKL5 fusion proteins, compositions, pharmaceutical formulations thereof that can be administered are described elsewhere herein. The amount of the secondary agent will vary depending on the secondary agent. The amount of the secondary agent can be a therapeutically effective amount. In some embodiments, the effective amount of the secondary agent ranges from 0.001 micrograms to about 1 milligram. In other embodiments, the amount of the secondary agent ranges from about 0.01 IU to about 1000 IU. In further embodiments, the amount of the secondary agent ranges from 0.001 mL to about 1 mL. In yet other embodiments, the amount of the secondary agent ranges from about 1% w/w to about 50% w/w of the total pharmaceutical formulation. In additional embodiments, the amount of the secondary agent ranges from about 1% v/v to about 50% v/v of the total pharmaceutical formulation. In still other embodiments, the amount of the secondary agent ranges from about 1% w/v to about 500% w/v of the total secondary agent composition or pharmaceutical formulation.

In some embodiments, the composition or formulation containing the CDKL5 fusion protein is administered to a patient via and injection. Suitable methods of injection include, but are not limited to, intravenous, intraperitoneal, subcutaneous, intramuscular, intradermal, intraosseous, epidural, intracardiac, intraarticular, intracavernous, intrathecal, intravireal, intracerebral, and intracerebroventricular injection Other suitable methods of administration of the composition or formulation containing the CDKL5 fusion protein include, but are not limited to, topical, transdermal, nasal, or oral delivery. In some embodiments, the dosage of the CDKL5 fusion protein ranges from about 0.01 µg/g bodyweight to about 10 mg/g bodyweight.

Figure 3:
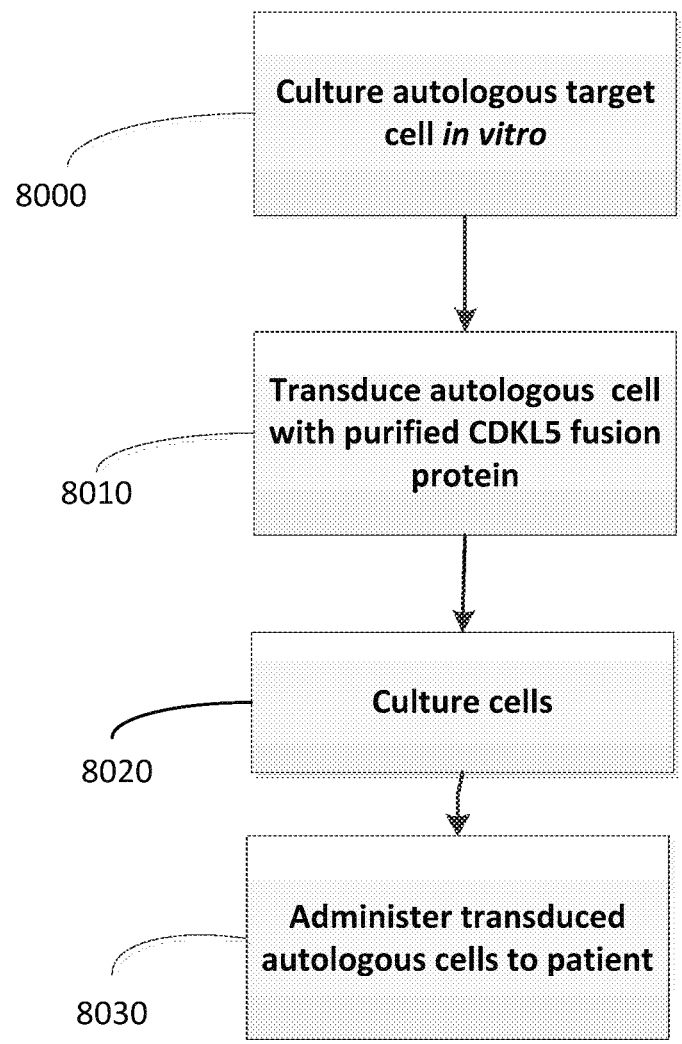
FIG. 3 shows one embodiment of method of delivering a CDKL5 fusion protein via an autologous cell.

In other embodiments, the CDKL5 fusion protein can be delivered to a patient in need of treatment via cell therapy. With this in mind attention is directed to FIG. 3, which shows one embodiment of method of delivering a CDKL5 fusion protein via an autologous cell. The method begins by culturing cells in vitro (8000). Preferably, the cells are autologous cells. In one embodiment, the autologous cells are neurons or neuronal precursor cells, such as neural stem cells. In some embodiments, the autologous cells are neurons are derived from induced pluripotent stem cells. In other embodiments, the autologous cells are neurons are derived from umbilical cord blood stem cells.

Next, the cultured cells are transduced with a purified CDKL5 fusion protein (8010). In other embodiments, the cultured cells are transduced by exposing the culture cells to media containing a CDKL5 fusion protein as previously described. In further embodiments, the cultured cells are transfected with a suitable vector containing a CDKL5 fusion protein cDNA. The cells are then cultured for a suitable amount of time to allow for expression of the CDKL5 fusion protein (8020). In some embodiments, the cells are cultured for about 6 h to about 96 h. After the cells are cultured, one or more transduced cells are administered to a patient.

In one embodiment, transduced autologous neurons are delivered to the brain using surgical techniques. In some embodiments, one or more transduced cells are administered to a patient via injection. In some embodiments, one or more transduced cells are included in a formulation. In one embodiment, the formulation containing one or more transduced cells also includes a pharmaceutically acceptable carrier and/or an active agent. In some embodiments the formulation containing the one or more transduced cells is administered to a patient via injection or using a surgical technique.

Kits Containing the CDKL5 Fusion Protein and Formulations Thereof

The CDKL5 fusion protein, compositions containing the CDKL5 fusion protein, and pharmaceutical formulations thereof described herein can be presented as a combination kit. As used herein, the terms "combination kit" or "kit of parts" refers to the CDKL5 fusion protein, compositions containing the CDKL5 fusion protein, and pharmaceutical formulations thereof described herein and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

The combination kit can contain each agent, compound, pharmaceutical formulation or component thereof, in separate compositions or pharmaceutical formulations. The separate compositions or pharmaceutical formulations can be contained in a single package or in separate packages within the kit. Also provided in some embodiments, are buffers, diluents, solubilization reagents, cell culture media and other reagents. These additional components can be contained in a single package or in separate packages within the kit.

In some embodiments, the combination kit also includes instructions printed on or otherwise contained in a tangible medium of expression. The instructions can provide information regarding the content of the CDKL5 fusion protein, compositions containing the CDKL5 fusion protein, and pharmaceutical formulations thereof and/or other auxiliary and/or secondary agent contained therein, safety information regarding the content of the CDKL5 fusion protein, compositions containing the CDKL5 fusion protein, and pharmaceutical formulations thereof and/or other auxiliary and/or secondary agent contained therein, information regarding the dosages, indications for use, and/or recommended treatment regimen(s) for the CDKL5 fusion protein, compositions containing the CDKL5 fusion protein, and pharmaceutical formulations thereof and/or other auxiliary and/or secondary agent contained therein. In some embodiments, the instructions can provide directions for administering the CDKL5 fusion protein, compositions containing the CDKL5 fusion protein, and pharmaceutical formulations thereof and/or other auxiliary and/or secondary agent to a subject having a CDKL5 deficiency, Rett syndrome, and/or a symptom thereof.

Without further elaboration, it is believed that one skilled in the art can, based on the description herein, utilize the present disclosure to its fullest extent. It is emphasized that the embodiments of the present disclosure, particularly any "preferred" embodiments, are merely possible examples of the implementations, merely set forth for a clear understanding of the principles of the disclosure. Many variations and modifications may be made to the disclosed embodiment(s) of the disclosure without departing substantially from the spirit and principles of the disclosure. All such modifications and variations are within the scope of this disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

EXAMPLES

The following examples are put forth so as to provide those of ordinary skill in the art with a complete disclosure and description of how to perform the methods and use the compositions and compounds disclosed and claimed herein. The specific examples below are to be construed as merely illustrative, and not limitative of the remainder of the disclosure in any way whatsoever. Efforts have been made to ensure accuracy with respect to numbers (e.g. amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1: Production and Purification of the TATk-CDKL5 Protein

To produce a deliverable TAT-CDKL5 fusion protein a synthetic TATκ-PTD in which mutation of the furin recognition sequences in the TAT domain allows secretion of recombinant proteins was used. The secreted protein was observed to be successfully taken up by the target cells. TATk-CDKL5 fusion gene containing a human CDKL5 was cloned into the expression plasmid pSecTag2 (Life Technologies). This plasmid is designed to allow expression of genes in mammalian hosts and high expression levels of target proteins. Proteins expressed from pSecTag2 are fused at the N-terminus to the murine Igκ chain leader sequence for protein secretion in culture medium. The TATk-CDKL5 fusion protein was tagged with a GFP protein to allow for western blot analysis using an anti-GFP antibody. To facilitate protein purification, the TATk-CDKL5 fusion protein was configured to include a myc-tag and 6×His tag at the C-terminal region of the TATk-GFP-CDKL5 gene. HEK 293T cells were transfected with the TATk-GFP-CDKL5 expression plasmid using standard plasmid delivery methods. After transfection cells were left to grow in serum-free medium (High glucose Dulbecco's Modified Eagle Medium). After 48 hours medium was collected, diafiltered and concentrated with Amicon ultra centrifugal filters (50 kDa cut-off). This method allows buffer exchange and enrichment of the secreted protein.

Figure 4A:
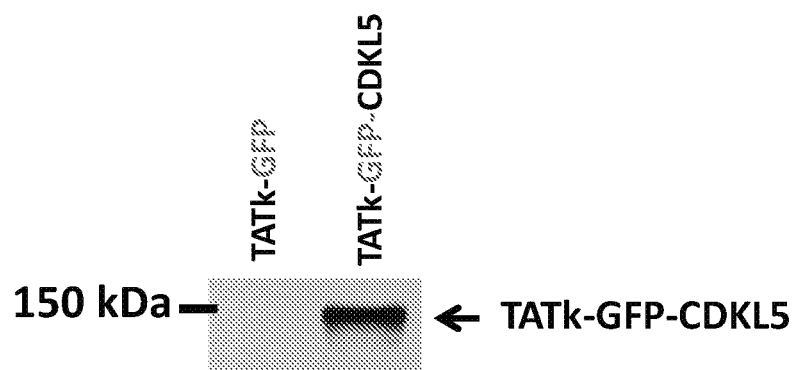
FIGS. 4A and 4B demonstrate western blot analysis results from TATk-CDKL5 protein expression in transfected HEK293T cells. TATk-CDKL5 fusion protein was tagged with a GFP protein to allow for western blot analysis using an anti-GFP antibody.
Figure 4B:
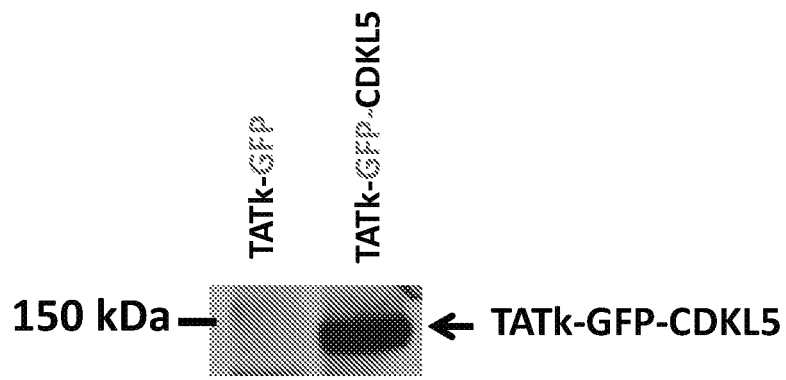

FIGS. 4A and 4B demonstrate western blot analysis results from TATk-GFP-CDKL5 protein expression in transfected HEK293T cells. FIG. 4A demonstrates TATk-GFP-CDKL5 fusion protein expression in cell homogenates from transfected HEK293T cells. FIG. 4B demonstrates TATk-GFP-CDKL5 fusion protein accumulation in concentrated (20×) cell culture medium from transfected HEK293T cells.

Example 2: Validation of TATk-CDKL5 Kinase Activity

Figures 5A, 5B:
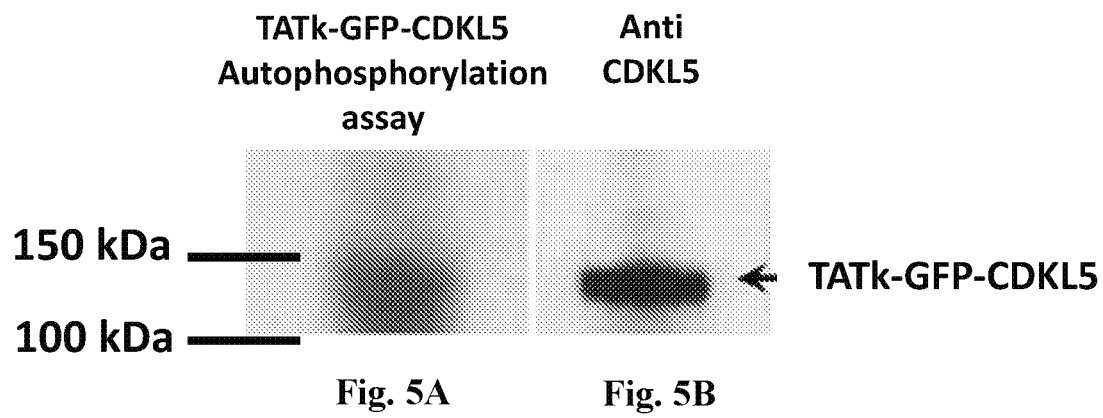
FIGS. 5A and 5B demonstrate results from a kinase activity assay (FIG. 5A) demonstrating that TAT-GFP-CDKL5 fusion protein retains CDKL5 autophosphorylation activity.

In order to purify the TATk-GFP-CDKL5 protein, a myc-tag and a 6×His tag were added at the C-terminal region of the TATk-GFP-CDKL5 gene. TATk-GFP-CDKL5 fusion protein was purified from culture medium on a Ni-NTA resin. It has been shown that the CDKL5 kinase has a high autophosphorylation activity. As shown in FIGS. 5A and 5B, which shows the results from an in vitro kinase activity assay, purified TATk-GFP-CDKL5 protein preserves its autophosphorylation activity. This demonstrates that the purified fusion protein retains its kinase activity.

Example 3: Internalization of TATk-CDKL5 by HEK293T Cells

Figure 6:
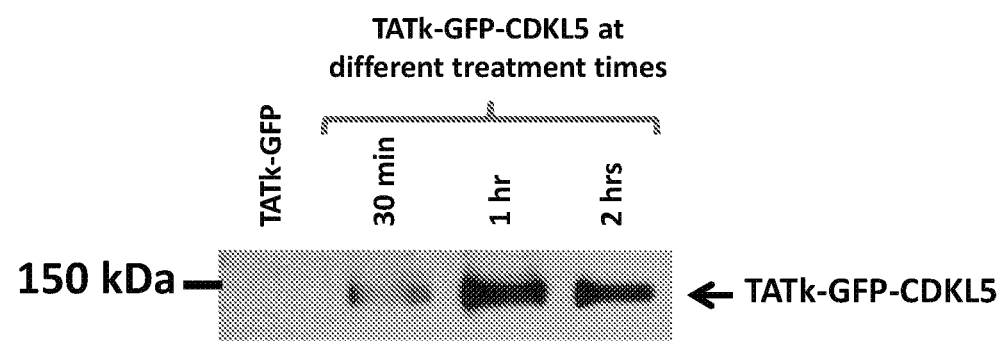
FIG. 6 shows the effect of incubation time on transduction efficiency of one embodiment of a TATk-GFP-CDKL5 fusion protein in HEK 293T cells.
Figure 7A:
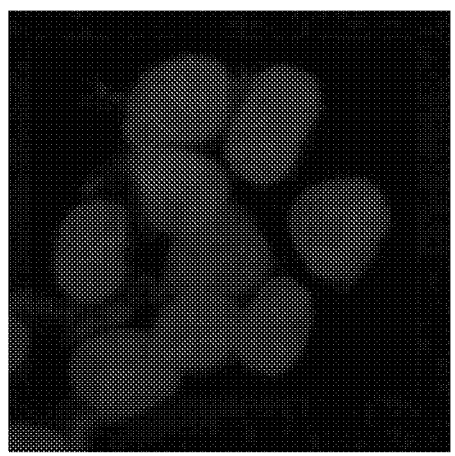
FIGS. 7A and 7B shows localization of CDKL5 in TATk-GFP-CDKL5 treated HEK 293T cells (FIG. 7B).
Figure 7B:
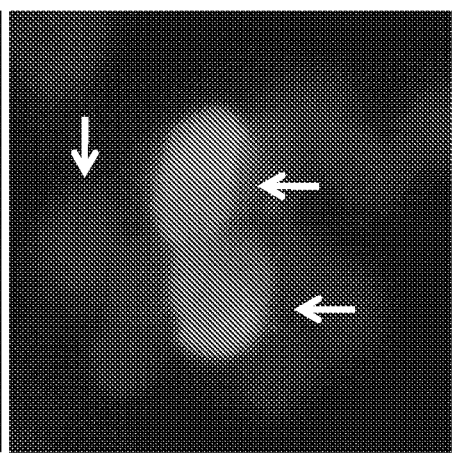
Figure 8:
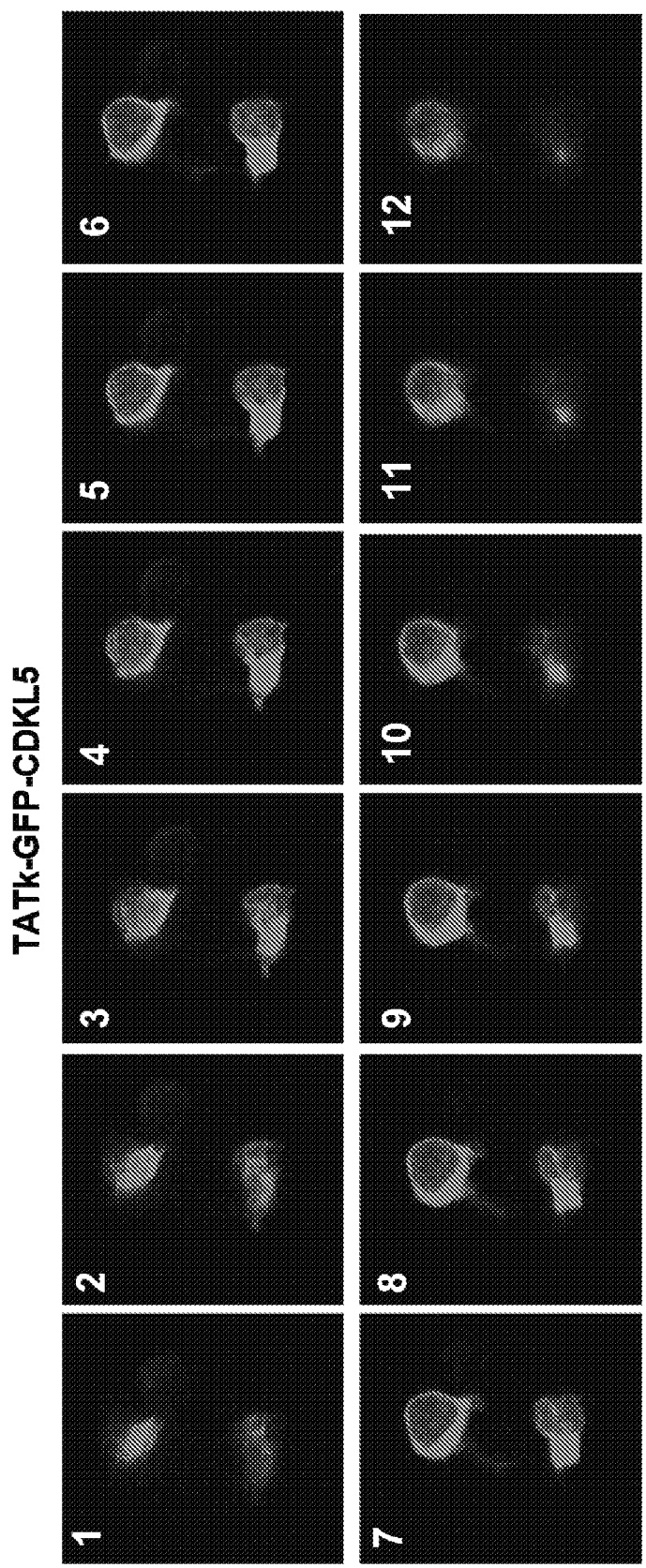
FIG. 8 is an image demonstrating a serial of 12 images (1-12) from confocal microscopy demonstrating TATk-GFP-CDKL5 transduction into SH-SY5Y cells treated with purified TATk-GFP-CDKL5 protein for 30 minutes. Z stack size was 0.4 µm.

To evaluate the efficiency of the transduction of the TATk-GFP-CDKL5 fusion protein HEK 293T cells were incubated with the purified/concentrated fusion protein. Briefly, the TATk-GFP-CDKL5 fusion protein was produced and purified as described in Example 1. HEK 293 cells were incubated in concentrated media containing the fusion protein. After different incubation times cells were lysed and total protein extracts were transferred to a nitrocellulose membrane for immunoblotting for TATk-GFP-CDKL5 protein quantification. As shown in FIG. 6, TATk-GFP-CDKL5 is internalized by cells after only about 30 minutes of incubation. Other cultures were treated in parallel and were fixed and immunostained with an anti-GFP specific antibody to visualize the transduced TATk-GFP-CDKL5 protein. As demonstrated in FIGS. 7A-7B, TATk-GFP-CDKL5 protein was efficiently translocated into the cells. The internalization in target cells was confirmed by confocal microscopy (FIG. 8). SH-SY5Y neuroblastoma cells were incubated in concentrated media containing the fusion protein for 30 minutes. FIG. 8 shows an image of a serial of confocal images (1-12) of TATk-GFP-CDKL5 transduced SH-SY5Y cells, demonstrating that TATk-GFP-CDKL5 protein is internalized by target cells and localized both in the nucleus and cytoplasm of SH-SY5Y cells (FIG. 8).

Example 4: TATk-CDKL5 Induces Differentiation and Inhibits Proliferation of the SHSY5Y Neuroblastoma Cell Line In spite of the clear importance of CDKL5 for the central nervous system, the biological functions of this kinase remain largely unknown. CDKL5 gene affects both proliferation and differentiation of neural cells (See e.g. Valli et al., 2012. Biochim Biophys Acta. 1819:1173-1185, and Rizzi et al., 2011. Brain Res. 1415:23-33). Neuroblastoma cells share several features with normal neurons and thus are considered a good in vitro model to study the biochemical and functional properties of neuronal cells, particularly when they are induced to differentiate upon treatment with agents such as retinoic acid (RA) (See e.g., Singh, 2007 Brain Res. 1154 p 8-21; Melino, 1997 J. Neurooncol. 31 pp 65-83). For these reasons, neurobastoma cells were employed to study the CDKL5 function in vitro.

SH-SY5Y cells were treated with purified TATk-GFP-CDKL5 similar to the treatment of described in Example 3. Here, SH-SY5Y cells were incubated with the concentrated media containing the purified TATk-GFP-CDKL5 protein for about 24 hours. Cell proliferation was evaluated as mitotic index (the ratio between the number of cells in a population undergoing mitosis to the number of cells not undergoing mitosis) using Hoecsht nuclear staining. Differentiation was evaluated by examining neurite growth, which is a sign of neuronal differentiation. For analysis of neurite growth, cells were grown for an additional 1-2 days in the presence or absence of the pro-differentiation agent, RA. Neurite outgrowth was measured using an image analysis system.

Figures 9A, 9B:
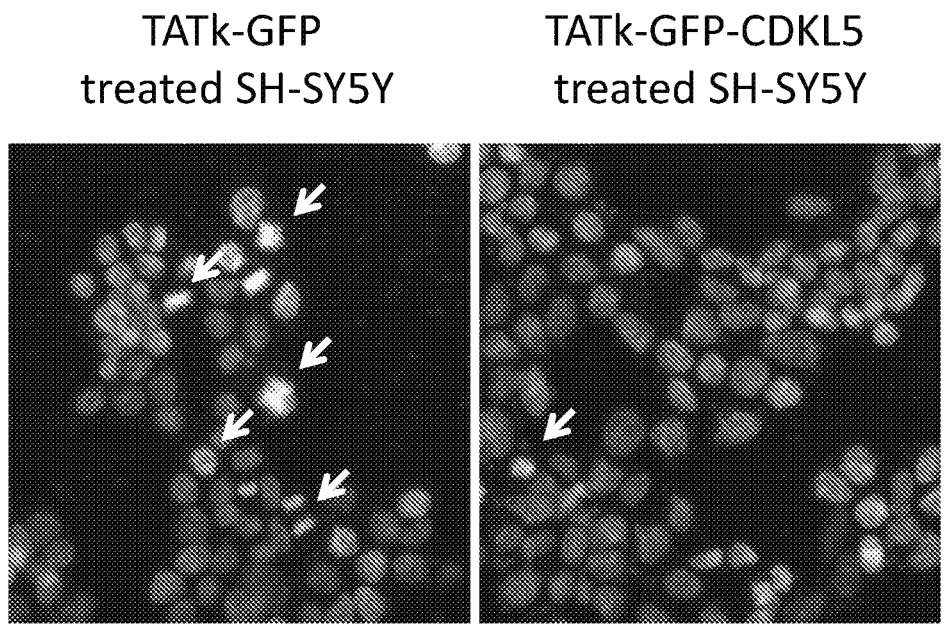
FIGS. 9A and 9B demonstrate the effect of transduced CDKL5 in neuroblastoma cells (SH-SY5Y) on cell proliferation. TATk-GFP-CDKL5 treated cells (FIG. 9B) were observed to have decreased proliferation as compared to TATk-GFP (control) treated cells (FIG. 9A). The white arrows indicate mitotic nuclei.
Figure 10:
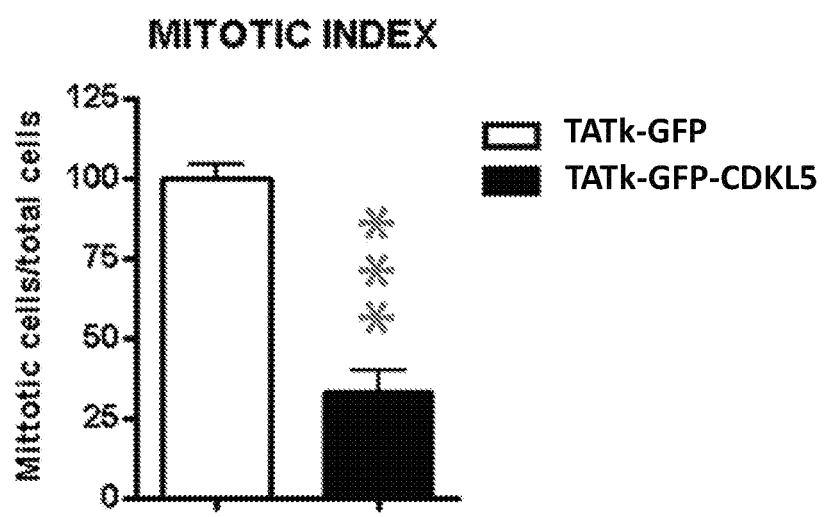
FIG. 10 shows a graph demonstrating the mitotic index of SH-SY5Y cells treated with TATk-GFP or TATk-GFP-CDKL5 fusion proteins. The y-axis show mitotic cells/total cells and is expressed in percent. Data is shown as mean±S.E. *** $P<0.001$ (t-test).

Induction of CDKL5 expression (by TATk-GFP-CDKL5 protein) caused a strong inhibition of cell proliferation (e.g., FIGS. 9A-9B, and 10) with no increase in apoptotic cell death (data not shown) compared to controls. Further, as shown in FIGS. 11A-11B and 12, TATk-GFP-CDKL5 promotes neuroblastoma cell differentiation as indicated by neurite outgrowth in SH-SY5Y cells. These results demonstrate that TATk-CDKL5 is functional in an in vitro neuronal model.

Example 5: Characterization of the CDKL5-KO Mouse Model

Figure 13A:
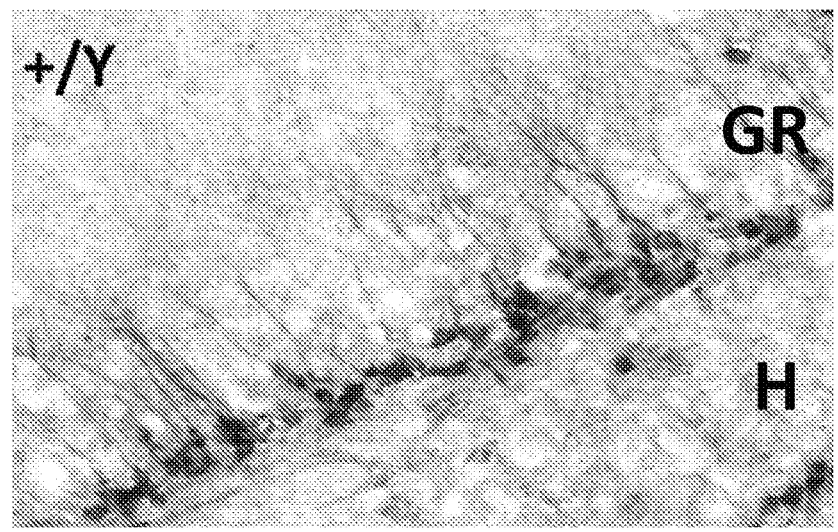
FIGS. 13A-13B show images demonstrating the dendritic morphology and the number of newborn hippocampal granule cells as shown by immunohistochemistry for doubleocortin (DCX) in wild type (FIG. 13A) and CDKL5 knockout (KO) mice (FIG. 13B). Scale bar=50 µm. Abbreviations: GR, granular layer: H, Hilus.
Figure 13B:
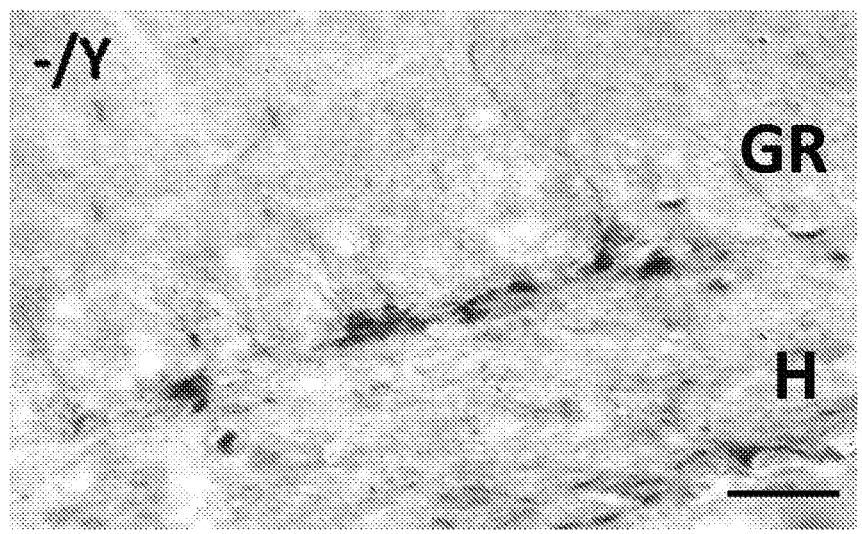
Figures 14A, 14B:
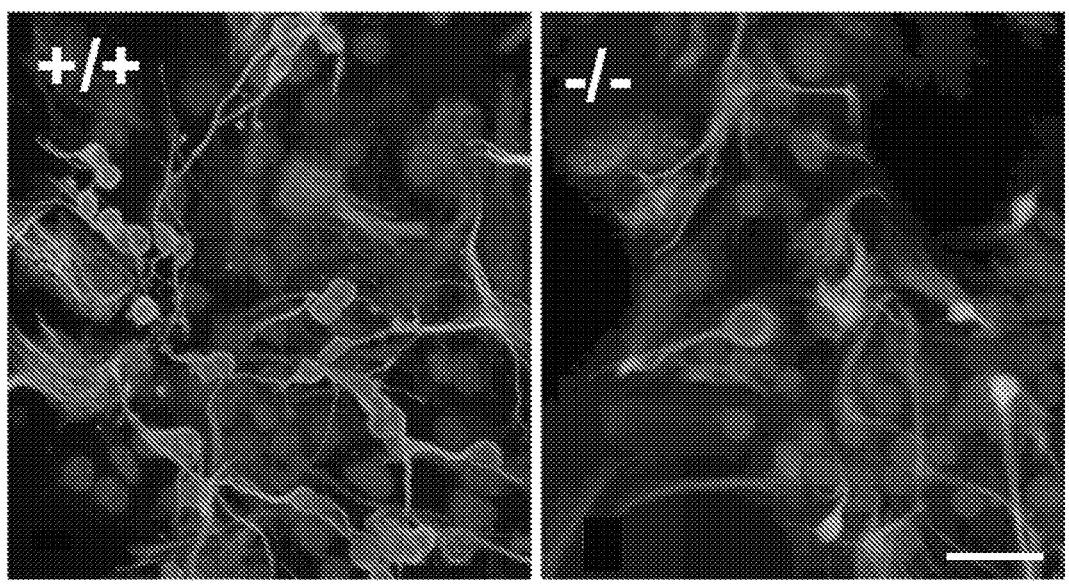
FIGS. 14A-14B show double-fluorescence images of differentiated neuronal precursor cells (NPCs) demonstrating a reduction in the generation and maturation of new neurons (red cells) in neuronal cultures derived from CDKL5 knockout mice (−/−) (FIG. 14A) as compared to wild-type (+/+) (FIG. 14B) neuronal cultures. Cells with a neuronal phenotype are immunopositive for β-tubulin III (red) and cells with an astrocytic phenotype are immunopositive for GFAP (green). Cell nuclei were stained using Hoechst dye (blue). Scale bar=25 µm.
Figures 15A, 15B, 15C:
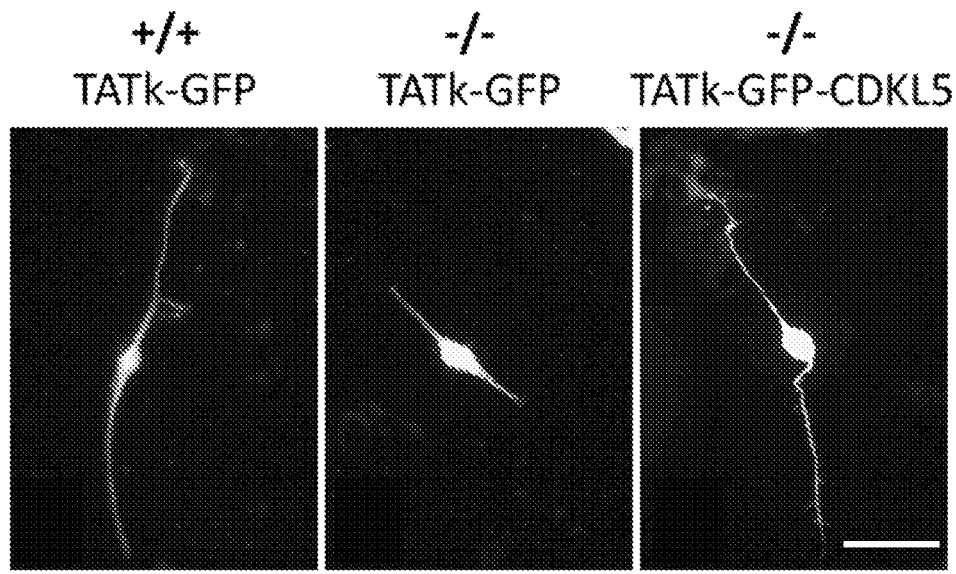
FIG. 15A-15C shows representative images of neuronal precursor cultures from CDKL5 knockout mice (FIGS. 15B and 15C), transduced with TATk-GFP (FIG. 15B) or TATk-GFP-CDKL5 (FIG. 15C), as well as neuronal precursor cultures from wild-type mice (FIG. 15A). Scale bar=20 µm.
Figure 16:
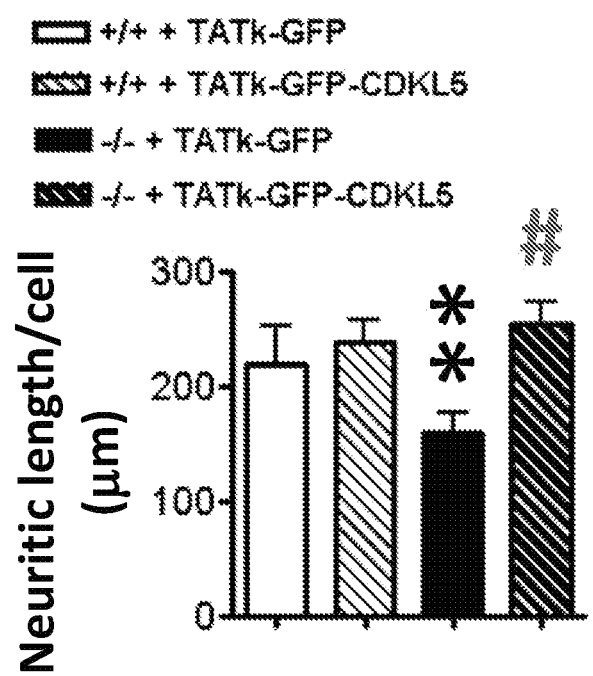
FIG. 16 shows a graph demonstrating quantification of neural maturation as measured by the total neuritic length of differentiated neurons (neurons positive for beta-tubulin III) in neuron precursor cultures from wild type and CDKL5 KO mice treated with either TATk-GFP or TATk-GFP-CDKL5. Values represent mean±SE **$p<0.01$ as compared to wild type condition; # $p<0.01$ as compared to untreated KO samples (Bonferroni test after ANOVA).
Figure 18A:
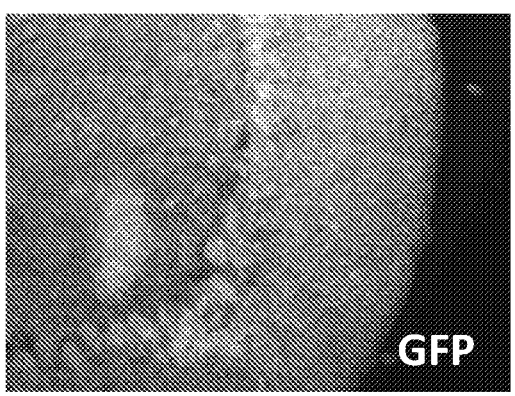
FIGS. 18A-18D show images of cerebellar sections demonstrating immunodetection of CDKL5 in the brains of mice (postnatal day 7) systemically treated as in FIGS. 17A-17F with the culture medium (vehicle) (FIGS. 18A and 18B) and TATk-GFP-CDKL5 (FIGS. 18C and 18D). Localization of TATk-GFP-CDKL5 in the brain was evaluated by immunohistochemistry using an anti-GFP antibody (FIG. 18A-18B). Slides were mounted with DAPI to stain cell nuclei (FIG.
Figure 18B:
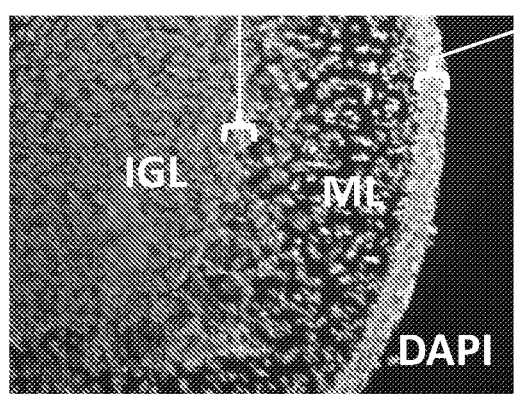
Figure 18C:
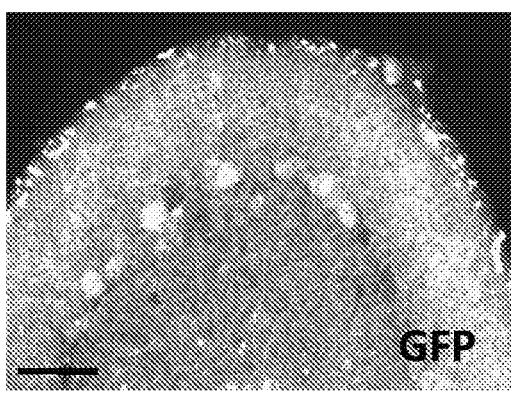
Figure 18D:
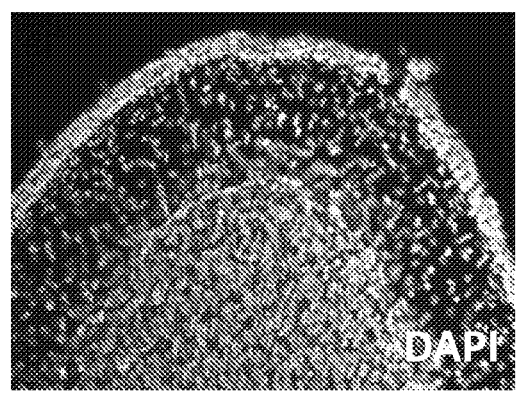

A CDKL5 knockout mouse model has been recently created by the EMBL in Monterotondo, Italy, by the group lead by Dr. Cornelius Gross (Amendola, 2014 PLoS One. 9(5):e91613). To establish the effect of CDKL5-loss of function on dendritic development of newborn neurons, the dendritic morphology of newborn hippocampal granule cells derived from the CDKL5 KO mouse was examined. Dendritic morphology of newborn neurons was analyzed with immunohistochemistry for doublecortin (DCX), taking advantage of the expression of this protein in the cytoplasm of immature neurons during the period of neurite elongation. As shown in FIGS. 13A-13B, DCX-positive cells of CDKL5 knockout mice (−/Y) exhibited a dendritic tree with a highly immature pattern (FIG. 13B) compared to the wild type (+/Y) counterparts (FIG. 13A). A highly immature pattern can be evidenced by little branching and elongation. Absence of CDKL5 resulted in a decrease in the number of DCX-positive cells (FIG. 13B) due to an increase in apoptotic cell death (data not shown) that was observed to affect postmitotic immature granule neurons (DCX-positive cells) (Fuchs, 2014 Neurobiol Dis. 70 p 53-68). This data suggests that CDKL5 plays a fundamental role on postnatal neurogenesis, by affecting neural precursor survival and maturation of newborn neurons. Cultures of neuronal precursor cells (NPCs) from the subventricolar zone (SVZ) of Cdkl5 knockout mice were observed to exhibit the same defects observed in vivo in cerebellar granule cell precursors. Namely, in cultures of neuronal precursor cells derived from wild type mice (+/+) there were more neurons (β-tubulin III positive cells, red cells) than in cultures of neuronal precursor cells derived from CDKL5 KO (−/−) mice (FIGS. 14A and 14B). This suggests that the loss of CDKL5 decreases the survival of postmitotic neurons. Assessment of neurite outgrowth in θ-tubulin III positive cells demonstrated that neurons generated from Cdkl5 knockout NPCs were less differentiated compared to wild type neurons (FIGS. 14A and 14B). These results suggest that postmitotic NPCs from CDKL5 knockout mice have an intrinsic defect, not only in cell survival, but also in neuronal maturation.

Example 6: TATk-CDKL55 Protein Restores Neurite Development of Neronal Cell Precursors Derived from a CDKL5 KO Mouse Neuronal precursor cells cultures from the CDKL5 KO (−/−) mouse and wild-type (+/+) mouse were treated with TATk-GFP-CDKL5 or TATk-GFP. Neuronal maturation was evaluated by measuring the total neuritic length of differentiated neurons (positive for β-tubulin III). Evaluation of neurite length was performed by using the image analysis system Image Pro Plus (Media Cybernetics, Silver Spring, Md. 20910, USA). The average neurite length per cell was calculated by dividing the total neurite length by the number of cells counted in the areas. As shown in FIGS. 15A-15C and 16, absence of CDKL5 causes a reduction in the maturation of new neurons and treatment with TATk-CDKL5 restores neurite development.

Example 7: Delivery of TATk-CDKL5 into the Mouse Brain

Seven-day old mouse pups were subcutaneous injected with a single dose of culture medium of HEK293T cells transfected with TATk-GFP-CDKL5, TATk-GFP or medium from untransfected cells (vehicle) (single dose corresponded to about 200 µl of 200× concentrated medium; which contained about 1-1.5 µg of the fusion protein). Culture medium was collected after 48 hours from transfection and was diafiltered and concentrated with Amicon ultra centrifugal filters (50 kDa cut-off). Mice were sacrificed 4 hours post-administration of the treatment. Brains were stored in the fixative for 24 hours, cut along the midline and kept in 20% sucrose in phosphate buffer for an additional 24 hours. Hemispheres were frozen and stored at −80° C. The right hemisphere was cut with a freezing microtome in 30-µm-thick coronal sections. Immunohistochemistry was carried out on free-floating sections. Localization of TATk-GFP-CDKL5 and TATk-GFP in the brain was evaluated by immunohistochemistry using an anti-GFP antibody and a TSA amplification kit. Images were taken at the level of the sensory-motor cortex and the cerebellum. Cells were counterstained using 4',6-diamidino-2-phenylindole (DAPI). Representative images demonstrating presence of the TATk-GFP-CDKL5 protein in the sensory-motor cortex and cerebellum of mice are shown in FIGS. 17A-17F and FIGS. 18A-18D, respectively. Given that the TATk-GFP-CDKL5 protein was subcutaneous administered, this data demonstrates that the TATk-GFP-CDKL5 protein is effectively transported across the blood brain barrier and enters into brain cells.

Example 8: Effect of TATk-CDKL5 Fusion Protein In Vivo on Neuronal Maturation, Survival and Connectivity Adult mice (4-6 months of age) were intraventricularly injected (FIG. 19) for 5 consecutive days (see e.g. FIG. 20 for experimental schedule) with TATk-GFP-CDKL5 or TATk-GFP. Briefly, mice were anesthetized with ketamine (100-125 mg/kg) and xylazine (10-12.5 mg/kg). Cannulas (0.31-mm diameter, Brain Infusion Kit III; Alzet Cupertino, Calif.) were stereotaxically implanted into the lateral ventricles (A/P—0.4-mm caudal, M/L 1.0 mm, D/V—2.0 mm; FIG. 19). Seven days after implantation mice were infused for 5 consecutive days with 10 µl (about 50 ng) of TATk-GFP-CDKL5 or TATk-GFP in PBS by using a Hamilton syringe connected to a motorized nanoinjector (at a rate of 0.5 µl/min). Four hours after the last injection animals were sacrificed, and the dendritic morphology of newborn hippocampal granule cells was analyzed with immunohistochemistry for DCX. FIGS. 21 and 22 demonstrate that DCX positive neurons of Cdkl5 KO mice had shorter processes than those of their wild type counterparts (FIGS. 21A-21B and 22A-22B). TATk-GFP-CDKL5 fusion protein administered intraventricularly on five consecutive days was observed to increase neurite length and branch number in CDKL5 knockout mice (FIG. 22C) to levels similar to wild-type (FIG. 22A). FIGS. 23A-23B show examples of the reconstructed dendritic tree of newborn granule cells of wild-type (+/Y) (FIG. 23A), hemizygous CDKL5 knockout mice (−/Y) (FIG. 23B), and hemizygous CDKL5 knockout male mice treated with a TATk-GFP-CDKL5 fusion protein.

Quantification of the dendritic size of DCX positive cells demonstrate that CDKL5 knockout mice (−/Y) mice had a shorter dendritic length (FIG. 24A) and a reduced number of segments (FIG. 24B) than wild type mice (FIGS. 24A and 24B). In TATk-GFP-CDKL5 treated CDKL5 knockout mice (−/Y) mice there was an increase in both parameters that became even larger in comparison with +/Y mice (FIGS. 24A-24B). The effects of TATk-GFP-CDKL5 treatment on details of the dendritic architecture were examined by evaluating each dendritic order separately. A striking feature of CDKL5 KO mice was the absence of branches of higher order (FIGS. 25A-25B; red arrows). While wild type (+/Y) mice had up to 10 orders of branches, CDKL5 knockout mice (−/Y) mice lacked branches of orders 8-10 (FIG. 25A, arrows). In addition, CDKL5 knockout mice (−/Y) mice showed a reduced branch length of orders 5-8 (FIG. 25A) and a reduced number of branches of orders 6-8 (FIG. 25B). Taken together, these data indicate that in Cdkl5 KO mice the dendritic tree of the newborn granule cells is hypotrophic and that this defect is due to a reduction in the number and length of branches of intermediate order and a lack of branches of higher order. All these defects were observed to be completely rescued by TATk-GFP-CDKL5 treatment (FIGS. 25A to 25B).

In order to evaluate the effect of TATk-GFP-CDKL5 treatment on apoptotic cell death, we counted the number of apoptotic cells expressing cleaved caspase-3 in the hippocampal dentate gyrus (FIG. 26). Quantification of cleaved caspase-3 cells shows that TATk-GFP-CDKL5 treatment completely normalized apoptotic cell death in CDKL5 knockout mice (−/Y) (FIG. 26). It was observed that CDKL5 knockout mice (−/Y) mice had fewer postmitotic neurons (DCX-positive cells) than wild type (+/Y) mice in the hippocampal dentate gyrus (FIG. 27). TATk-GFP-CDKL5-treated CDKL5 knockout mice underwent an increase in the number of postmitotic neurons that became similar to those of wild type (+/Y) mice (FIG. 27). This indicates that the increased death of posmitotic immature granule cells that characterizes CDKL5 knockout mice is rescued by TATk-GFP-CDKL5 treatment. Taken together, these data demonstrate that treatment with TATk-GFP-CDKL5 in CDKL5 knockout mice increased neurite length and survival of newborn cells in the hippocampus indicating that injected TATk-CDKL5 diffused from the lateral ventricle to the hippocampus and restored maturation and survival of post-mitotic granule cells.

Without being bound by any one theory, a reduction in connectivity may be the counterpart of the dendritic hypotrophy that characterizes the newborn granule cells of CDKL5 KO mice. Synaptophysin (SYN; also known as p38) is a synaptic vesicle glycoprotein that is a specific marker of presynaptic terminals. Here, it was observed in CDKL5 knockout mice (−/Y) mice that the optical density of SYN was significantly lower than in wild type (+/Y) mice in the molecular layer of the hippocampus (FIGS. 28 and 30A), suggesting that CDKL5 KO mice had fewer synaptic contacts in the dentate gyrus. FIGS. 28A-28C show representative images demonstrating brain sections processed for synaptophysin (SYN) immunofluorescence from the molecular layer (Mol) of the dentate gryrus (DG) from a wild-type male mouse (+/Y) (FIG. 28A), a hemizygous CDKL5 knockout male mouse (−/Y) (FIG. 28B), and a hemizygous CDKL5 knockout male mouse treated with TATk-GFP-CDKL5 fusion protein via intraventricular injections given once a day for 5 consecutive days (−/Y+TATk-GFP-CDKL5) (FIG. 28C). One out of six 30-μm-thick coronal sections from the DG of animals were processed for immunohistochemistry. Immunohistochemistry was carried out on free-floating sections for the frozen brains. For Synaptophysin immunohistochemistry, sections were incubated for 48 hours at 4° C. with mouse monoclonal anti-SYN (SY38) antibody (1:1000, MAB 5258, Millipore Bioscience Research Reagents) and for 2 hours with a Cy3 conjugated anti-mouse IgG secondary antibody (1:200; Jackson Immunoresearch. Intensity of immunoreactivity (IR) was determined by optical densitometry of immunohistochemically stained sections. Fluorescence images were captured using a Nikon Eclipse E600 microscope equipped with a Nikon Digital Camera DXM1200 (ATI system). Densitometric analysis in the molecular layer and cortex was carried out using Nis-Elements Software 3.21.03 (Nikon). For each image, the intensity threshold was estimated by analyzing the distribution of pixel intensities in the image areas that did not contain IR. This value was then subtracted to calculate IR of each sampled area. Values are given as a percentage of the optical density of control CDKL5+/Y mice (mean+standard error).

Dendritic arborization is significantly reduced in cortical pyramidal neurons of CDKL5 knockout mice compared to their wild type counterparts (Amendola, 2014 PLoS One. 9(5):e91613). A similar lower level of SYN immunoreactivity in the layers III of the neocortex was observed (FIG. 30B). In CDKL5 knockout mice (−/Y) mice treated with TATk-GFP-CDKL5 these defects were fully rescued (FIG. 28 and FIGS. 30A and 30B), suggesting that the positive impact of treatment with TATk-GFP-CDKL5 on dendritic structure was paralleled by restoration of the input to neurons.

Example 9: Effect of TATk-CDKL5 Fusion Protein In Vivo on P-AKT

AKT is a central signaling kinase associated with multiple cellular pathways. Phosphorylated AKT (P-AKT) is significantly reduced in CDKL5 knockout animals, CDKL5 deficiency and Rett syndrome. FIGS. 29A-29C show representative images demonstrating brain sections processed for P-AKT immunofluorescence from the molecular layer (Mol) of the dentate gryrus (DG) from a wild-type male mouse (+/Y) (FIG. 29A), a CDKL5 knockout male mouse (−/Y) (FIG. 29B), and a CDKL5 knockout male mouse treated with TATk-GFP-CDKL5 fusion protein via intraventricular injections given once a day for 5 consecutive days (−/Y+TATk-GFP-CDKL5) (FIG. 29C). For phospho-AKT immunohistochemistry, sections were incubated for 24 hours at 4° C. with mouse monoclonal anti-phospho-AKT-Ser473 antibody (1:1000, Cell Signaling Technology) and for 2 hours with a Cy3 conjugated anti-mouse IgG secondary antibody (1:200; Jackson Immunoresearch). Intensity of immunoreactivity (IR) was determined by optical densitometry of immunohistochemically stained sections. Fluorescence images were captured using a Nikon Eclipse E600 microscope equipped with a Nikon Digital Camera DXM1200 (ATI system).

In CDKL5 knockout male mice (−/Y) the optical density of P-AKT in the molecular layer of the DG (FIG. 31A) and in the layer V of the cortex (FIG. 31B) was observed to be significantly lower than in +/Y mice. In CDKL5 knockout male mice (−/Y) intraventricular injected with TATk-GFP-CDKL5 for five consecutive days this defect were fully rescued (FIGS. 31A and 31B), demonstrating that treatment with TATk-GFP-CDKL5 in CDKL5 knockout mice restores AKT activity.

Example 10: Effect of TATk-CDKL5 Fusion Protein on Learning and Memory Ability

CDKL5 knockout mice exhibit learning and memory deficits as compared to wild-type mice (see e.g. FIGS. 33, and 34A-34B).

To examine memory and learning ability, CDKL5 knockout mice were administered daily intraventricular injections of a TATk-GFP-CDKL5 fusion protein for 10 consecutive days (see e.g. FIG. 32 for experimental schedule). After a two day rest period at the conclusion of 10 days of injections, mice in all groups received the Morris Water Maze (MWM) testing (FIG. 33). MWM measures the ability to find and recall the position of a platform submerged in water. Mice were trained in the MWM task to locate a hidden escape platform in a circular pool. The apparatus consisted of a large circular water tank (1.00 m diameter, 50 cm height) with a transparent round escape platform (10 cm2). The pool was virtually divided into four equal quadrants identified as northeast, northwest, southeast, and southwest. The tank was filled with tap water at a temperature of 22° C. up to 0.5 cm above the top of the platform and the water was made opaque with milk. The platform was placed in the tank in a fixed position (in the middle of the north-west quadrant). The pool was placed in a large room with a number of intra-(squares, triangles, circles and stars) and extra-maze visual cues. After training, each mouse was tested for two sessions of 4 trials each per day, for 5 consecutive days with an inter-session interval of 40 minutes (acquisition phase). A video camera was placed above the center of the pool and connected to a videotracking system (Ethovision 3.1; Noldus Information Technology B.V., Wageningen, Netherlands). Mice were released facing the wall of the pool from one of the following starting points: North, East, South, or West and allowed to search for up to 60 seconds for the platform. If a mouse did not find the platform, it was gently guided to it and allowed to remain there for 15 seconds. During the inter-trail time (15 seconds) mice were placed in an empty cage. The latency to find the hidden platform was used as a measure of learning. All experimental sessions were carried out between 9.00 am and 15.00 pm.

The results of this test are demonstrated in FIG. 33. FIG. 33 shows a graph demonstrating the quantification of the learning phase as determined via the Morris Water Maze test in wild-type male mice (+/Y), CDKL5 knockout male mice (−/Y), and CDKL5 knockout male mice treated with a TATk-GFP-CDKL5 fusion protein (−/Y+TATk-GFP-CDKL5). Wild-type mice learned to find the platform by the second day, but no significant learning was detected in CDKL5 knockout mice. CDKL5 knockout mice treated with a TATk-CDKL5 fusion protein began to recover learning ability at day 4 with continued improvement at day 5.

Memory and learning ability as further examined in response to TATk-GFP-CDKL5 fusion protein treatment using a passive avoidance test. After 10 consecutive days of treatment and a two day rest period, mice of the various groups received passive avoidance testing (FIG. 34). The experiment utilized a test cage with two chambers (light and dark). On day one (conditioning period), animals were placed in the light chamber and instinctively move into the dark chamber where they are conditioned with a single adverse event (foot shock). For the passive avoidance test we used a tilting-floor box (47×18×26 cm) divided into two compartments by a sliding door and a control unit incorporating a shocker (Ugo Basile, Italy). This classic instrument for Pavlovian conditioning exploits the tendency in mice to escape from an illuminated area into a dark one (step-through method). On the first day mice were individually placed into the illuminated compartment. After 60 seconds of habituation period, the connecting door between the chambers opened. In general, mice step quickly through the gate and enter the dark compartment because mice prefer to be in the dark. Upon entering the dark compartment, mice received a brief foot shock (0.7 mA for 3 seconds) and were removed from the chamber after 15 seconds of latency. If the mouse remained in the light compartment for the duration of the trial (358 s), the door closed and the mouse was removed from the light compartment. The chambers were cleaned with 70% ethanol between testing of individual mice. After a 24 hour retention period, mice were placed back into the light compartment and the time it took them to re-enter the dark compartment (latency) was measured up to 358 seconds.

FIGS. 34A-34B demonstrate the results from the passive avoidance test. FIG. 34A indicates that the latency time to enter the dark chamber was similar for all groups. On day two (testing period) (FIG. 34B) animals were again placed in the light chamber. Memory of the adverse event was measured by latency time to enter the dark chamber. CDKL5 knockout mice (−/Y) were severely impaired at performing this task, as demonstrated by a reduced latency to enter the dark compartment in comparison with wild-type mice (+/Y). TATk-GFP-CDKL5 treated knockout mice showed a similar latency time as compared to wild-type mice.

In sum the data demonstrate that TATk-CDKL5 can increase and restore learning and memory ability in CDKL5 knockout mice to levels similar seen in untreated wild-type mice.

Example 11: Effect of TATk-CDKL5 Fusion Protein on Motor Function

CDKL5 knockout mice exhibited prolonged limb clasping when suspended (see e.g. FIGS. 35A-35B).

To examine the effect of TATk-GFP-CDKL5 fusion protein on motor function, mice were administered daily intraventricular injections of TATk-GFP-CDKL5 for 10 consecutive days (FIG. 35). 10 days following the completion of the dosing protocol, animals were suspended in the air by the tail (FIG. 35A and FIG. 35B). All animals were suspended for about 2 minutes and total time of limb clasping was measured. Results from this experiment are demonstrated in FIGS. 35A-35B.

FIG. 35A show a graph demonstrating quantification of motor ability as determined by a clasping test in which total amount of time spent limb clasping during a 2 minute interval was measured in in wild-type male mice (+/Y), CDKL5 knockout male mice (−/Y), and CDKL5 knockout male mice treated with a TATk-GFP-CDKL5 fusion protein (−/Y+TATk-GFP-CDKL5) according to the injection schedule in FIG. 32.

Body weight of wild type (+/Y) and Cdkl5 KO (−/Y) male mice injected for 5 (+/Y) or 10 (−/Y) days with TAT-GFP-CDKL5 protein was measured and results are demonstrated in FIG. 36. No significant changes in body weight during the injection period were observed, suggesting that there were no side effects caused by TAT-GFP-CDKL5 protein administration.

In sum, the data demonstrate that treatment with TATk-CDKL5 improved motor function in CDKL5 knockout mice.

We claim:

1. A method of treating a CDKL5 deficiency, Rett syndrome or a Rett syndrome variant, the method comprising administering a fusion protein to a subject in need thereof, wherein the fusion protein comprises:
 a CDKL5 polypeptide sequence, wherein the CDKL5 polypeptide sequence comprises SEQ ID NO: 2; and
 a TATκ polypeptide sequence, wherein the TATκ polypeptide sequence comprises SEQ ID NO: 4, wherein the TATκ polypeptide is operatively coupled to the CDKL5 polypeptide.

2. The method of claim 1, wherein the fusion protein further comprises an Igk-chain leader sequence polypeptide, wherein the Igk-chain leader sequence is operatively coupled to the CDKL5 polypeptide.

3. The method of claim 1, wherein the fusion protein further comprises a reporter protein polypeptide, wherein the reporter protein polypeptide is operatively coupled to the CDKL5 polypeptide.

4. The method of claim 1, wherein the fusion protein further comprises a protein tag polypeptide, wherein the protein tag polypeptide is operatively coupled to the CDKL5 polypeptide.

5. The method of claim 1, wherein the fusion protein has a polypeptide sequence comprising SEQ ID NO: 8 or SEQ ID NO: 10.

6. The method of claim 1, wherein administering the fusion protein increases neurite growth, elongation, branch number, or branch density in the brain of a treated subject as compared to an untreated control subject.

7. The method of claim 1, wherein administering the fusion protein reduces neuron apoptosis in the brain of a treated subject as compared to an untreated control subject.

8. The method of claim 1, wherein the subject has a CDKL5 deficiency.

9. The method of claim 1, wherein the subject has Rett syndrome.

10. The method of claim 1, wherein the subject has a Rett syndrome variant.

11. A method of treating a CDKL5 deficiency, Rett syndrome or a Rett syndrome variant, the method comprising administering a fusion protein to a subject in need thereof, wherein the fusion protein comprises:
 a CDKL5 polypeptide sequence, wherein the CDKL5 polypeptide sequence comprises SEQ ID NO: 16; and
 a TATκ polypeptide sequence, wherein the TATκ polypeptide sequence comprises SEQ ID NO: 4, wherein the TATκ polypeptide is operatively coupled to the CDKL5 polypeptide.

12. The method of claim 11, wherein the fusion protein further comprises an Igk-chain leader sequence polypeptide, wherein the Igk-chain leader sequence is operatively coupled to the CDKL5 polypeptide.

13. The method of claim 11, wherein the fusion protein further comprises a reporter protein polypeptide, wherein the reporter protein polypeptide is operatively coupled to the CDKL5 polypeptide.

14. The method of claim 11, wherein the fusion protein further comprises a protein tag polypeptide, wherein the protein tag polypeptide is operatively coupled to the CDKL5 polypeptide.

15. The method of claim 11, wherein the fusion protein has a polypeptide sequence comprising SEQ ID NO: 12 or SEQ ID NO: 14.

16. The method of claim 11, wherein administering the fusion protein increases neurite growth, elongation, branch number, or branch density in the brain of a treated subject as compared to an untreated control subject.

17. The method of claim 11, wherein administering the fusion protein reduces neuron apoptosis in the brain of a treated subject as compared to an untreated control subject.

18. The method of claim 11, wherein the subject has a CDKL5 deficiency.

19. The method of claim 11, wherein the subject has Rett syndrome.

20. The method of claim 11, wherein the subject has a Rett syndrome variant.

* * * * *